(12) United States Patent
Matsumoto et al.

(10) Patent No.: US 7,339,656 B2
(45) Date of Patent: Mar. 4, 2008

(54) METHOD AND APPARATUS FOR MEASURING ELECTRON DENSITY OF PLASMA AND PLASMA PROCESSING APPARATUS

(75) Inventors: Naoki Matsumoto, Nirasaki (JP);
Yohei Yamazawa, Nirasaki (JP);
Chishio Koshimizu, Nirasaki (JP);
Tatsuo Matsudo, Nirasaki (JP); Sumie Segawa, Nakakoma-gun (JP)

(73) Assignee: Tokyo Electron Limited, Tokyo (JP)

( * ) Notice: Subject to any disclaimer, the term of this patent is extended or adjusted under 35 U.S.C. 154(b) by 477 days.

(21) Appl. No.: 10/831,757

(22) Filed: Apr. 26, 2004

(65) Prior Publication Data

US 2005/0009347 A1    Jan. 13, 2005

(30) Foreign Application Priority Data

| Apr. 24, 2003 | (JP) | ............................ 2003-119279 |
| Apr. 28, 2003 | (JP) | ............................ 2003-123442 |
| Jan. 16, 2004 | (JP) | ............................ 2004-009100 |
| Apr. 13, 2004 | (JP) | ............................ 2004-117817 |

(51) Int. Cl.
*G01N 21/00* (2006.01)
(52) U.S. Cl. ..................................................... 356/72
(58) Field of Classification Search ........... 156/345.24; 315/111.71; 204/298.32, 298.03; 356/72
See application file for complete search history.

(56) References Cited

U.S. PATENT DOCUMENTS

| 6,184,623 B1 | 2/2001 | Sugai et al. |
| 6,339,297 B1 | 1/2002 | Sugai et al. |
| 6,744,211 B2 | 6/2004 | Sugai et al. |
| 6,861,844 B1 * | 3/2005 | Verdeyen et al. ........... 324/464 |
| 2002/0047543 A1 * | 4/2002 | Sugai et al. ............ 315/111.21 |
| 2002/0114123 A1 * | 8/2002 | Nishio et al. ................ 361/234 |

FOREIGN PATENT DOCUMENTS

| JP | 10-270417 | 10/1998 |
| JP | 2000-100598 | 4/2000 |
| JP | 2000-100599 | 4/2000 |
| JP | 2001-196199 | 7/2001 |

\* cited by examiner

*Primary Examiner*—Gregory J. Toatley, Jr.
*Assistant Examiner*—Kara Geisel
(74) *Attorney, Agent, or Firm*—Oblon, Spivak, McClelland, Maier & Neustadt, P.C.

(57) ABSTRACT

An apparatus for measuring plasma electron density precisely measures electron density in plasma even under a low electron density condition or high pressure condition. This plasma electron density measuring apparatus includes a vector network analyzer in a measuring unit, which measures a complex reflection coefficient and determines a frequency characteristic of an imaginary part of the coefficient. A resonance frequency at a point where the imaginary part of the complex reflection coefficient is zero-crossed is read and the electron density is calculated based on the resonance frequency by a measurement control unit.

31 Claims, 41 Drawing Sheets

FIG.2
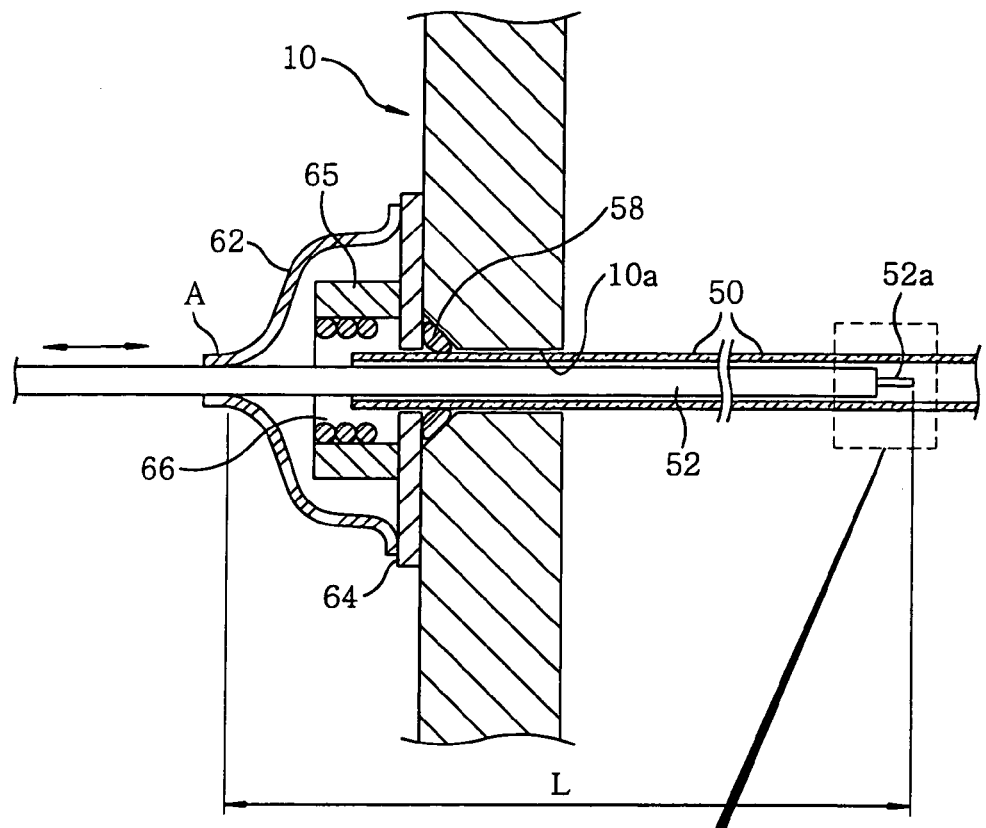
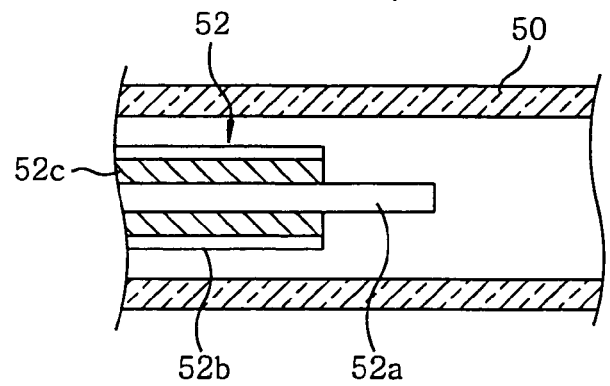

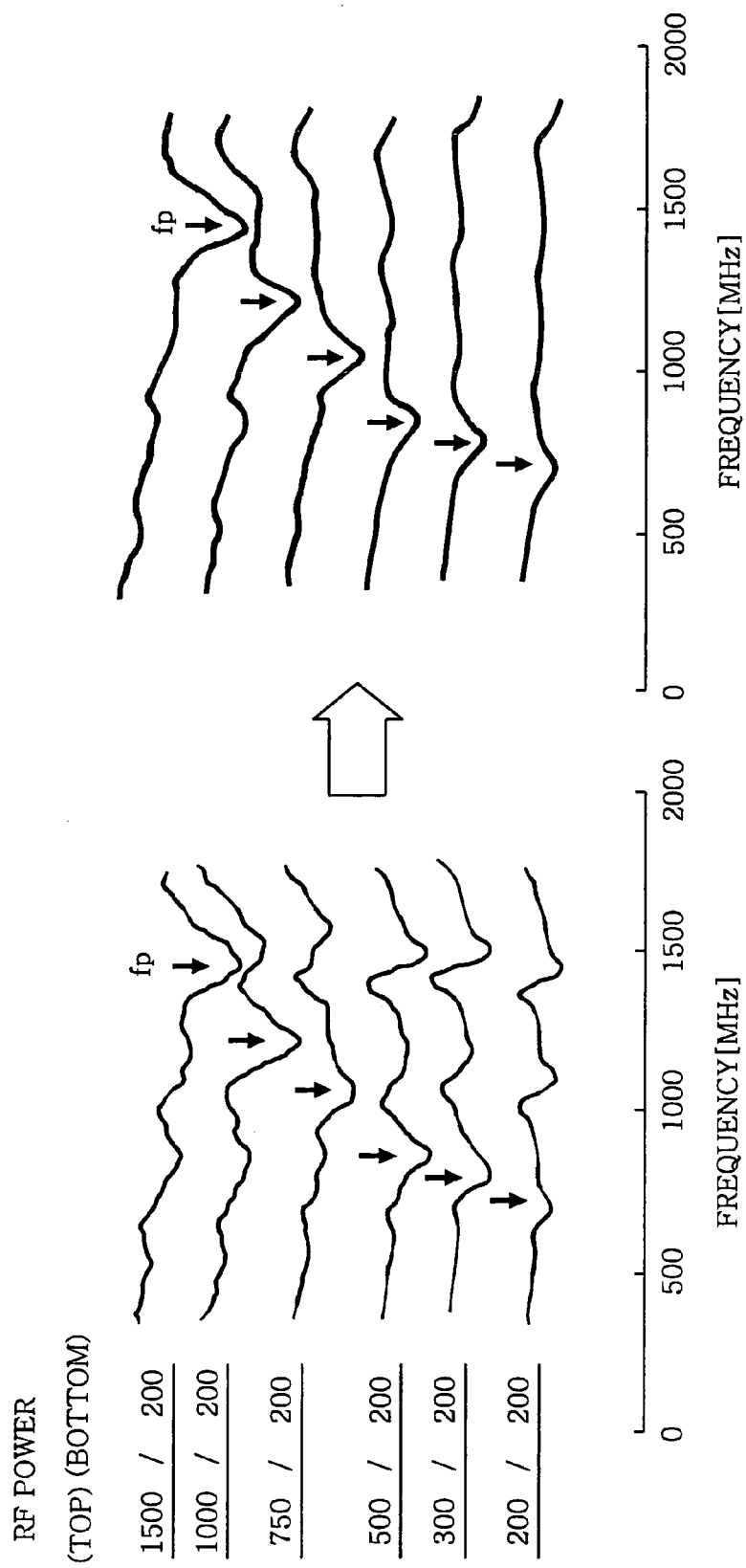

METHOD AND APPARATUS FOR MEASURING ELECTRON DENSITY OF PLASMA AND PLASMA PROCESSING APPARATUS

TECHNICAL FIELD

The present invention relates to a technology of monitoring plasma in a chamber of a plasma processing apparatus and so on; and more particularly, to plasma monitoring method and apparatus for measuring electron density in plasma and light emission from the plasma.

PRIOR ART

In etching, depositing, oxidizing and sputtering treatments of a semiconductor device or flat panel display (FPD) manufacturing process, plasma is widely used to cause processing gas to desirably react at relatively low temperatures. Generally, in a plasma processing apparatus, it is necessary to uniformly perform plasma treatment over a surface of a substrate to be processed so as to obtain a high yield. To this end, it is necessary to create plasma so that plasma density, i.e., electron density, is uniformly distributed in a processing space. From this point of view, a technology of precisely measuring electron density in plasma is indispensable in the design or installation stage of a plasma processing apparatus so as to identify how electron density is distributed in plasma that is created in the plasma processing space of a chamber.

Recently, for such a monitoring technology, a plasma absorption probe (PAP) method is attracting attention. This monitoring method uses an antenna probe coated with an insulation pipe, so that it does not disturb the electrical potential of plasma or does not cause metallic contamination in a chamber unlike a Langmuir probe method, thus being capable of performing measurement in the plasma of reactive gas. Furthermore, the PAP method is advantageous in that the PAP method is a measurement method in a GHz band, so that the measurement thereof is not affected by an inductive deposited film even though the inductive deposited film is attached to the surface of the insulating pipe, and thus, the PAP method can perform measurement even in the plasma of deposition gas.

As shown in FIG. 50, in the conventional PAP method (for example, refer to Patent Documents 1, 2 and 3), an insulating pipe 202 closed at the front end thereof is slidably inserted into a through hole 200a provided in the sidewall of a chamber 200, a coaxial cable 204 having a probe portion 204a formed by exposing several millimeters of the core wire of the front portion of the coaxial cable 204 is inserted into the insulating pipe 202, and the other end of the coaxial cable 204 is connected to a scalar network analyzer 206. In the chamber 200, parallel flat plate upper and lower electrodes 208 and 210 connected to, e.g., a high frequency power supply (not shown) are arranged as a plasma creating mechanism, and processing gas is supplied to a gap space between the electrodes 208 and 210 in a depressurized state, thus generating the plasma PZ of the processing gas. In the example shown, a substrate W to be processed is loaded on the lower electrode 210. An O-ring 212 for supporting the insulating pipe 202 and vacuum-sealing the through hole 200a is fitted into the through hole 200a provided in the sidewall of the chamber.

The scalar network analyzer 206 transmits a minute power electromagnetic signal (incident wave) to the probe portion 204a of the coaxial cable 204 with respect to each frequency in a band ranging from several hundred MHz to several GHz while performing frequency sweeping, such that the signal is irradiated toward the plasma PZ contained in the chamber 200, and obtains a reflection coefficient in scalar form from the ratio of the amount of power of an electromagnetic wave (reflected wave) reflected from the plasma PZ to the amount of power of the incident wave, thus obtaining the frequency characteristic of the reflection coefficient. In more detail, the probe portion 204a is placed at a desired measurement location, the high frequency power supply for plasma creation is turned off and, simultaneously, the supply of processing gas is halted, the frequency characteristic of the reflection coefficient $\Gamma(f)$ (S11 parameter) is obtained by the network analyzer 206 in the state where the plasma PZ does not exist in the chamber 200, and the measured data is stored in a memory. Subsequently, by turning on the high frequency power supply and, simultaneously, supplying the processing gas, the frequency characteristic of the reflection coefficient $\Gamma(pf)$ is obtained by the scalar network analyzer 206 in the state where the plasma PZ has been created in the chamber 200. Meanwhile, in the frequency characteristics of the ratio of the two reflection coefficients $\Gamma(pf)/\Gamma(f)$, the frequency where a waveform is minimized (has the minimum peak) is considered a plasma absorption frequency. Furthermore, this plasma absorption frequency is considered to be identical with an electron frequency $f_p(=1/2\pi\sqrt{e^2 * N_e/m_e * \epsilon_0})$ in plasma, so that electron density Ne is calculated from the following Equation 1.

$$N_e = m_e * \epsilon_0 * (1+\epsilon_r) * (2\pi f_p/e)^2 = 0.012 * (1+\epsilon_r) * f_p^2 [m^{-3}] \quad (1)$$

where $m_e$ is an electronic mass, $\epsilon_0$ is a vacuum permittivity, $\epsilon_r$ is a relative permittivity of the insulating pipe, and e is an elementary electric charge.

To investigate the spatial distribution of electron density in the plasma PZ, the probe portion 204a is sequentially moved to a plurality of measurement locations by pushing or pulling the insulating pipe 202 in the axial (longitudinal) direction, the frequency characteristics of reflection coefficients $\Gamma(f)$ and $\Gamma(pf)$ are obtained by the scalar network analyzer 206 while the ON and OFF of plasma creation are switched at each of the measurement locations, and the calculation of a plasma absorption frequency or electron density is performed. Generally, the location of the probe portion 204a, that is, measurement location, is moved by a desired pitch in steps, and the measured values of electron density obtained at respective measurement locations are plotted on a graph.

Furthermore, conventionally, in the development of a plasma processing apparatus, the development of a plasma process, or an actual plasma process, a technology of monitoring plasma light emission in a processing chamber has been used. In the conventional plasma light emission measuring method, plasma light emission in a chamber is measured through a window attached to the sidewall of the processing chamber. Typically, spectrum of a certain wavelength is extracted from plasma light exiting from the processing chamber through the window using a spectroscope or an optical filter, and the intensity or variation of the extracted spectrum is measured (for example, refer to Patent Document 4).

[Patent Document 1]
Japanese Unexamined Pat. Publication No. 2000-100598

[Patent Document 2]
Japanese Unexamined Pat. Publication No. 2000-100599

[Patent Document 3]
Japanese Unexamined Pat. Publication No. 2001-196199

[Patent Document 4]
Japanese Unexamined Pat. Publication No. 1998-270417

DISCLOSURE OF THE INVENTION

Problems to be Solved by the Invention

However, the above-described PAP method is problematic in that the measured value of a plasma absorption frequency is dependent on a waveform profile in the frequency characteristic of a reflection coefficient, so that a deviation easily occurs in the measured value of electron density. That is, when an absorption peak (minimum peak) appears as a sharp angled waveform, the frequency of a peak, that is, a plasma absorption frequency, can be precisely measured. However, when the absorption peak (minimum peak) appears as a broad waveform having a round front end, a peak point is indefinite, so that an error easily occurs in a measured value. Such a broad absorption peak waveform appears typically when the plasma density (electron density) of a measurement point is low. Furthermore, since, under a high pressure condition, signal power absorption due to collisions between gas molecules in plasma cannot be ignored, noise is increased, so that it is difficult to observe the net power absorption based on electronic oscillations, thus reducing S/N.

Furthermore, in the above-described conventional PAP method, since the ON and OFF of plasma creation are switched whenever a measurement location is changed, a measurement time of several minutes is required for a single measurement location. Furthermore, since the PAT method slides the insulating pipe 202 to change the measurement location, a considerable time is required to move and position the probe portion 202a to and at the next measurement location. For this reason, even when ten measurement points are selected, the total measurement time is at least several ten minutes. When the spatial distribution of electron density is to be precisely evaluated by shortening the step distances or intervals between measurement points, a plurality of measurement points (for example, 100 or more) are necessary, so that the total measurement time may exceed several hours. Further, when the dependency or correlation of electron density on or with the input parameters of plasma processing (RF power, pressure, gas species, the distance between electrodes, the structure of electrodes, the structure and material of a chamber) is to be precisely evaluated, a considerably much measurement time is required. The problem is more critical, particularly in 300 mm-diameter wafer and FPD processing apparatuses having large diameter chambers.

Furthermore, in accordance with the conventional plasma light emission measuring method, plasma light emission in a chamber should be measured through the window of the sidewall of the chamber in the form of an average value, but not in the form of a spatial distribution in the chamber. Accordingly, the correlation between the intra-surface distribution of the processing results related to a processed substrate and the spatial distribution of plasma light emission cannot be investigated.

The present invention has been made keeping in mind the above problems occurring in the prior art, and an object of the present invention is to provide a method and an apparatus for monitoring plasma and a plasma processing apparatus, which are capable of measuring electron density in plasma in high precision in any plasma condition, especially even in a low electron density or high pressure condition.

Another object of the present invention is to provide a method and an apparatus for monitoring plasma which are capable of efficiently measuring electron density in plasma in a short time.

Still another object of the present invention is to provide a method and an apparatus for monitoring plasma, which improves the stability and durability of a probe structure by guaranteeing the reproducibility of measurement locations, improves S/N characteristics by stabilizing influence on plasma, and is capable of performing the stable and highly precise measurement of electron density in plasma.

Still another object of the present invention is to provide a method and an apparatus for monitoring plasma, which is capable of assuring safety for a human body or measurement equipment by effectively preventing the leakage of radio frequency noise to the atmosphere or the measurement equipment.

Still another object of the present invention is to provide a method and an apparatus for monitoring plasma, which has high reliability by measuring the light emission of plasma using a spatial distribution in a chamber without disturbing the plasma.

Still another object of the present invention is to provide a method and an apparatus for monitoring plasma, which is capable of measuring the light emission of plasma using a spatial distribution in a chamber even during an actual process.

Still another object of the present invention is to provide a plasma processing apparatus, which is capable of assuring the uniformity of plasma density and further the uniformity of plasma processing for a surface of a substrate to be processed.

To achieve the above-described objects, a method of monitoring plasma in accordance with a first aspect of the present invention includes the steps of: placing an antenna probe at a desired monitoring location set inside or near plasma existing within a certain space; causing the antenna probe to irradiate a frequency-variable electromagnetic wave into the plasma; receiving the electromagnetic wave reflected from the plasma to the probe antenna; measuring a complex reflection coefficient from the incident and reflected electromagnetic waves, and obtaining the imaginary part of the complex reflection coefficient; measuring a resonance frequency at which the imaginary part of the complex reflection coefficient is zero by sweeping the frequencies of the electromagnetic waves; and calculating electron density in the plasma based on the measured value of the resonance frequency.

Additionally, an apparatus for monitoring plasma in accordance with the first aspect of the present invention includes: an antenna probe located in the wall of or inside a chamber in or into which plasma is created or introduced; a vector reflection coefficient measuring unit for transmitting electromagnetic waves of respective frequencies to the antenna probe while sweeping frequencies to be irradiated to the plasma, receiving reflected waves from the plasma through the antenna probe, and measuring complex reflection coefficients; a resonance frequency measuring unit for measuring a resonance frequency at which an imaginary part of the complex reflection coefficients is zero; and an electron density operation unit for calculating electron density in the plasma based on the measured value of the resonance frequency.

In the present invention, a complex reflection coefficient is measured using the vector reflection coefficient measuring unit, and an imaginary part of the complex reflection coefficient is obtained. Furthermore, a resonance frequency at which the imaginary part of the complex reflection coefficient is zero is measured by a resonance frequency measuring unit, and the electron density is calculated in plasma by the electron density operation unit based on the measured value of the resonance frequency. In the present invention, the signal transmission characteristic of plasma reactance with respect to an electromagnetic wave is monitored through the imaginary part of the complex reflection coefficient, the frequency at which the imaginary part of the complex reflection coefficient is zero is considered a resonance frequency at which Landau damping occurs due to the series resonance of the plasma reactance, and the measured electron density is obtained from the measured value of the resonance frequency.

In accordance with a preferred embodiment of the present invention, the frequency character of the imaginary part of the complex reflection coefficient is obtained by sweeping the frequencies of an electromagnetic wave by the vector reflection coefficient measuring unit, and a frequency of a point where a sign of the imaginary part of the complex reflection coefficient changes from negative (+) to positive (−) or from positive (+) to negative (−) is calculated as the resonance frequency by a resonance frequency measuring unit based on the frequency characteristic.

Furthermore, in accordance with another preferred embodiment of the present invention, a first frequency characteristic is obtained with respect to the imaginary part of the complex reflection coefficient by sweeping the frequencies of the electromagnetic wave in a state where the plasma does not exist in the space, a second frequency characteristic is obtained with respect to the imaginary part of the complex reflection coefficient by sweeping the frequencies of the electromagnetic wave in a state where the plasma exists in the space, and a normalized frequency characteristic is obtained based on the first and second frequency characteristics. In accordance with this method, the switching of plasma ON/OFF is performed only once regardless of the number of measurement points, so that the total measurement time can be considerably reduced.

A plasma processing apparatus in accordance with the present invention includes: a chamber for accommodating an object to be processed; a gas supply unit for supplying certain gas into the chamber; a plasma creation unit for creating plasma, which is used to perform a certain treatment on the object to be processed, by discharging electricity in the gas; an exhaust unit for maintaining the chamber at a certain pressure by depressurizing the inside of the chamber; and the plasma monitoring apparatus of the present invention.

By employing the plasma monitoring apparatus of the present invention having the above-described configuration, the state of plasma density in the chamber and the status of plasma processing can be precisely monitored, so that the quality of plasma processing can be improved.

In the plasma processing apparatus of the present invention, a monitor unit for monitoring the state of plasma processing in the chamber based on the measured value of the electron density obtained from the plasma monitoring apparatus is provided. More preferably, a process control unit for controlling at least one of process parameters influencing plasma processing so that the measured value of the electron density obtained from the plasma monitoring apparatus is maintained within a certain range may be provided.

Additionally, in a preferred embodiment, there is provided a seasoning control unit for performing seasoning based on the characteristic of the time variation of the measured values of the electron density obtained from the plasma monitoring apparatus with respect to processing conditions after a cleaning of the chamber or a replacement of parts. In a preferred embodiment, the seasoning control unit obtains a representative of the measured values of the electron density time-varying during the plasma processing with respect to respective dummy substrates being processed, completing the seasoning when the representative is stabilized to an actual normal value between successive dummy substrates, and changes a substrate being put into the chamber from the dummy substrate to a normal substrate to be processed.

Additionally, in a preferred embodiment, the antenna probe of the plasma processing apparatus may be attached to the wall of the chamber, electrodes for creating plasma, or a mounting table for supporting an object to be processed.

Additionally, in a preferred embodiment, a selection switch may be provided for selecting any one of a plurality of antenna probes arranged at different locations to be electrically connected to the reflection coefficient measuring unit. By electrically connecting the plurality of antenna probes to the reflection coefficient measuring unit sequentially in a time division manner using the selection switch, simultaneous measurements at a plurality of monitoring locations can be efficiently realized by a single measurement device.

A method of monitoring plasma in accordance with a second aspect of the present invention includes the steps of: placing an antenna probe at a desired location set inside or in the vicinity of plasma existing within a certain space; irradiating frequency-variable electromagnetic waves from the antenna probe to the plasma; receiving electromagnetic waves reflected from the plasma to the antenna probe; measuring a phase difference between the incident and reflected waves; measuring a resonance frequency at which the phase difference is zero while sweeping the frequencies of the electromagnetic waves; and calculating electron density in the plasma based on the measured value of the resonance frequency.

Additionally, an apparatus for monitoring plasma in accordance with the second aspect of the present invention includes: an antenna probe located in the wall of or inside a chamber in or into which plasma is created or introduced; a phase difference measuring unit for transmitting electromagnetic waves of respective frequencies to the antenna probe while sweeping frequencies such that the electromagnetic waves are irradiated to the plasma, receiving reflected waves from the plasma through the antenna probe, and measuring a phase difference between the incident and reflected waves; a resonance frequency measuring unit for obtaining the measured resonance frequency at which the phase difference obtained from the phase difference measuring unit is zero, and an electron density operation unit for calculating electron density in the plasma based on the measured resonance frequency.

In the method and apparatus for monitoring plasma in accordance with the second aspect of the present invention, a sign of in the phase difference between incident and reflected waves measured by the phase difference measuring unit corresponds to a sign of the imaginary part of complex reflection coefficient, and the frequency at which a phase difference is zero is a frequency at which the imaginary part of the complex reflection coefficient is zero, that is, a resonance frequency. Accordingly, the highly precise measured value of electron density can be obtained based on the resonance frequency calculated from the phase difference.

A method of monitoring plasma in accordance with a third aspect of the present invention includes the steps of: inserting and attaching an insulating pipe into and to a chamber in or into which plasma is created or introduced; inserting a coaxial cable, which has a probe portion formed by exposing a front core wire of the coaxial cable, into the insulating pipe; in the state where the plasma does not exist in the chamber, obtaining a first frequency characteristic with respect to a reflection coefficient of an electromagnetic wave irradiated from the probe portion placed in the insulating pipe; in the state where the plasma exists in the chamber, obtaining a second frequency characteristic with respect to the reflection coefficient of the electromagnetic wave irradiated from the probe portion placed in the insulating pipe; and measuring a plasma absorption frequency based on the first and second frequency characteristics.

An apparatus for monitoring plasma in accordance with the third aspect of the present invention includes: an insulating pipe inserted and attached into and to a chamber in or into which plasma is created or introduced; a coaxial cable provided with a probe portion formed by exposing a core wire of a front end of the coaxial cable, and inserted into the insulating pipe from one end of the insulating pipe; an actuator for moving the coaxial cable in an axial direction of the insulating pipe; a scalar reflection coefficient measuring unit for transmitting electromagnetic signals of respective frequencies to the probe portion of the coaxial cable at certain power while sweeping frequencies such that the electromagnetic signals are irradiated to a surrounding space, measuring reflection coefficients from the levels of signals reflected through the probe portion with respect to the respective frequencies, and obtaining the frequency characteristics of the reflection coefficients; and a measurement operation unit for obtaining the measured values of plasma absorption frequencies from first frequency characteristics obtained from the reflection coefficient measuring unit in the state where plasma does not exist in the chamber and second frequency characteristics obtained from the reflection coefficient measuring unit in the state where plasma exists in the chamber, at measurement locations determined by the locations of the probe portion.

In the method and apparatus for monitoring plasma in accordance with the third aspect of the present invention, the measurement of reflection coefficients in the state where plasma does not exist in the chamber (OFF state) and the measurement of reflection coefficients in the state where plasma exists or is being created in the chamber (ON state) are performed in batch, respectively, so that the switching of plasma ON/OFF is performed once regardless of the number of measurement points, so that the total measurement time can be considerably reduced.

In a preferred embodiment of the third aspect, in the state where the plasma does not exist in the chamber, the coaxial cable is moved in an axial direction of the insulating pipe, and the first frequency characteristics are measured at a plurality of measurement locations; in the state where the plasma exists in the chamber, the coaxial cable is moved in an axial direction of the insulating pipe, and the second frequency characteristics are measured at a plurality of measurement locations; and a measured value of the plasma absorption frequency is obtained based on the first and second frequency characteristics at the plurality of measurement locations. In this case, preferably, the probe portion is sequentially positioned at the plurality of measurement locations, and the first and second frequency characteristics may be obtained at the plurality of measurement locations with respect to the reflection coefficients of the electromagnetic wave irradiated from the probe portion. In this embodiment, the probe portion is sequentially positioned at respective measurement locations at short tact intervals in a plasma OFF or ON state, and a measured data of reflection coefficients can be obtained at all the measurement locations in a short time. Preferably, the probe portion may be sequentially positioned at the plurality of measurement locations by pulling the coaxial cable out of the insulating pipe, through the use of an actuator.

In a preferred embodiment of the present invention, the insulating pipe accommodating a coaxial cable equipped with a probe portion is hung between first and second supports provided in the sidewalls of the chamber. In this case, at least one of the first and second supports may be formed of a through hole. Furthermore, the insulating pipe may be airtightly and fixedly attached in the through hole using an O-ring.

In accordance with such bridge-type insulating pipe mounting structure, the insulating pipe is supported at two locations (first and second supports) on the wall of the chamber, so tat the insulating pipe is not vibrated by an operation of positioning the probe and is not bent by its own weight. Accordingly, the probe portion can be rapidly and precisely positioned at a desired measurement location and can be located at a point on a line, so that the reproducibility of measurement locations can be guaranteed. Furthermore, at the time of positioning the probe, the coaxial cable is preferably moved in an axial direction of the insulating pipe fixed to the chamber. Since there is no friction between the insulating pipe and the support, there is no concern for the damage or deterioration of the support. Accordingly, the stability of a probe mechanism is proved, so that the cost of consumables is reduced. Furthermore, the disturbance of plasma attributable to the probe mechanism is uniform regardless of measurement locations, so that the reliability of the measurement is high. The insulating pipe has a coaxial pipe structure that is constant or uniform at any measurement location when viewed from the probe portion of the coaxial cable, and the coupling of an electromagnetic wave generated from the probe portion with plasma is constant, so that an generation of noise is suppressed, so that measurement having high precision and reproducibility can be guaranteed. Further, an insulating pipe mounting structure in which the insulating pipe is attached in the chamber by a single support, e.g., a cantilever is also possible.

In the present invention, the outer conductor of the coaxial cable may be electrically connected to a grounding potential through the chamber. In particular, there may be provided a grounding conductor one end of which is connected to a grounding potential portion of the chamber and the other end of which is connected to the outer conductor of the coaxial cable. In accordance with this method or configuration, the leakage of RF noise to the atmosphere or the measuring unit is effectively prevented, so that the safety of the human body or a measurement device is guaranteed while avoiding the malfunction of surrounding electronic equipment, such as a gas detector.

Preferably, a noise signal (typically, a noise signal attributable to a standing wave propagating along the outer conductor) may be absorbed into an electromagnetic wave absorber through electromagnetic induction at a location around the probe portion side of the coaxial cable when viewed from the location where the grounding conductor and the outer conductor of the coaxial cable are in contact with each other. The electromagnetic wave absorber preferably is one or more bead-shaped ferrite members placed around the coaxial cable along the axial direction thereof. In accordance with this method or configuration, even though noise, such as standing wave noise, occurs on the outer conductor (grounding portion), the noise can be effectively absorbed and eliminated by the electromagnetic wave absorber.

Preferably, cooling gas may be allowed to flow in the insulating pipe through an opening formed at the other end of the insulating pipe. In particular, the other end of the insulating pipe is opened, and a cooling device for allowing the cooling gas to flow may be connected to the opening. In accordance with this method or configuration, the coaxial cable in the insulating pipe can be effectively cooled, so that thermal expansion or thermal damage around the probe portion can be prevented, thus improving its durability.

A method of monitoring plasma in accordance with a fourth aspect of the present invention includes the steps of: inserting and attaching a transparent insulating pipe into and to a chamber in or into which plasma is created or introduced; inserting a rod-shaped optical transmission probe, which has a light receiving surface at a front end thereof, into the insulating pipe from one end of the insulating pipe; and allowing light generated by the plasma in the chamber to be incident on the light receiving surface of the probe through the insulating pipe, and measuring light emission from the plasma based on light irradiated from the other end of the probe.

An apparatus for monitoring plasma in accordance with the fourth aspect of the present invention includes: a transparent insulating pipe inserted and attached into and to a chamber in or into which plasma is created or introduced; a rod-shaped light transmission probe provided with a light receiving surface at a front end thereof, and inserted into the insulating pipe from one end of the insulating pipe; and a measurement unit for measuring light emission from the plasma based on light irradiated from the other end of the probe.

In the plasma light emission monitoring method of the present invention, the insulating pipe is inserted into the chamber, the rod-shaped optical transmission probe is moved in the insulating pipe in an axial direction thereof, light emission from plasma is collected on the light receiving surface of the probe at a measurement location in the axial direction, the collected plasma light is transmitted to the measurement unit, and a measured value of a certain characteristic or attribute (for example, a certain wavelength or the intensity of a spectrum) is obtained by the measurement unit with respect to plasma emission at each measurement location. In this case, the insulating pipe and the probe are made of non-metal, which does not disturb the plasma even though being inserted into the plasma in the chamber, thereby performing highly reliable and precise spatial distribution measurement.

In a preferred embodiment of the present invention, the probe is moved in the insulating pipe in the axial direction thereof (preferably, in a radial direction of the chamber), and the plasma light emission is measured in the form of a spatial distribution along the axial direction. In this case, the axial direction of the probe may coincide with the radial direction of the chamber. Alternately, the probe, together with the insulating pipe, is moved in a height direction, and the plasma light is measured in the form of a spatial distribution in the height direction.

In the present invention, the probe may be made of quartz or sapphire. However, to block faint light emitting from the side thereof, the probe preferably has a dual structure that includes a core made of quartz or sapphire and a cladding placed around the core. The probe preferably has a light shielding coating thereon. Furthermore, the probe is preferably constructed to include a bundle of optical fibers and a heat-resistant non-metallic member, such as polyamide, surrounding the optical fibers.

To improve the light collecting function of the probe, in particular, its directionality, plasma light incident from a desired direction is preferably guided to be incident on a mirror at the front end of the probe such that the plasma light reflected by the mirror is incident on the light receiving surface of the probe. More preferably, a light shielding member is attached to the front end of the probe to surround the light receiving surface and the mirror, and the plasma light incident from a desired direction is made to be incident on the mirror through a window provided on the light shielding member. A reflecting surface of the mirror is preferably made of aluminum having a certain high reflection factor with respect to rays ranging from an ultraviolet ray to an infrared ray.

To allow undesired light to be incident on the bundle fiber at an angle larger than the numerical aperture of the bundle fiber, one end of the probe is preferably cut so that the normal line of the light receiving surface of the probe is inclined toward the window at a certain angle with respect to the axial direction of the probe.

In the present invention, the material of the transparent insulating pipe preferably is quartz or sapphire having superior wavelength transmittance, heat-resistant property and anti-corrosion property. To perform the stable and high speed scanning of the probe, the insulating pipe is preferably hung between first and second supports provided to be opposed to each other in the sidewalls of the chamber.

In a method of monitoring plasma in accordance with a fifth aspect of the present invention, an opening, which is selectively opened and closed, is provided in the sidewall of a chamber in or into which plasma is created or introduced, a rod-shaped optical transmission probe, which has a light receiving surface at a front end thereof, is inserted into the chamber from the opening in a depressurized space, and light emission from the plasma is measured based on light irradiated from the other end of the probe.

Further, a plasma light emission measuring apparatus in accordance with the fifth aspect of the present invention includes: an opening, which is selectively opened and closed, provided in the sidewall of a chamber in or into which plasma is created or introduced; a rod-shaped optical transmission probe provided with a light receiving surface at a front end thereof, and inserted into the chamber from the opening in a depressurized space; and a measurement unit for measuring light emission from the plasma based on light irradiated from the other end of the probe.

In this scheme, the probe is inserted into the chamber from the opening of the sidewall of the chamber while the opening is opened, the probe is moved in the axial direction thereof (preferably, in the radial direction of the chamber), the plasma light collected on the light receiving surface of the probe is transmitted to the measurement unit, and a measured value of a certain characteristic or attribute (for example, a certain wavelength or the intensity of a spectrum) is obtained with respect to plasma light emission at each measurement location using the measurement unit. Preferably, the variation of plasma light is obtained with respect to the moving distance of the probe, and the plasma light may be measured in the form of a spatial distribution in the chamber in the axial direction of the probe. The probe preferably includes a core made of quartz or sapphire and a cladding placed around the core.

Further, in order to form a depressurized space around the probe outside the chamber, an expansible and contractible bellows is preferably provided in the radial direction of the chamber and the inner space of the bellows may be exhausted of air through an exhaust unit. Furthermore, to prevent a reaction product (deposit) from adhering to the probe when the probe is exposed to a plasma region in the chamber, it is preferable to heat the probe to an appropriate temperature outside the chamber.

In this scheme, the plasma is not disturbed by the probe because the probe is made of non-metal, and processing results are not influenced because probe scanning can be performed in a short time at high speed, so that the scheme can be applied to the development of a process as well as an actual process.

In the plasma light emission monitoring method, the actuator is preferably used to move the probe in the axial direction, and stable and high-speed probe scanning can be performed by the forward operation of the actuator. Further, in the measuring processing of the present invention, a certain wavelength spectrum is extracted from light irradiated from the outer end of the probe by a spectroscope (spectroscope or optical filter), and the intensity of the corresponding spectrum may be measured. Further, the light irradiated from the other end of the probe is preferably provided to the measurement unit through the bundle fiber. In this way, the light emission of the plasma can be measured with directionality equal or equivalent to that of the case where the light receiving surface of the bundle fiber is put into the chamber.

Effects of the Invention

In accordance with the present invention, electron density in plasma can be accurately and precisely measured by employing the above-described configuration and operation under arbitrary plasma conditions, in particular, a low electron density condition or high pressure condition. Further, the uniformity of plasma density or the quality of plasma processing can be improved based on the highly reliable measured values of electron density. Furthermore, it is possible to efficiently measure a plasma resonance frequency or electron density in a short time. Furthermore, the stability and durability of a probe structure are improved by guaranteeing the reproducibility of measurement locations, S/N characteristics are improved by stabilizing or eliminating an influence of the probe on plasma, and thus the stable and highly precise measurement of a plasma resonance frequency or electron density can be performed. Plasma light emission can be measured with high reliability and precision in the form of a spatial distribution within a chamber without disturbing the plasma. Furthermore, the uniformity of plasma density and further the uniformity of plasma processing on a surface of a substrate to be processed are guaranteed, so that a yield can be improved.

Best Modes for Carrying out the Invention

In the following, with reference to FIGS. 1 to 49, preferred embodiments of the present invention will be described in detail.

EMBODIMENT 1

With reference to FIGS. 1 to 18, a first embodiment of the present invention is described. FIGS. 1 and 2 show a configuration of a plasma processing apparatus, to which a method and an apparatus for measuring electron density of plasma are applied, in accordance with a first embodiment of the present invention. This plasma processing apparatus is a capacitively coupled parallel flat plate type plasma processing apparatus.

A chamber 10 of the plasma processing apparatus is made of, for example, aluminum, and is composed of a processing chamber that is cylindrically shaped and can be sealed. A support 14 made of, e.g., aluminum is placed on the bottom of the chamber 10 with an insulating plate 12 being interposed therebetween, and a susceptor 16 made of, e.g., aluminum is seated on the support 14. The susceptor 16 constitutes a lower electrode, and a substrate to be processed, such as a semiconductor wafer W, is mounted thereon.

A high frequency power supply 18 for supplying high-frequency power to attract ions is electrically connected to the susceptor 16 through a matching unit (not shown), and additionally, a High-Pass Filter (HPF) 22 for passing therethrough a high frequency wave applied from an upper electrode to be described below is electrically connected to the susceptor 16. An electrostatic chuck (not shown) for securing and maintaining the substrate W using, e.g., electrostatic attraction may be placed on the upper surface of the susceptor 16. Furthermore, a cooling or heating means (not shown) for controlling temperature may be provided in the susceptor 16 or support 14.

An upper electrode 24 is located above the susceptor 16 to face the susceptor 16 in parallel. The upper electrode 24 is supported in the chamber 10 through via a cylindrical insulating member 25. The upper electrode 24 has a lower electrode plate 28 provided with a plurality of gas discharge holes 26 and made of, for example, a ceramic, such as an alumina, and an electrode support 30 made of a conductive material, such as an aluminum surface-treated with an alumite. A buffer chamber is formed inside the electrode plate 28 and the electrode support 30, and a gas introduction hole 32 is formed at the upper side of the buffer chamber. Gas supply piping 36 extending from a processing gas supply source 34 is connected to the gas introducing hole 32. A high frequency power supply 38 for supplying high-frequency power to generate plasma is electrically connected to the upper electrode 24 through a matching unit (not shown), and additionally, a Low-Pass Filter (LPF) 42 for passing a high frequency wave applied from the susceptor (lower electrode) 16 is electrically connected to the upper electrode 24.

An exhaust hole 44 is formed in the bottom of the chamber 10, and an exhaust unit 46 is connected to the exhaust hole 44 through an exhaust pipe. This exhaust unit 46 has a vacuum pump such as a turbo molecular pump, and is capable of depressurize a processing space within the chamber 10 to a certain vacuum level. Further, an opening and closing mechanism, e.g., a substrate entrance equipped with a gate valve, is formed in the sidewall of the chamber 10 to allow the substrate W to be put and drawn into and from the chamber 10. The chamber 10 is grounded through an earth wire.

In the plasma processing apparatus, when the substrate W placed on the susceptor 16 is plasma-processed, under the control of a main control unit 20, a predetermined amount of required processing gas is introduced from the processing gas supply unit 34 to the chamber 10 and the pressure of the chamber 10 is adjusted to a set value using the exhaust unit 46. Further, high frequency power at a predetermined frequency (for example, 2 MHz) supplied from the high frequency power supply 18 and high frequency power at a predetermined frequency (for example, 60 MHz) supplied from the high frequency power supply 38 are applied to the susceptor (lower electrode) 16 and the upper electrode 24, respectively. The processing gas discharged from the porous electrode plate or shower head 28 of the upper electrode 24 is converted into plasma during a glow discharge between the electrodes, and the substrate W is plasma processed by radicals or ions contained in the plasma PZ. Furthermore, the distance between the susceptor (lower electrode) 16 and the upper electrode 24 is set to, for example, 10 to 60 mm.

In the present embodiment, a plasma electron density measuring apparatus includes: a cylindrical insulating pipe 50 fixedly attached to the chamber 10; a coaxial cable 52 provided with a probe portion (antenna probe) 52a formed by exposing a core wire of a front end of the coaxial cable 52, and slidabley inserted into one end (left-hand end in FIG. 1) of the insulating pipe 50; a measuring unit 54 for measuring a resonance frequency and electron density through the coaxial cable 52 with respect to the plasma PZ generated in the chamber 10; and a linear actuator 56 for moving the coaxial cable 52 in an axial direction thereof.

The insulating pipe 50 is formed of, for example, a quartz pipe having a straight-line shape, is slightly longer than the outer diameter of the chamber 10, and is open at both ends thereof. As shown in FIG. 1, two through holes 10a facing to each other are formed in the sidewalls of the chamber 10 at center positions between the susceptor (lower electrode) 16 and the upper electrode 24 to be used as supports or measurement ports, and the insulating pipe 50 passes through the through holes 10a and are horizontally positioned across the chamber 10. O-rings 58 are fitted into the through holes 10a to hold the insulating pipe 50 in an airtight manner, that is, a vacuum sealing manner.

The coaxial cable 52, as shown in FIGS. 2A and 2B, is formed of a semi-rigid cable that includes a core wire (inner conductor) 52a made of, e.g., aluminum, an outer conductor 52b made of a stainless pipe, and an insulating member 52c made of Teflon®. The probe portion is formed by exposing the core wire 52a of the front end of the coaxial cable 52 by several mm. A base side of the coaxial cable 52 is connected to the measuring unit 54 in the form of an SMA plug 60 (FIG. 1). Further, the outer conductor (ground portion) 52b of the coaxial cable 52 protruded from the insulating pipe 50 is electrically connected to the sidewall of the chamber 10 having a ground potential via a grounding conductor 62.

As shown in FIG. 2A, the grounding conductor 62 is, e.g., fixedly mounted on a conductive flange member 64, to which the insulating pipe 50 is attached and fixed, at a base thereof, and an front end of the ground conductor 62 may be composed of a plurality of conductive spring members which come into slidable contact with the outer conductor 52b of the coaxial cable 52. Further, the conductive spring members may elastically hold the coaxial cable 52 at a certain location therebetween in a vertical or horizontal direction. Alternately, conductive wires instead of the spring members may be used. In this case, the front ends of the conductive wires may be connected to the outer conductor 52b of the coaxial cable 52 by means of clips. In any case, the probe portion 52a is preferably positioned at a desired location (measurement location) by inserting the coaxial cable 52 into the insulating pipe 50 at the state where the grounding conductor 62 is opened (released) and moving the coaxial cable 52 in the direction of pulling thereof out of the insulating pipe 50.

An electromagnetic wave absorber is provided in the vicinity of and inside the grounding conductor 62, that is, at the location of the probe portion side, to absorb the noise signal of a standing wave generated on the outer conductor 52b of the coaxial cable 52. In the present embodiment, as shown in FIG. 2A, one or more bead-shaped ferrite members 66 are attached to a cylindrical insulating retainer 65 in series in the axial direction of a retainer 65 which the coaxial cable 52 is passed through.

As shown in FIG. 1, the measuring unit 54 includes a vector network analyzer 68 that is a main body of the measuring unit 54, a RF limiter 70 and a HPF 72 used to perform an SMA interface, and a measurement control unit 74 for performing control and operation processes for measurement. The configuration of the vector network analyzer 68 and the measurement control unit 74 will be described later in detail.

The linear actuator 56 includes a slider 76 combined with the base of the coaxial cable 52, and a ball-screw mechanism 78 configured to rectilinearly move the slider 76 in the axial direction of the coaxial cable 52. For example, a servomotor (not shown) may be used as a driving device for the ball-screw mechanism 78, which is adapted to position the slider 76 at a certain location within a moving range of the slider 76.

Piping 82 extending from a cooling gas supply unit 80 is connected to the other end (a right end of FIG. 1) of the insulating pipe 50. The cooling gas supply unit 80 has, e.g., a blower or pump so that cooling gas such as air flows into the insulating pipe 50 through the piping 82. The air introduced into the right end of the insulating pipe 50 flows through the insulating pipe 50 toward the left end of the insulating pipe 50, and is discharged into the atmosphere through the gaps of the grounding conductor 62. As described above, the air flows through the insulating pipe 50 in the axial direction thereof, so that the surrounding of the coaxial cable 52, especially, the probe portion 52a, can be effectively cooled. More preferably, the cooling gas supply unit 80 may supply cooling gas the temperature of which has been adjusted. Alternately, it is possible to construct the cooling gas supply unit 80 in an air suction type, so that the air flows in the insulating pipe 50 from the left side to the right side thereof.

FIG. 3 illustrates principal parts of the vector network analyzer 68 and the measurement control unit 74 of the measurement unit 54.

The vector network analyzer 68 includes a reflection coefficient measuring unit 84 for performing signal transmission/reception and signal processing to measure a reflection coefficient in complex number form (complex reflection coefficient), a buffer memory 86 for temporarily storing temporary data of measured reflection coefficient values (frequency characteristics), and a real part memory 88 and an imaginary part memory 90 for storing respectively the real part $\Gamma_r$ and the imaginary part $\Gamma_I$ of a final data (frequency characteristics) $\Gamma$ of the reflection coefficient measuring unit 84. The reflection coefficient measuring unit 84 includes a frequency sweeping type high frequency power supply, a directional coupler for detecting an incident wave and a reflected wave and a complex reflection coefficient measurement circuit. The complex reflection coefficient measurement circuit may be implemented by employing, e.g., an amplitude ratio measurement circuit and a phase difference measurement circuit.

While a scalar network analyzer obtains a measured value in scalar form from the ratio of the power (scalar) of a reflected wave to the power (scalar) of an incident wave, the vector network analyzer 68 of the present embodiment measures a reflection coefficient $\Gamma(\Gamma_r+j\Gamma_i)$ in complex number form from a ratio $V_{re}/V_{in}$ of voltages $V_{re}$ and $V_{in}$ or a ratio $I_{re}/I_{in}$ of currents $I_{re}$ and $I_{in}$. In this case, an imaginary part $\Gamma_i$ takes a positive or negative sign depending on a frequency.

The measurement control unit 74 includes a resonance frequency determining unit 92 for receiving the measured value data (frequency characteristic) of the imaginary part $\Gamma_i$ of a complex reflection coefficient from the imaginary part memory 90 of the vector network analyzer 68 and determining a resonance frequency $f_p$ by counting zero-crossing points thereof, an electron density operation unit 94 for calculating an electron density $N_e$ using a predetermined calculation equation based on the resonance frequency $f_p$ calculated by the resonance frequency determining unit 92, an output unit 96 for outputting data of the measured electron density $N_e$, and a sequence control unit 98 for controlling a sequence of measurements.

Hereinafter, a method of measuring an electron density of the plasma PZ in the chamber 10 at a specific location in the radial direction of the chamber 10 in the plasma electron density measurement apparatus of the present embodiment is described below.

In the present embodiment, the measurement of a plasma electron density is performed as described below under the control of the coefficient control unit 74 (in particular, a sequence control unit 98) of the measuring unit 54. First, the probe portion 52a is positioned at a desired measurement location $h_k$ by moving the coaxial cable 52 through the insulating pipe 50 along the axial direction thereof (preferably, in the direction of pulling thereof) using the linear actuator 56.

Next, the vector network analyzer 68 obtains a measured value (frequency characteristic) of a complex reflection coefficient $\Gamma$ at the measurement location $h_k$ through the RF limiter 70, the HPF 72, the coaxial cable 52 and the probe portion 52a. In this case, for a reference measurement, at a first measurement step, the frequency characteristic (first frequency characteristic $\Gamma(f)$) of a complex reflection coefficient $\Gamma$ is obtained in a plasma OFF state where the plasma PZ does not exist in the chamber 10, as shown in FIG. 4. Thereafter, at a second measurement step, the frequency characteristic (second frequency characteristic $\Gamma(pf)$) of a complex reflection coefficient $\Gamma$ is obtained in a plasma ON state where the plasma PZ exists in the chamber 10, as shown in FIG. 5.

At the first and second measurement steps, the reflection coefficient measuring unit 84 of the network analyzer 68 transmits an electromagnetic signal (incident wave) of, e.g., about 1 mW to the probe portion 52a of the coaxial cable 52 with respect to each frequency while performing frequency sweeping in a band, e.g., ranging from several hundred MHz to several GHz, so that the electromagnetic signal is irradiated to a surrounding space (along a radial direction when viewed from the probe portion 52a) and is incident on the surrounding plasma PZ. Thereafter, the electromagnetic wave, i.e., a reflected wave, returned from the plasma PZ to the probe portion 52a is received, and the incident wave and the reflected wave are compared with each other using the complex reflection coefficient measurement circuit after being passed through the directional coupler, thus obtaining a measured value of the reflection coefficient $\Gamma(\Gamma_r+j\Gamma_i)$ in complex number form.

Subsequently, a normalized frequency characteristic is obtained from the first frequency characteristic $\Gamma k(f)$ obtained at the first step and the second frequency characteristic $\Gamma k(pf)$ obtained at the second step through a specific operation, for example, division $\Gamma k(pf)/\Gamma k(f)$. Of the measured value (frequency characteristic) of the reflection coefficient $\Gamma(\Gamma_r+j\Gamma_i)$ in complex number form, the real part $\Gamma r$ thereof is stored in the real part memory 88 while the imaginary part $\Gamma_i$ thereof is stored in the imaginary part memory 90. In the present embodiment, the measured value (frequency characteristic) of the complex reflection coefficient $\Gamma_i$ stored in the imaginary part memory 90 is effectively used.

FIG. 6 shows an example (experimental data) of the frequency characteristics of an absolute value $|\Gamma|$, the real part $\Gamma_r$ and the imaginary part $\Gamma_I$ of the reflection coefficient $\Gamma(\Gamma_r+j\Gamma_i)$. This experimental data is obtained at a measurement location R=0 mm (a center point of the chamber) under the plasma cleaning conditions in which the pressure of the chamber 10 is 15 mTorr, lower RF power (2 MHz) supplied from the high frequency power supply 18 is 200 W, upper RF power (60 MHz) supplied from the high frequency power supply 38 is 1500 W, and processing gas is $O_2$ (200 sccm). In FIG. 6, the absolute value $|\Gamma|$ of the reflection coefficient $\Gamma$ corresponds to the reflection coefficient obtained in scalar form by the scalar network analyzer, has a value almost identical with the value of the real part $\Gamma_r$, and does not actually reflect the value of the imaginary part $\Gamma_i$.

Referring to the frequency characteristic of the absolute value $|\Gamma|$ of the complex reflection coefficient $\Gamma$, it is considered that a minimum peak of the absolute value $|\Gamma|$ corresponds to a maximum peak of power absorption attributable to electron oscillations, and the frequency at the time of having the minimum (absorption) peak, that is, plasma absorption frequency, corresponds to an electron frequency. However, if the minimum peak waveform of the absolute value $|\Gamma|$ becomes broad or an amount of a noise component increases, it is difficult to precisely calculate the plasma absorption frequency, so that a measurement error easily occurs. In contrast, in the present invention, based on the waveforms (frequency characteristics) of the imaginary part $\Gamma_i$ of a reflection coefficient $\Gamma$, a frequency at which $\Gamma_r$ is zero-crossing is assumed to be a plasma resonance frequency. Further, the plasma resonance frequency is considered to correspond to a electron frequency, thus being converted into electron density, as will be described below.

In the coefficient control unit 74, the resonance frequency determining unit 92 receives the measured value (frequency characteristic) of the imaginary part $\Gamma_i$ of the complex reflection coefficient from the imaginary part memory 90 of the vector network analyzer 68, and determines a frequency of a zero-crossing point. As described above, the imaginary part $\Gamma_i$ of the complex reflection coefficient has a positive or negative sign depending on the frequency. Generally, in the frequency characteristic of the imaginary part $\Gamma_i$ by frequency sweeping, a zero-crossing point ZC appears at a single point as shown in FIG. 6, $\Gamma_i$ has a negative (minus) value in a frequency domain below the zero-cross point ZC, and $\Gamma_i$ has a positive (plus) value in a frequency domain above the zero-cross point ZC. When viewed from the sweeping direction in which the frequency increases, the value of $\Gamma_i$ changes from a minus value to a plus value at the zero-cross point ZC. On the contrary, when viewed from the sweeping direction in which the frequency decreases, the value of $\Gamma_i$ changes from a plus value to a minus value at the zero-cross point ZC. As described above, the frequency of the zero-cross point ZC is the frequency of the point at which the sign of $\Gamma_i$ is reversed, and can be simply and accurately calculated regardless of the waveform profile of frequency characteristics. In the present invention, the frequency of the zero-cross point is defined as a resonance frequency $f_p$.

Hereinafter, a basic principle of the electron density measuring method is described. The probe portion 52a of the coaxial cable 52 is electrically connected to the plasma PZ in the chamber 10 through the insulating pipe 50. When the complex impedance $Z_p$ of the plasma PZ at the measurement location $h_k$ is set to R+jX and the impedance of the insulating pipe 50 is ignored, the complex reflection coefficient $\Gamma(\Gamma_r+j\Gamma_i)$ is expressed as Equation 2 in terms of impedance.

$$\Gamma = (\Gamma_r + j\Gamma_i) = (Z_p - 50)/(Z_p + 50) \quad \text{Eq. (2)}$$
$$= \{(R+jX) - 50\}/\{(R+jX) + 50\}$$
$$= \{(R-50) + jX\}/\{(R+50) + jX\}$$

The constant "50 (Ω)" of the right side of Equation 2 is the characteristic impedance of the coaxial cable 52. By rationalize Equation 2, Equation 3 can be obtained.

$$\Gamma(\Gamma_r+j\Gamma_i)=(AB+X^2)/(B^2+X^2)+j100X/(B^2+X^2) \quad \text{Eq. (3)}$$

where A=R−50 and B=R+50.

When viewed from the probe portion 52a, the plasma PZ is composed of an ion sheath of a capacitive load that is formed along the surface of the insulating pipe 50 and bulk plasma of an inductive load. The ion sheath has capacitive reactance $X_C$ and the bulk plasma has inductive reactance $X_L$. Both of them form a series circuit between the probe portion 52a and a reference potential (ground potential). When the capacitive reactance $X_C$ of the sheath is higher than the inductive reactance $X_L$ of the bulk plasma, resultant reactance X is minus, and correspondingly, the value of the imaginary part $\Gamma_i$ of the complex reflection coefficient is minus. When the inductive reactance $X_L$ of the bulk plasma is higher than the capacitive reactance $X_C$ of the sheath, resultant reactance X is plus, and correspondingly, the value of the imaginary part $\Gamma_i$ of the complex reflection coefficient is plus. When the capacitive reactance $X_C$ of the sheath is equal to the inductive reactance $X_L$ of the bulk plasma, resultant reactance X is zero, and therefore, series resonance is formed. In this case, the imaginary part $\Gamma_i$ becomes zero. In a series resonant state, signal power transmission attributable to the plasma reactance X is maximized and the energy of an incident wave from the probe portion 52a is transmitted to electrons in the plasma through a so-called Landau damping mechanism. That is, when a series resonance state is established, the frequency of the electromagnetic wave, i.e., the resonance frequency, coincides with or is matched with the electron frequency. In the present invention, in the frequency characteristic of the imaginary part $\Gamma_i$ of the complex reflection coefficient, the frequency at the zero-cross point is considered to be the frequency $f_p$ at which the sheath capacitance and bulk inductance of the plasma resonate in series, and a measured value of the electron density is obtained from a measured value of the resonance frequency $f_p$. In practice, the normalization of the reflection coefficient Γk(pf)/Γk(f) is performed by the vector network analyzer 68 as described above, so that Equation 3 is modified, but basically, the above-described theory is adequate.

In the coefficient control unit 74, the measured value of the resonance frequency $f_p$ obtained from the resonance frequency determining unit 92 is applied to the electron density operation unit 94. Since the resonance frequency $f_p$ propagates through the insulating pipe 50 having a relative permittivity of $\epsilon_r$ at a frequency of $\sqrt{(1+\epsilon_r)}*f_p$, as described above, it can be considered that $\sqrt{(1+\epsilon_r)}*f_p$ is identical with electron frequency $1/2\pi*\sqrt{e^2*N_e/m_e*\epsilon_0}$ in plasma. The electron density operation unit 94 can calculate electron density $N_e$ using Equation 4.

$$N_e = m_e * \varepsilon_0 * (1+\varepsilon_r) * (2\pi f_p/e)^2 \quad \text{Eq. (4)}$$
$$= 5.96\,E10\,(f_p)^2 \ [\text{cm}^{-3}]$$

where $m_e$ is electron mass, $\epsilon_0$ is vacuum, permittivity, $\epsilon_r$ is a relative permittivity of the insulating pipe (about 3.8) and e is elementary electric charge. Furthermore, a unit of $f_p$ is GHz, and E10 designates $10^{10}$.

FIGS. 7A and 7B show an example (experimental data) of the measurement sensitivity of electron density obtained by the plasma resonance probe method of the present invention. This experimental data shows the time variations of electron density $N_e$ immediately after the initiation of plasma ON at measurement locations of R=80 mm (80 mm away from the center point of the chamber in the radial direction of the chamber; FIG. 7A) and R=220 mm (220 mm away from the center point of the chamber in the radial direction of the chamber, 20 mm away from the sidewall of the chamber; FIG. 7B) under the plasma cleaning conditions in which the pressure of the chamber 10 is 15 mTorr, lower RF power (2 MHz) is 200 W, processing gas is $O_2$ (200 sccm) and upper RF power (60 MHz) is minutely varied around 1500 W.

As shown in the drawings, when the upper RF power is varied from the central value 1500 W by ±30 W (2%), at the measurement location of R=80 mm (FIG. 7A), it is read that the electron density $N_e$ is varied by about ±0.1E+10 (E+10=$10^{10}$). Meanwhile, at the measurement location of R=220 mm (FIG. 7B), it is read that the electron density $N_e$ is varied by about ±0.02E+10. In general, in the case where RF power for generating plasma is a process parameter, if the variation of electron density is monitored when the RF power is varied by 2%, it is sufficient in terms of specifications, and the plasma electron density measurement method of the present invention can desirably meet the requirement. It is a noteworthy that the electron density $N_e$ can be measured in high precision even at the measurement location near the sidewall of the chamber where plasma density is low.

In FIG. 8, to compare measurement precisions, the measurement values of electron density $N_e$ obtained by the plasma resonance probe method of the present invention at a measurement location of R=80 mm is compared with those obtained by the plasma absorption probe (PAP) method at the same location. Process conditions are the same as those of the experiments shown in FIGS. 7A and 7B (however, upper RF power is 1500 W). As apparent from FIG. 8, while the variations (waveform) of electron density obtained by the PAP method show large fluctuations in measurement values, the variations (waveform) of electron density obtained by the present invention show small differences in measurement values, and therefore, appear in the form of a smooth curve.

Another advantage of the present invention is the fact that the electron density in the plasma can be accurately measured under a high pressure condition. FIGS. 9, 10 and 11 show the frequency characteristics (experimental data) of complex reflection coefficients when the pressures of the chamber are 15 mTorr, 800 mTorr and 1600 mTorr, respectively. In the drawings, $\Gamma_i$ is the imaginary part of the complex reflection coefficient $\Gamma$ obtained by employing the present invention, and the $|\Gamma|$ is the absolute value of the complex reflection coefficient and corresponds to the reflection coefficient in scalar form, which is obtained by the PAP method. In this experiment, there was used a micro-waveform plasma procession apparatus for plasma chemical vapor deposition (CVD), which created plasma by irradiating microwaves of a high frequency (2.45 GHz) produced by a magnetron, from the quartz window of the ceiling of the chamber through a wave guide into the chamber. The experiment was carried out under process conditions in which gas is Ar (400 sccm) and power of microwaves is 1000 W.

Referring to the frequency characteristics of the absolute value $|\Gamma|$ of the complex reflection coefficient corresponding to the frequency characteristics of the reflection coefficient based on the PAP method, under the condition of a pressure of 15 mTorr (FIG. 9), the minimum (absorption) peak exhibits a shape-angled waveform and a frequency (absorption frequency) corresponding to the peak point can be accurately read. However, under the condition of a pressure of 800 mTorr (FIG. 10), the minimum (absorption) peak waveform is rounded and broadened, a peak point is indefinite and the number of noise components, which may be confused with the minimum peak waveform, increases. Meanwhile, under the condition of a pressure of 1600 mTorr (FIG. 11), this tendency is remarkable and it is difficult to accurately calculate an absorption frequency. The reason for this is that when pressure increases, the number of collisions between electrons and particles in the plasma (in particular, neutral molecules and atoms) increases, so that the amount of power absorption increases accordingly (by actual resistance). As described above, as measurement precision for an absorption frequency becomes lowered, measurement precision for electron density becomes lowered.

In contrast, referring to the frequency characteristics of the reflection coefficient, that is, the frequency characteristics of the imaginary part $\Gamma_i$ of the complex reflection coefficient obtained by the present invention, the points at which the value of $\Gamma_i$ is zero (zero-crossing point) are remarkable at 800 mTorr (FIG. 10) and 1600 mTorr (FIG. 11) as well as 15 mTorr (FIG. 9) and the resonance frequency $f_p$ can be simply and accurately read.

Under the condition of a pressure of 15 mTorr (FIG. 9), the resonance frequency $f_p$ and the electron density calculated at the zero-cross point of the imaginary part $\Gamma_i$ of the complex reflection coefficient are 3700 MHz and $8.19 \times 10^{11}$, respectively, and the absorption frequency and the electron density calculated at the minimum peak of the absolute value $|\Gamma|$ are about 3700 MHz and about $8.19 \times 10^{11}$, respectively. Under the condition of a pressure of 800 mTorr (FIG. 10), the resonance frequency $f_p$ and the corresponding electron density are 2550 MHz and $3.89 \times 10^{11}$, respectively, and the absorption frequency and the corresponding electron density are about 2500 MHz and about $3.73 \times 10^{11}$, respectively. Further, under the condition of a pressure of 1600 mTorr (FIG. 11), the resonance frequency $f_p$ and the corresponding electron density are 2700 MHz and $4.22 \times 10^{11}$, respectively, and the absorption frequency and the corresponding electron density are about 2500 MHz and about $3.81 \times 10^{11}$, respectively.

Meanwhile, when pressure is far lower than 15 mTorr, the size of the gas molecule becomes smaller, and therefore, electron density becomes low. When electron density becomes low, the signal intensity of a reflected wave from plasma is low, an S/N becomes low, and frequency characteristics exhibit a broad tendency. In this case, it is difficult to accurately read an absorption frequency by the PAP method. In contrast, by employing the plasma resonance probe method of the present invention, a resonance frequency $f_p$ can be accurately read based on the zero-cross point of the imaginary part $\Gamma_i$ of a complex reflection coefficient regardless of the waveform of frequency characteristics.

FIG. 12 shows an example (experimental data) of an electron density distribution characteristic obtained under the condition of a high pressure of 2000 mTorr in accordance with the plasma resonance probe method of the present invention. For this experiment, in a capacitively coupled type plasma processing apparatus for plasma CVD, the temperature of a susceptor was 600° C., high-frequency power of 450 kHz and 800 W was applied to an upper (opposite) electrode, and $Ar/H_2$ gas (1600/1000 scm) was used as plasma creation gas. As shown in FIG. 12, it was found that electron density $N_e$ could be measured with high accuracy at respective locations in the radial direction even under the condition of a high pressure of 2000 mTorr.

Further, in the plasma resonance probe method of the present invention, the spatial distribution characteristic of electron density $N_e$ in the radial direction of the chamber 10 can be obtained by moving the location of the probe portion 52a, i.e., the measurement location h, in the insulating pipe 50 in the radial direction in a scanning manner, as shown in FIGS. 4 and 5, and plotting the measurement values of electron density $N_e$ at respective measurement locations $h_1$, $h_2, \ldots, h_n$ on a graph.

In a preferred embodiment of the present invention, the first and second measurement processes can be each performed in batch for all the measurement locations $h_1$, $h_2, \ldots, h_n$. In more detail, in the first measurement process, the frequency characteristics (first frequency characteristics: $\Gamma_1(f), \Gamma_2(f), \ldots, \Gamma_k(f), \ldots, \Gamma_n(f)$) of complex reflection coefficients $\Gamma$ are sequentially obtained at predetermined locations $h_1, h_2, \ldots, h_n$ in the radial direction in the state where plasma PZ does not exist in the chamber 10, as shown in FIG. 4. In this case, the probe portion 52a is moved in steps from the measurement location $h_1$ at the right of the drawing (starting end) to the measurement location $h_n$ at the left of the drawing (terminating end) in such a way that the coaxial cable 52 is intermittently moved by the linear actuator 56 in the direction in which the coaxial cable 52 is pulled out from the insulating pipe 50.

In the second measurement process, the frequency characteristics (second frequency characteristics: $r_1(pf)$, $\Gamma_2(pf), \ldots, \Gamma_k(pf), \ldots, \Gamma_n(pf)$) of complex reflection coefficients $\Gamma$ are sequentially obtained at the locations $h_1$, $h_2, \ldots, h_n$ identical with those of the first measurement process in the radial direction in the state where plasma PZ is created in the chamber 10, as shown in FIG. 5. In this case, the probe portion 52a is moved in steps from the measurement location at the right of the drawing $h_1$ (starting end) to the measurement location $h_n$ at the left of the drawing (terminating end) in such a way that the coaxial cable 52 is intermittently moved by the linear actuator 56 in the direction in which the coaxial cable 52 is pulled out from the insulating pipe 50.

After the first and second frequency characteristics $\Gamma(f)$ and $\Gamma(pf)$ have been obtained respectively in batch, a batch process for all the measurement locations $h_1, h_2, \ldots, h_n$ is performed in each of subsequent signal processing steps, i.e., the normalization of the frequency characteristics Γ(f) and Γ(pf), the extraction of the imaginary part $Γ_i$, and the calculation of the resonance frequency $f_p$ and electron density $N_e$.

As described above, in accordance with the method in which the measurements of the reflection coefficients in a plasma OFF state and a plasma ON state are each performed in batch for the entire locations $h_1, h_2, \ldots, h_n$, the switching of ON and OFF is performed only once regardless of the number of measurement locations, so that the entire measurement efficiency is high, and therefore, measurement time per measurement location can be shortened to several seconds. In contrast, in the conventional PAP method, the ON/OFF of plasma must be repeated whenever a measurement location changes, so that several minutes are required for each measurement location. As the number of measurement locations increases, such a difference in measurement efficiency or measurement time becomes remarkable (in particular, in a large diameter chamber).

In the present embodiment, the insulating pipe 50 is hung between a pair of supports (through holes 10a) provided at opposite locations on the sidewalls of the chamber 10, and is airtightly secured by the O-rings 58. The positioning of the probe portion 52a is performed by moving the coaxial cable 52 in the insulating pipe 50, which is horizontally fixed like a bridge, in the axial direction. In this way, the probe portion 52a can be rapidly and accurately positioned at desired locations and be placed on a horizontal line, so that the reproducibility of measurement locations can be assured.

Further, since there is no friction between the insulating pipe 50 and the O-rings 58, the stability of the probe mechanism is increased and costs of consumables (CoC) is improved without the damage and deterioration of the O-rings 58. Furthermore, the influence (disturbance) of the probe mechanism on plasma is constant regardless of a measurement location, and reliability on measurement precision is improved because disturbance time (measurement time) is very short.

Furthermore, the insulating pipe 50 has a coaxial pipe structure that is constant or uniform at any location when viewed from the probe portion 52a of the coaxial cable 52. Since the coupling of an electromagnetic wave, which is generated from the probe portion 52a, with plasma is constant, noise is hardly generated, so that measurement with high precision and reproducibility can be performed. The bead-shaped ferrite members 66 as an electromagnetic wave absorber are mounted around the coaxial cable 52, so that, even when standing wave noise is generated on the outer conductor (ground portion) 52b of the coaxial cable 52, it can be sufficiently eliminated through the effective absorption of the standing wave noise by the bead-shaped ferrite members 66.

Further, in the plasma electron density measurement apparatus, the outer conductor (ground portion) 52b of the coaxial cable 52 is grounded through the grounding conductor 62 and the chamber 10. By employing this RF shield function using the chamber 10, the leakage of the RF noise to the atmosphere or the measuring circuit 54 is effectively prevented, so that safety for the human body or measurement equipment can be assured and the malfunction of surrounding electronic equipment, such as a gas detector, can be avoided.

Furthermore, since, through the use of this RF shield function, noise signals propagate on the outer conductor (grounding portion) 52b of the coaxial cable 52 at an inner area (probe portion 52b side) when viewed from a location where the outer conductor 52b is connected with the grounding conductor 62 or a short circuit point A, the bead-shaped ferrite members 66 for absorbing standing wave noise are preferably arranged at a point inner than the short circuit point A. More preferably, like the present embodiment, the bead-shaped ferrite members 66 may be arranged near the short circuit point A, which is the abdominal portion of the standing wave noise, as much as possible.

In the present embodiment, the coaxial cable 52 is effectively cooled by opening the front end side of the insulating pipe 50, i.e., the side of the insulating pipe 50 opposite to the probe portion 52a, and flowing air into the opening from the cooling gas supply unit 80, so that thermal expansion and thermal deterioration around the probe portion 52a can be prevented, thus improving the durability thereof.

The plasma electron density measurement method and apparatus of the present embodiment allow reliable plasma electron density measurement to be easily, efficiently and rapidly performed even by using a 300 mm wafer or FPD processing apparatus having a large diameter chamber.

Furthermore, since the present invention enables electron density to be accurately measured even at a place where plasma density is low, as described above, the monitoring of plasma can be performed at a measurement location that the plasma is not disturbed. FIG. 13 shows an embodiment of the present invention that enables no-disturbance plasma monitoring. In this drawing, elements having same configurations and functions as those of FIG. 1 are designated by same numerals.

As shown in FIG. 13, in the plasma electron density measuring apparatus of the present embodiment, probe units 100, 102 and 104 are embedded at three locations, i.e., in the sidewall of the chamber 10, the central portion of the upper electrode 24 and the peripheral portion of the lower electrode 16. All of the probe units are arranged around the plasma region, so that electron density thereback can be measured without the disturbance of the plasma PZ.

FIGS. 14A and 14B show examples of a probe unit 100 embedded in the sidewall of the chamber. The configuration of FIG. 14A is formed by closing the front end of the insulating pipe 50 of the above embodiment (FIG. 1) and somewhat projecting the insulating pipe 50 from the sidewall of the chamber 10 toward the plasma region. To improve the directionality of radiation toward the front of the probe portion 52a (plasma region), it is preferable to attach the front of the probe portion 52a to the front end of the insulating pipe 50.

The configuration of FIG. 14B is formed by bringing a cylindrical housing 106 made of insulator to be leveled with or lower than the inner surface of the sidewall of the chamber 10. It is preferable, for the improvement of measurement sensitivity, to provide a window member 108, which is made of a high-permittivity material such as sapphire and is small in plate thickness, in the front portion of the housing 106. Furthermore, as shown in this drawing, the discontinuous point of impedance may be formed in the probe portion 52a by bending the front of the probe portion 52a in an L shape, such that a wave can be efficiently irradiated from the discontinuous point to the front thereof.

Additionally, to improve front directionality, it is possible to attach a disk-shaped capacitive coupling member 110 to the front of the probe portion 52a, as shown in FIG. 15B, and to attached a cross-shaped inductive antenna member 112 to the front of the probe portion 52a, as shown in FIG. 15D. Furthermore, the probe configuration of FIG. 15A is adopted by the probe unit 100 of FIG. 14A, and the probe configuration of FIG. 15C is adopted by the probe unit 100 of FIG.

14B. The probe units 102 and 104 around the electrode may have the same configuration and function as the probe unit 100.

In FIG. 13, the respective probe units 100, 102 and 104 are connected to a network analyzer 68 through the selection switch 114. During plasma processing, the selection switch 114 is switched to the respective probe units 100, 102 and 104 in a time division manner under the control of the measurement control unit 74, so that the simultaneous measurement of plasma density in the chamber 10 at a plurality of monitoring locations can be efficiently performed using a single measuring unit 54. Further, the variations of plasma electron density or the actual situation of the process can be simply monitored at a location around the plasma PZ without disturbing the plasma PZ in the chamber 10 during the process. It is possible to feed back measurement results to a current process condition or next process condition by transferring information monitored by the measuring unit 54 to a main control unit 20. As representative parameters to monitor the plasma processing, there are pressure, RF power, a gas flow rate, temperature, etc.

In an embodiment shown in FIG. 16, a plasma processing system is composed of a plurality of plasma processing apparatuses in accordance with the embodiment of FIG. 13. As shown in this drawing, probe units 116 and 118 embedded in two (three or more are possible) plasma processing apparatuses, respectively, can be connected to a common vector network analyzer 68 in a time division manner through the use of a selection switch 114. In this system, it is possible to feed back measurement results to a current process condition or next process condition of the respective processing apparatuses by transferring information monitored by the respective processing apparatuses from the measuring unit 54 to the process control units 20. If the plurality of plasma processing apparatuses are of the same type, it can be determined whether there exists any difference between the processing apparatuses.

An application to which the embodiment of FIG. 13 can be applied is a seasoning. As well known to those skilled in the art, the seasoning is a process of repeating a plasma etching cycle (pilot operation) an appropriate number of times using a dummy wafer so as to stabilize the inside of the chamber to be suitable for the atmosphere of processing conditions after the cleaning of the chamber or the replacement of parts. In general, immediately after the cleaning of a chamber or displacement of a part, the attachment of deposits from a plasma space to the inner wall of the chamber is greater than the discharge of deposits from the inner wall of the chamber to the plasma space, so that processing is not stabilized. While the plasma processing cycle is being repeated several number of times, the attachment and discharge of deposits are balanced, thus stabilizing the processing.

Conventionally, an etching rate is monitored in each processing cycle under standard recipe conditions, the number of dummy wafers (or the number of pilot cycles and pilot operation time) required until the etching rate is stabilized is determined as a seasoning condition, and the seasoning condition is fixed and applied to every processing recipe. However, as well known in the art, the fixed seasoning condition is not appropriate for every processing recipe, and may be excessive or insufficient for some processing recipes. That is, if the seasoning condition is excessive, an unnecessary etching cycle is performed, to thereby cause a reduction in throughput. In other words, if the seasoning condition is insufficient, unstable processing is performed on a normal wafer, thus causing a reduction in yield. Further, though a method of setting seasoning conditions based on the experience and feeling of a process engineer or operator is being performed, certainty and universality are low, and therefore, the above-mentioned problems may arise. In accordance with the present invention, as described below, adaptive seasoning control is performed for each processing recipe, so that tradeoff between the improvements of throughput and yield can be solved.

In accordance with the plasma resonance probe method of the present invention, electron density can be accurately measured even in the space where plasma density is low, so that electron density can be monitored during an actual process without disturbing the plasma, e.g., by placing the probe unit 100 in the sidewall of the chamber 10, as described above. After the cleaning of the chamber or the replacement of parts in actual processing, such as plasma etching, an etching rate is highest in an initial etching cycle (first wafer), the etching rate gradually decreases, while the etching cycle is being repeated, and is finally stabilized after specific cycles. FIG. 17 shows an example in which an etching rate is gradually decreased and, thus, stabilized at respective locations on a wafer in the etching cycles of seasoning. The illustrated example shows a result of a silicon dioxide film etching process, and its basic etching conditions are as follows:

wafer diameter: 200 mm
gas pressure: 15 mTorr
distance between upper and lower electrodes: 25 mm
etching gas: $C_5F_8/O_2/Ar$=15/380/19 sccm
RF power: upper/lower=2170/1550 W As shown in FIG. 17, an etching rate E/R changes (decreases) considerably between a first wafer No. 1 and a third wafer No. 3, changes (decreases) still considerably between the third wafer No. 3 and a fifth wafer No. 5, and changes little (decreases) between the fifth wafer No. 5 to a seventh wafer No. 7. In this example, it can be considered that seasoning has been completed at the time of processing the fifth wafer No. 5. Meanwhile, as for the surface of a wafer, the etching rate E/R changes most considerably on the center portion of the wafer, and the etching rate E/R changes meaningfully on the edge portion of the wafer.

FIG. 18 shows a situation in which the average value of an etching rate on a wafer (Ave. E/R) decreases gradually and is stabilized while the first to seventh wafer are being processed, and the time variations of electron density $N_e$ in respective etching cycles. In this case, the electron density $N_e$ was monitored by employing the plasma resonance probe method in the vicinity of the sidewall of the chamber (10 mm away from the sidewall of the chamber), and 15 pieces of measurement data are plotted at four-second intervals during each etching cycle [TA=60 seconds]. The average value of the etching rate E/R is normalized based on reference values obtained by processing the first wafer No. 1, and the electron density $N_e$ is normalized based on the average value of the values obtained by processing the first wafer No. 1.

As shown in FIG. 18, in the seasoning, it can be appreciated that there is a relationship between the variations of the etching rate E/R corresponding to etching cycles and those of the electron density $N_e$. That is, as the number of etching cycles increases to 1, 2, 3, ..., a maximum value (a value at the initiation of a cycle), a minimum value (a value at the termination of a cycle) and an average value of the electron density $N_e$ gradually decrease in each etching cycle in conjunction with the gradual decrease of the average value of the etching rates E/R. Subsequently, as the average value of the etching rates E/R is stabilized, the maximum value, minimum value and average value of electron density $N_e$ are also stabilized.

In accordance with the present invention, after the cleaning and part displacement in chamber 10, the representative measured values (maximum value, minimum value and average value) of time-varying electron density $N_e$ can be monitored with high precision in the vicinity of the sidewall of the chamber 10 in each etching cycle with respect to each of dummy wafers, which are loaded into the chamber 10 and subject to plasma etching, without influence on an actual processing. Subsequently, when the representative values are stabilized to actual normal values between two continuous processing steps of dummy wafers, seasoning is finished. At this time, a substrate to be put into the chamber 10 and be processed is changed from a dummy wafer to a normal wafer.

In the above-described embodiment, the frequency characteristic of an imaginary part $\Gamma_i$ is obtained from the complex reflection coefficient $\Gamma$ in the vector network analyzer 68 of the measurement unit 54, and a resonance frequency $f_p$ is read at the zero-crossing point of the imaginary part $\Gamma_i$. In a modified embodiment, the phase difference between incident and reflected waves is measured in the vector network analyzer 68, and a resonance frequency $f_p$ may be set to a frequency at the zero-crossing point of the frequency characteristic of the phase difference. That is, since the sign of the phase difference between the incident and reflected waves measured by the vector network analyzer 68 corresponds to that of the imaginary part $\Gamma_i$ of the complex reflection coefficient, a frequency at which the phase difference becomes zero can be considered as a frequency at which the imaginary part $\Gamma_i$ of the complex reflection coefficient becomes zero, that is, the resonance frequency $f_p$. Accordingly, a high precision measured value of electron density can be obtained from the resonance frequency $f_p$ calculated from the phase difference.

Further, in the above-described embodiment, the probe portion 52a of the coaxial cable 52 is sequentially positioned at respective measurement positions $h_i$ in the insulating pipe 50 by intermittently moving the probe portion 52a in steps. However, it is possible that a location sensor, such as a rotary encoder or linear encoder, is mounted on the linear actuator 54 to detect a current location of the slider portion 76 or probe portion 52a, so that the frequency characteristics of reflection coefficients can be obtained by activating the network analyzer 68 when the probe portion 52a passes through the respective measurement locations $h_k$ while continuously moving with uniform velocity the coaxial cable 52 in the axial direction. It is also possible to limit the measurement positions $h_k$ to a single location in the chamber 10.

In the above-described embodiment, the insulating pipe 50 accommodating the probe portion 52a of the coaxial cable 52 is horizontally hung between a pair of supports (through holes 10a) provided at opposite locations on the sidewalls of the chamber 10. However, the plasma resonance probe method of the present invention can be applied to a cantilever scheme where the insulating pipe 50 is supported with the front end thereof being suspended in space. The actuator 56 of the above-described embodiment is of a type in which a rotational driving force of an electric motor is converted into a rectilinear driving force by a ball-screw mechanism. However, the actuator used in the present invention is not limited to such a motor-type driving device, but may be any driving device such as a pneumatic type or magnetic type device.

Next, with reference to FIGS. 19 to 31, an embodiment of the PAP method of the present invention is described. In FIG. 19, a configuration of a plasma electron density measurement method and apparatus in accordance with a second embodiment of the present invention is illustrated. In these drawings, elements having same configurations and functions as those in the plasma processing apparatus and plasma monitoring apparatus of FIG. 1 are assigned the same reference numerals, and detailed descriptions thereof are omitted.

In the second embodiment, a measuring unit 54 of a plasma density measuring apparatus includes a scalar network analyzer 120 and a measurement control unit 122 to carry out the PAP method.

The scalar network analyzer 120 transmits an electromagnetic signal (incident wave) having minute power to a probe portion 52a of a coaxial cable 52 with respect to each frequency while performing frequency sweeping in a band ranging from several hundred MHz to several GHz to be irradiated to plasma PZ in a chamber 10, obtains a scalar reflection coefficient based on the ratio of the amount of the power of a electromagnetic wave (reflected wave) reflected from the plasma PZ to the amount of the power of an incident wave, and thus obtains the frequency characteristic thereof. The measurement control unit 122 is adapted to perform control and calculation process for measurement. In particular, the measurement control unit 122 obtains the frequency characteristic of a scalar reflection coefficient obtained by the scalar network analyzer 120, calculates the minimum peak or absorption peak of a waveform of the frequency characteristic, and obtains a frequency corresponding to the absorption peak, that is, a plasma absorption frequency.

Now, with reference to FIGS. 20 to 22, a method of measuring a plasma absorption frequency and electron density in the plasma monitoring apparatus of the present embodiment is described. As shown in FIG. 20, the plasma monitoring of the present embodiment is divided into three steps, including setting, batch measurement and batch data processing.

At the setting step (step S1), in the measurement control unit 122, parameters related to monitoring (for example, RF power, pressure, gas species, distance between electrodes, and a configuration of the electrodes) or measurement locations are set and input. For the measurement locations, the data of respective locations may be directly set and input. Alternatively, the measurement locations may be calculated based on the set and input values of the location of an origin, and the number of measurement locations or pitch (interval between the measurement locations).

The batch measurement step includes a first batch measurement step (step S2) of obtaining the frequency characteristics (first frequency characteristics) of reflection coefficients in batch for all the measurement locations in a plasma OFF state where there is no plasma PZ in the chamber 10, and a second batch measurement step (step S3) of obtaining frequency characteristics of reflection coefficients (second frequency characteristics) in batch for all the measurement locations in a plasma ON state where there exists plasma PZ in the chamber 10.

In FIG. 21, the detailed sequence of the first batch measurement step (step S2) is shown. In this first batch measurement step, first, it is determined whether the plasma PZ does not exist in the chamber 10 (steps A1 and A2). From an apparatus point of view, the state without plasma PZ, that is, the plasma OFF state, can be initiated in such a way that high frequency power supplies 18 and 38 stop the output of high frequency power and a processing gas supply unit 34 stops the supply of processing gas. Furthermore, the pressure of the chamber 10 is maintained at a certain vacuum degree.

As described above, in the state where the plasma PZ does not exist in the chamber 10, the frequency characteristics of reflection coefficients (first frequency characteristics) are sequentially obtained for preset measurement locations $h_1$, $h_2, \ldots, h_i, \ldots, h_{n-1}, h_n$ in the radial direction of the chamber. In more detail, like the first embodiment (FIG. 1), a probe portion 52a is positioned at a target measurement location $h_i$ (step A3), an electromagnetic signal (examination wave or incident wave) of, e.g., 1 mW is sent from the scalar network analyzer 52a to the probe portion 52a of the coaxial cable 52 and irradiated to surroundings (mainly, in the radial direction when viewed from the probe portion 52a) while performing frequency sweeping in a band, e.g., ranging from several hundred MHz to several GHz. Then, a scalar reflectance or reflection coefficient is obtained from the ratio of the amount of the power of a signal reflected to the scalar network analyzer 120 to the amount of the power of the incident wave. The frequency characteristic Γi(f) (parameter S11) of the reflection coefficient obtained or displayed by the scalar network analyzer 120 is stored in a memory in the measurement control unit 122 (steps A4 and A5). Subsequently, the probe portion 52a is moved to the next measurement location $h_{i+1}$ (step A6→A7→A8→A3), the frequency characteristic Γi+1(f) (parameter S11) of a reflection coefficient is obtained by signal processing as described above (step A4), and the obtained frequency characteristic is stored in the memory in the measurement control unit 122 as measured data (step A5). The above-described series of steps (steps A3, A4 and A5) are repeated for all the measurement locations $h_1, h_2, \ldots, h_i, \ldots, h_{n-1}, h_n$ (steps A6, A7 and A8).

In the present embodiment, by sequentially moving the probe portion 52a in steps from the measurement location $h_1$ at the right-hand end (initiation end) of the drawing to the measurement location $h_n$ (termination end) at the left-hand end thereof by intermittently moving the coaxial cable 52 through the use of a linear actuator 56 in the direction in which the coaxial cable 52 is pulled out from the insulating pipe 50, as shown in FIG. 4, the series of steps (steps A3, A4 and A5) can be efficiently performed in a short time (within a tact time of several seconds).

In FIG. 22, a detailed sequence in the second batch measurement step (step S3) is shown. In the second batch measurement step, desired plasma PZ is created in the chamber 10 first (step B1). From an apparatus point of view, the state where the plasma PZ exists, that is, a plasma ON state, can be initiated in such a way that the high frequency power supplies 18 and 38 apply high frequency power to both electrodes 16 and 24 at preset RF power and the processing gas supply unit 34 supplies desired processing gas into the chamber 10.

As described above, in the state where the plasma PZ is being created in the chamber 10, the frequency characteristics of reflection coefficients (second frequency characteristics) are sequentially obtained at the same measurement locations $h_1, h_2, \ldots, h_i, \ldots, h_{n-1}, h_n$ as the first batch measurement step. In more detail, according to the same sequence and signal processing as described above, the probe portion 52a of the coaxial cable 52 is sequentially positioned at respective measurement locations $h_i$ by the linear actuator 56 (step B2), the frequency characteristics Γi(pf) of the reflection coefficients are obtained by the scalar network analyzer 120 for the respective measurement locations $h_i$, and the obtained frequency characteristic is stored in the memory in the measurement control unit 122 as measured data (step B4). Such a series of steps (steps B2, B3 and B4) are repeated for all the measurement locations $h_1$, $h_2, \ldots, h_i, \ldots, h_{n-1}, h_n$ (steps B5, B6 and B7).

In the second batch measurement step, as shown in FIG. 5, by sequentially moving the probe portion 52a in steps from the measurement location $h_1$ at the right-hand end (initiation end) of the drawing to the measurement location $h_n$ (termination end) at the left-hand end thereof by intermittently moving the coaxial cable 52 through the use of the linear actuator 56 in the direction in which the coaxial cable 52 is pulled out from the insulating pipe 50, the series of steps (steps B2, B3 and B4) can be efficiently performed within a tact time of several seconds.

As for the coaxial cable 52, since an outer conductor 52b is a stainless steel pipe having superior rigidity, stable linearity can be maintained while the coaxial cable 52 is being pulled out from the insulating pipe 50. Further, the thermal expansion and rupture of an insulating member 52c can be prevented in the high temperature atmosphere of plasma PZ.

In FIG. 20, the batch data processing step includes a first data processing step (step S4) of calculating in batch plasma absorption frequencies from the first and second frequency characteristics Γ(f) and Γ(pf) of the reflection coefficients obtained at the batch measurement step for all the measurement locations $h_1, h_2, \ldots, h_n$ through a certain operation (for example, division or subtraction), and a second data processing step (step S5) of calculating in batch plasma electron density through the operation according to Equation 1 based on the measurement values of the plasma absorption frequencies.

In more detail, in the first data processing step (step S4), the ratio Γi(pf)/Γi(f) of the second frequency characteristic Γi(pf) to the first frequency characteristic Γi(f) is calculated for each of the measurement locations $h_1, h_2, \ldots, h_{n-1}, h_n$. The ratio Γi(pf)/Γi(f) indicates the frequency characteristics of energy absorption by plasma in a vacuum state. Strictly speaking an electromagnetic wave irradiated from the probe portion 52a propagates along the surface of the insulating pipe 50, and the absorption of the surface wave occurs when the frequency of the surface wave coincides with the number of electron oscillations $f_p$ of the plasma, so that reflectance is extremely reduced. Accordingly, a frequency at a point of time when the ratio Γi(pf)/Γi(f) forms a minimum peak is calculated, which can be used as a measured value of the plasma absorption frequency.

In the second data processing step (step S5), the measured values of electron density $N_e$ are obtained for the respective measurement locations $h_1, h_2, \ldots, h_{n-1}, h_n$ by employing Equation 1 based on the measured values of plasma absorption frequencies. By plotting the measured values of the electron density $N_e$ on a graph to correspond to the respective measurement locations, the spatial distribution of electron density $N_e$ in the radial direction of the plasma PZ can be examined.

FIG. 23 shows an example (embodiment) of the spatial distribution characteristics of electron density $N_e$ obtained in the plasma monitoring apparatus of the present embodiment together with a comparative example. In this case, the comparative example is the spatial distribution characteristics of electron density $N_e$ that are obtained in such a way as to measure the first and second frequency characteristics Γi(f) and Γi(fp) of reflected waves while switching a plasma OFF state to a plasma ON state and vice versa at the respective measurement locations $h_i$ in the apparatus of FIG. 19.

As shown in the drawing, in the embodiment and comparative example, there is no great difference between the spatial distribution characteristics of electron density $N_e$. However, since the comparative example is based on the method of measuring reflection coefficients whenever a plasma OFF state is switched to a plasma ON state and vice versa at respective measurement locations, and ON/OFF switching time is consumed in proportion to the number of measurement locations, the entire measurement efficiency is low, so that a measurement time of several seconds is required for each measurement location. In contrast, since the embodiment is based on the method of performing each of the measurements of reflection coefficients in a plasma OFF state and a plasma ON state in batch for all the measurement locations $h_1$ to $h_n$, and performs ON/OFF switching only once regardless of the number of measurement locations, the entire measurement efficiency is high, so that measurement time for each measurement location can be shortened to less than several seconds. Accordingly, in the example of FIG. 23 (where the number of measurement points is 16), it takes a total measurement time of about 30 minutes in the comparative example, while the measurement could be finished within about 3 minutes in the embodiment. This difference in measurement efficiency or time becomes remarkable as the number of measurement points are increased.

As described above, by employing the plasma monitoring apparatus of the present embodiment, it is possible to efficiently measure plasma absorption frequencies or electron density in a short time, and it is also possible to easily and efficiently perform highly reliable plasma monitoring in a short time even when using a 300 mm wafer or FPD processing apparatus with a large diameter chamber.

Further, in an actual manufacturing process that a plasma processing apparatus in accordance with the present embodiment performs, it is desirable to remove a probe mechanism (an insulating pipe and a coaxial cable) from the processing apparatus. In the present embodiment, the through hole 10a of the chamber 10, which is opened when the insulating pipe 50 is pulled out, may be vacuum-sealed by closing the through hole 10a with a sealing member such as a plug.

In the following, a specific example of the second embodiment will be described.

In the plasma processing apparatus (FIG. 19), the RF frequencies of upper and lower frequency power (high frequency power supplies 38 and 18) were set to 60 MHz and 2 MHz, respectively, and the interval (gap) between the upper electrode 24 and the lower electrode (susceptor) 16 was set to 25 mm.

In the plasma monitoring apparatus of the embodiment, as for the insulating pipe 50, a transparent quartz pipe of 550 mm in total length, 3 mm in outer diameter and 1.5 mm in inner diameter was used. Further, the height at which the insulating pipe 50 is hung between both through holes 10a of the sidewalls of the chamber 10 was set to a location 10 mm away from the upper electrode 24 and 15 mm away from the lower electrode 16. As for the coaxial cable 52, a semi-rigid cable SC-086/50 (a product of Coax company) of 0.20 mm in the outer diameter of a core wire (inner conductor) 52a, 0.86 mm in the outer diameter of an outer conductor 52b and a characteristic impedance of 50 Ω was used. Further, the probe portion was formed by exposing a portion of the core wire 52a at the front end thereof to which Teflon® is attached. As for the measuring circuit 54, a high pass filter of Japanese High Frequency company was used as the HPF 72, 11930B of Agilent Technology company was used as the RF limiter 70, and HP8753ET of Agilent Technology company was used as the scalar network analyzer 120. The scalar network analyzer 120 was set to sweep and output high frequency signals (0 dBm: 1 mW) in a band ranging from 150 to 2500 MHz at every 600 msec. A linear actuator LCA40 of THK company was used as the linear actuator 56.

In the plasma absorption probe method of the embodiment, the grounding line 52b of the coaxial cable 52 is short-circuited and grounded to the housing (sidewall) of the chamber 10 so as to cope with an RF leakage. However, in a configuration without the bead-type ferrite member 66, when the insertion length L of the coaxial cable 52 into the chamber 10 (distance between the short-circuited point A and the front end of the probe portion 52a) was changed, there was a phenomenon in which peaks, which were considered noise other than a plasma absorption frequency, were periodically generated.

To clarify the mechanism of the noise generation, the insertion length L (FIG. 2) of the coaxial cable 52 was changed and the frequency characteristics of noise peaks obtained at this time were investigated. FIG. 24 shows these frequency characteristics. It can be appreciated from FIG. 24 that noise peaks are periodically generated in a band above 1500 MHz in accordance with the insertion length L of the coaxial cable 52. Further, the plasma frequency $f_p$ exists in a range ranging from 1000 MHz to 1500 MHz.

In FIG. 25, the frequencies (measured values) of noise peaks are represented by points, while resonance frequencies (calculated values of peak frequencies) determined by the insertion lengths L are represented by curves. In FIG. 25, λ represents a wavelength of a noise signal propagating along the outer conductor 52b of the coaxial cable 52, and λg represents a wavelength of a noise signal propagating along the core wire (inner conductor 52a). It can be found from the graph of FIG. 25 that the measured values of noise peaks almost completely coincide with the calculated values thereof (integer times a half wavelength).

It is appreciated from these results that standing waves are generated by the grounding line 52b of the inserted coaxial cable 52, these standing waves are recognized as signals by the probe portion, and standing wave noise peaks other than absorption peaks attributable to plasma are generated. If such standing waves are generated, the S/N of the frequency characteristics of plasma absorption is deteriorated and may be erroneously considered as plasma absorption peaks.

Accordingly, as in the above-described embodiment, experiments on the absorption of standing wave noise using an electromagnetic wave absorber 66 were carried out. A bead ferrite HF70BB3.5×5×1.3 of TDK company was used as the electromagnetic wave absorber 66. Further, for the plasma creation conditions in the plasma processing apparatus, $C_5F_8/Ar/O_2$ mixed gas (flow rate: 15/380/19 sccm) was used as processing gas, the pressure of the chamber 10 was set to 2.0 Pa (15 mTorr), upper/lower high frequency powers were 2.17/1.55 kW, respectively, and the temperatures of an upper electrode/sidewall of chamber/lower electrode were set to 60/50/20° C., respectively. Two points where R=0 (wafer center) and R=160 mm were selected as measurement locations, where R is the distance from the center of a wafer.

FIGS. 26A and 26B show data on the results of these experiments. As can be known from the results of these experiments, it were clearly ascertained that standing wave noise could be effectively eliminated without influence on original plasma absorption peaks by mounting the electromagnetic wave absorber 66 on the coaxial cable 52.

Next, noise reduction effect under plasma cleaning conditions was estimated by experiments. The purpose thereof is to ascertain whether standing wave noise can be effectively reduced by the electromagnetic wave absorber 66 under the conditions in which electron density is reduced and S/N is deteriorated like in the plasma cleaning conditions. Herein, the plasma cleaning means a cleaning method of eliminating reaction residues attached to the inner wall of the chamber etc. by using plasma.

For the plasma creation conditions in the plasma processing apparatus, $O_2$ was used as the processing gas, the flow rate of supply thereof was set to 200 sccm, the pressure of the chamber 10 was set to 2.0 Pa (15 mTorr), lower power was set to 200 W, the temperatures of an upper electrode/sidewall of chamber/lower electrode were 30/50/20° C., respectively, and the lower power was changed from 1500 W to 200 W. The measurement location was set to a location where R=0 (wafer center).

FIG. 27 shows the results of these experiments. It could be also appreciated that, since only standing wave noise could be selectively eliminated, plasma absorption peak could be detected even when it is a weak signal.

Further, the variations of a signal were estimated when the electromagnetic wave absorber 66 mounted on the coaxial cable 52 was enhanced. Specifically, the signals (depths) of plasma absorption peaks, which were obtained when the number of bead ferrites (HF70BB3.5×5×1.3) arranged in series to the coaxial cable 52 was increased to 5, 10 and 15, respectively, were compared with each other. As a result, as shown in FIG. 28, it was found that signals increases as the number of bead ferrites increases. It is considered that the reason for this is that the ferrites eliminate noise components contained in the signals through electromagnetic induction. However, if an electromagnetic wave is absorbed by a ferrite, the electromagnetic wave is converted into thermal energy, so that the ferrite itself is heated. When the temperature of the ferrite exceeds the Curie point (Tc: about 100° C.), the ferrite loses the characteristic of electromagnetic wave absorption. Accordingly, it is preferable to cool the ferrite. In this embodiment, the electromagnetic wave absorber 66 is air-cooled by the cooling gas supply unit 80.

Further, a relationship between pressure and the spatial distribution of electron density was investigated for several processing plasmas as follows.

(1) The spatial distribution of electron density along the radial direction of the chamber was investigated for etching plasma used to form a connection hole having a high aspect ratio, with pressure being used as a parameter. FIG. 29 shows results thereof. The basic plasma creation conditions (recipe) were as follows:
  wafer diameter: 200 mm
  etching gas: $C_5F_8/Ar/O_2$ mixed gas
  gas flow rate: $C_5F_8/Ar/O_2$=15/380/19 sccm
  gas pressure: 2.0~26.6 Pa (15~200 mTorr)
  RF power: upper/lower=2.17/1.55 kW
  set temperature: upper electrode/sidewall/lower electrode=60/50/20° C.
  amplitudes of lower RF voltages: 1385 V (2.0 Pa), 1345 V (4.0 Pa), 1355 V (10.6 Pa), 1370 V (16.0 Pa), 1380 V (26.6 Pa)

As shown in FIG. 29, it can be found that, under these plasma creation conditions, if the pressure exceeds 16.0 Pa (120 mTorr), electron density $N_e$ decreases at a location around the center of a wafer, so that uniformity is lost.

(2) The spatial distribution of electron density along the radial direction of the chamber was investigated for etching plasma used to form a wiring groove (trench) on a Si substrate, with pressure being used as a parameter. FIG. 30 shows results thereof. The basic plasma creation conditions (recipe) were as follows:
  wafer diameter: 200 mm
  etching gas: $CF_4/O_2$ mixed gas
  gas flow rate: $CF_4/O_2$=40/3 sccm
  gas pressure: 6.7~66.5 Pa (50~500 mTorr)
  RF power: upper/lower=1.0/1.2 kW
  set temperature: upper electrode/sidewall/lower electrode=60/50/20° C.
  amplitudes of lower RF voltages: 1530 V(6.7 Pa), 1690 V (20.0 Pa), 1400 V (39.9 Pa), 1180 V (66.5 Pa)

As shown in FIG. 30, it can be found that, under these plasma creation conditions, electron density $N_e$ has a non-uniform distribution at a gas pressure of 6.7 Pa or 20.0 Pa but a uniform distribution at a pressure above 39.9 Pa.

(3) The spatial distribution of electron density along the radial direction of the chamber was investigated for etching plasma used to form a via hole in an interlayer insulating film on a substrate, with pressure being used as a parameter. FIG. 31 shows results thereof. The basic plasma creation conditions (recipe) were as follows:
  wafer diameter: 200 mm
  etching gas: $N_2$ gas
  gas flow rate: 300 sccm
  gas pressure: 53.2~106.4 Pa (400~800 mTorr)
  RF power: upper/lower=1.5/1.0 kW
  set temperature: upper electrode/sidewall/lower electrode=30/50/20° C.
  amplitudes of lower RF voltages: 1015 V (53.2 Pa), 938 V (106.4 Pa)

As shown in FIG. 31, it can be found that, under these plasma creation conditions, the uniformity of electron density $N_e$ can be maintained even when gas pressure is increased to 106.4 Pa.

As described above, in the plasma monitoring method and apparatus of the present embodiment, the measurement of high precision electron density can be performed over a wide range of low pressure to high pressure in a short time. Accordingly, the plasma processing apparatus of the present embodiment optimizes a recipe so that plasma density, i.e., electron density, are uniformly distributed in a processing space under desired processing conditions, thus assuring the in-surface uniformity of plasma processing and improving yields.

Furthermore, in the second embodiment, various modifications are possible as in the first embodiment.

EMBODIMENT 3

Next, with reference to FIGS. 32 to 48, an embodiment of the plasma light emission measuring method of the present invention is described. FIG. 32 shows a configuration of a plasma processing apparatus to which plasma light emission measuring method and apparatus in accordance with a third embodiment of the present invention are applied. In these drawings, elements having same configurations and functions as those in the plasma processing apparatus and plasma monitoring apparatus of FIG. 1 are assigned same reference numerals, and detailed descriptions thereof are omitted.

The plasma light emission measuring apparatus of the present embodiment includes a cylindrical transparent insulating pipe 50 fixedly attached to a chamber 10, a rod-shaped optical transmission probe 130 provided with a light receiving surface 130a at a front end thereof and inserted into a quartz pipe 50 through one end of the quartz pipe 50 (left-hand side of FIG. 1) to slide therethrough, a measurement unit 132 for measuring light emission from plasma PZ created in the chamber 10 through the probe 130, a linear actuator 56 for moving the probe 130 in an axial direction thereof, and a flexible bundle fiber 134 for optically connecting the probe 130 to the measurement unit 132.

The transparent insulating pipe 50 is made of a transparent and heat-resistant insulating material, e.g., quartz or sapphire, somewhat longer than an outer diameter of the chamber 10, rectilinearly (linearly) formed, and open at both ends thereof.

The front end of the probe 130, as illustrated in FIG. 33, is mounted with a light shielding type cylindrical cap 136 made of, e.g., stainless steel (SUS). A cylindrical body 138 made of, e.g., stainless steel is accommodated in the cap 136. A section 140 of the cylindrical body 138 facing the light receiving surface 130a of the probe 130 forms a mirror inclined by 45° with respect to the axial direction. A circular opening or window 142 is formed in the sidewall of the cap 136 at a location positioned in the reflection direction of the mirror 140 when viewed from the light receiving surface 130a of the probe 130. The light entering the window 142 from a location in front of the window 142 is reflected by the mirror 64, and is incident on the light receiving surface 130a of the probe 130. As described above, in the present embodiment, a light collecting unit 144 for collecting plasma light in the chamber 10 to have high directionality is formed by employing the window 142, the mirror 140 and the light receiving surface 130a of the probe 130.

The probe 130 is formed of a quartz rod of, e.g., several mm or less in diameter. The probe 130 confines light incident on the light receiving surface 130a at the front end thereof while totally reflecting the light by the boundary surface or surrounding surface thereof, transmits the light to the other end thereof, and irradiates the light through the surface of the other end thereof. As the quartz rod, a rod made of hydrous synthetic quartz, which exhibits a high transmission characteristic and does not emit fluorescence, is preferably used in a case where wavelengths ranging from 200 nm to 900 nm used for the general spectroscopy of plasma light emission are required. Meanwhile, in the measurement of a wavelength range of a near infrared ray to a middle infrared ray (900 nm~), anhydrous synthetic quartz or fused quartz that exhibits a high transmission characteristic in the wavelength range is preferably used as the rod material. To efficiently perform the measurement of a wide wavelength range of an ultraviolet ray to an infrared ray, sapphire may be used as the rod material.

The probe 130, as described above, sufficiently performs light transmission with only a single body of quartz rod. However, to prevent faint light from entering the side surface of the quartz rod, the side surface or surrounding surface of the rod may be preferably surrounded with a cladding 146, as shown in FIG. 34A. More preferably, as shown in FIG. 34B, the surrounding surface of the cladding 146 (or the quartz rod 130) may be surrounded with a light shielding coating, e.g., a black paint 148.

The measurement unit 132 is an apparatus for measuring the light emission of plasma in the chamber 10 using spectroscopic analysis through the probe 130. The measurement unit 132 includes a spectroscope 150 for dissolving or dividing light from the probe 130 into a spectrum, a photoelectric conversion unit 152 for converting a spectrum of a certain frequency obtained from the spectroscope into an electrical signal, a measurement operation unit 154 for obtaining the intensity of a spectrum corresponding to the output signal of the photoelectric conversion unit 152, and a measurement control unit 156 for controlling measurement-related units. For example, a prism or diffraction grating may be used as the spectroscope 150. An optical filter instead of the spectroscope may be used. For example, a photomultiplier tube or photodiode may be used as the photoelectric conversion unit 152.

The bundle fiber 134 is formed by binding a plurality of flexible optical fibers, one end of which is optically connected to one end of the probe 52 via a connector 158, and the other end of which is optically connected to the spectroscope 150 of the light emission measurement unit 132. The connector 158 connects the bundle fiber 134 to the probe 130, e.g., in an end-to-end manner.

Hereinafter, the operation of the plasma light emission measuring apparatus of the present embodiment is described. In the plasma light emission measuring apparatus, the probe 130 is moved within the quartz pipe 50 in the axial direction thereof, that is, the radial direction of the chamber 10 by the rectilinear operation of the linear actuator 56 so as to measure light emission from plasma PZ created in the chamber 10. In general, the light receiving surface 130a of the probe 130 is inserted into an inner side of the quartz pipe 50 up to a location over the farthest measurement location when viewed from the linear actuator side, and is rectilinearly moved in the direction of pulling the probe 130 during measurement. With this rectilinear movement in the axial direction, the light collecting unit 144 of the probe 130 scans a plasma space in chamber 10 in the radial direction thereof, and collects plasma light at respective locations in the radial direction. In more detail, as shown in FIG. 33, light generated from the plasma PZ at a higher location enters the quartz pipe 50 and is incident on the mirror 140 through the window 142 of the cap 136 at respective locations on a scan line, and light reflected by the mirror 140 is incident on the light receiving surface 130a of the probe 130. Although, in the example shown in the drawing, plasma light is collected from a location above the probe 130, plasma light may be collected from any location such as locations below and beside the probe 130 as well as a location above the probe 130 depending on the orientation of the mirror 140.

The plasma light incident on the light receiving surface 130a of the probe 130 propagates within the probe 130, is irradiated in the connector 158 toward the other end surface of the probe 130, and is incident on one end surface or light receiving surface of the bundle fiber 134. The plasma light incident on the light receiving surface of the bundle fiber 134 propagates within the bundle fiber 134, and is irradiated from the other end surface of the bundle fiber 134, and enters the spectroscope 150 of the measurement unit 132.

In the measurement unit 132, the spectroscope 150 extracts a spectrum from the received plasma light. The photoelectric conversion unit 152 converts the spectrum extracted by the spectroscope 150 into, e.g., an optical current, and outputs a voltage signal corresponding to the intensity of the spectrum. The measurement operation unit 154 obtains a measured value of the intensity of the spectrum from the level of the voltage signal obtained by the photoelectric conversion unit 152. Since the light collecting unit 144 is allowed to scan in the radial direction of the chamber 10 by moving the probe 130 within the quartz pipe 50 in the radial direction thereof using the linear actuator 56 as described above, the intensity of plasma light or spectrum can be measured at respective locations on a scan line. Furthermore, by mounting a position sensor such as a linear encoder or rotary encoder on the linear actuator 56, the location of the light collecting unit 144, i.e., a measurement location, can be detected. The measured values of the intensity of spectra at the respective locations are stored in a memory of the measurement operation unit 154 or measurement control unit 156 as plasma light emission measurement data, are displayed or printed as spatial distribution characteristics (graph) by a display device or printer (not shown) or used for a required monitoring analysis.

As described above, in the plasma light emission measurement apparatus, the quartz pipe 50 is inserted into the chamber 10, the rod-shaped optical transmission probe 130 is moved within the quartz pipe 50 in the radial direction thereof, the emitted light of the plasma PZ is collected by the light collecting unit 144 of the probe 130 at certain measurement locations in the axial direction, the collected plasma light is transmitted to the measurement unit 132 through the probe 130 and the bundle fiber 134, and measured values of a certain characteristic or an attribute (for example, the intensity of a certain wavelength spectrum) are obtained by the measurement unit 132 with respect to plasma light at the respective measurement locations.

In this case, since the quartz pipe 50 and the probe 130 are insulating material, i.e., nonmetal, there is no concern for the disturbance of the plasma PZ and highly reliable and precise spatial distribution measurement can be performed on plasma light emission, even though they are inserted into capacitively coupled plasma PZ created between parallel flat plate electrodes 16 and 24. Furthermore, in this embodiment, the cap 136 and mirror 140 of the light collecting unit 144 are made of metal (SUS) and the entire length of the metallic member is several cms, they cannot perform an antenna function, so that they do not influence high frequency discharge between the parallel flat plate electrodes 16 and 24.

Furthermore, in the present embodiment, the quartz pipe 50 is horizontally hung between a pair of supports (through holes 10a) provided at the opposite locations of the sidewalls of the chamber 10, and the probe 130 is moved within such a bridge-type quartz pipe 50 (using the quartz pipe 50 as a guide member) in the axial direction thereof, so that the scanning of the probe can be realized stably at a high-speed on a certain horizontal line in the radial direction of the chamber. In this way, even in a short processing time of, e.g., a several minutes, the above-described spatial distribution measurement can be repeated a plurality of times at regular intervals and resolution measurement can be performed in a time axis direction.

Furthermore, in the present embodiment, by providing plasma light collected by the probe 130 in the chamber 10 to the spectroscope 150 of the measurement unit 132 through the bundle fiber 134 outside the chamber 10, plasma light emission in the chamber 10 can be collected at a desired viewing angle.

With reference to FIG. 35, the optical functions of the probe 130 and the bundle fiber 134 are described. In the chamber 10, light emission from the plasma PZ passes through the window 142 of the cap 136, is reflected by the mirror 140, and is incident on the light receiving surface 130a of the probe. In this case, the plasma light is incident on the light receiving surface 130a of the probe 130 actually at a viewing angle of ±90° (NA=1) regardless of a unique numerical aperture N/A of the probe 130. Additionally, the plasma light is irradiated from the other end surface of the probe 130 actually at a viewing angle of ±90°, which is symmetrical with the light receiving side of the probe 130. As a result, the plasma light is incident on the light receiving surface 134a of the bundle fiber 134, which is actually a same situation as on the light receiving surface 130a of the probe 130. The bundle fiber 134 receives the plasma light at a unique numerical aperture (NA<1), the other end surface 134b irradiates the plasma light at a unique numerical aperture (NA<1). In this way, plasma light can be collected with a directionality equivalent to that of a case where the light receiving surface 134a of the bundle fiber 134 is put into the chamber 10.

Meanwhile, if the bundle fiber 134 is put into the chamber 10, the protective tube (generally, made of metal) thereof is electrically coupled with plasma PZ, so that the plasma PZ may be disturbed. In the present embodiment, since the bundle fiber 134 exists outside the chamber 10, it does not influence the plasma PZ.

Further, the bundle fiber 134 has an advantage in that it is easy to be aligned with the probe 130 in the connector 158 compared to a single optical fiber, in addition to the above-described directionality.

Meanwhile, if the diameter of the rod of the probe 130 is increased, undesired light ML directly incident on the light receiving surface 130a from a front location without passing through the mirror 140 as well as original light PL incident from a location in front of the window 142, reflected by the mirror 140 and incident on the light receiving surface 130a of the probe 130 may be mixed in the collected plasma light collected by the light collecting unit 144, as shown in FIG. 36. In order to solve this problem, as shown in the drawing, one end of the probe 130 is preferably formed of a light receiving surface slantingly cut at a certain angle θ so that a normal line N of the light receiving surface 130a of the probe 130 is slanted with respect to the axial direction toward the window side at the angle θ. With this configuration, even though the undesired light ML is incident on the light receiving surface 130a of the probe 130 from a front location, the light is incident at an angle larger than the numerical aperture NA of the bundle fiber 134, so that the frontal light can be eliminated.

FIG. 37 shows the optimal cut angles θ of the light receiving surface of the quartz rod used in the probe 130 with respect to the refractive indices thereof on a graph, with numerical apertures being used as a parameter. Since the refractive index of the quartz rod varies with the wavelength of light, a cut angle θ may be determined based on the shortest wavelength of a spectrum to be measured in an actual application. For example, in case of using a quartz rod having a numerical aperture of 0.22, when a refractive index corresponding to the shortest spectrum to be measured is 1.453, the cut angle θ may be set to 26.8° based on the graph of FIG. 37.

As described above, in accordance with the plasma light emission measuring apparatus of the present embodiment, light emission from the plasma can be measured or spectroscopically analyzed in view of a spatial distribution in the radial direction of the chamber without influence on a plasma distribution within the chamber 10. Accordingly, a correlation between the intra-surface distribution of processing results and the spatial distribution of plasma light emission can be interpreted with high precision.

FIGS. 38A to 40B show an example of a correlation between the intra-surface distribution of the etching rates and the spatial distribution of plasma emission in an application in which the plasma processing apparatus of the present embodiment is applied to perform a plasma etching.

FIGS. 38A and 38B show the correlation between the intra-distribution of etching rates E/R of $SiO_2$ (FIG. 38A) and the spatial distribution of Ar radical light emission I [Ar] (750 nm: 13.48 eV) (FIG. 38B) in two types of silicon dioxide ($SiO_2$) film etching A and B with the resistivities of upper electrodes 24 being different.

FIGS. 39A and 39B show the correlation between the intra-distribution of etching rates E/R of $SiO_2$ (FIG. 39A) and the spatial distribution of Ar radical light emission I[Ar](750 nm: 13.48 eV) (FIG. 39B) in two types of silicon dioxide ($SiO_2$) film etching C and D with the structures of upper electrodes 24 being different.

FIGS. 40A and 40B show the correlation between the intra-distribution of etching rates E/R of photoresist (FIG. 40A) and the spatial distribution of Ar radical light emission I[Ar]/F radical light emission I[F] (704 nm: 14.75 eV) (FIG. 40B) in two types of silicon dioxide ($SiO_2$) film etching C and D with the structures of upper electrodes 24 being different.

FIGS. 41 to 43 show a configuration and an operation of a plasma processing apparatus to which plasma light emission measuring method and apparatus according to another embodiment (fourth embodiment) are applied. In these drawings, elements having same configurations and functions as those of the third embodiment are designated by same numerals.

In this embodiment, an opening or hole 162 to which a shutter 160 is attached is formed in a sidewall of a chamber 10 at a height in the middle of upper and lower electrodes 24 and 16, and a rod-shaped optical transmission probe 164 provided with a light receiving surface 164c at a front end portion thereof is configured to be put into and drawn from the hole 162 in the radial direction of the chamber. The probe 164 may be an optical fiber having a dual structure including a core 164a formed of, e.g., quartz (synthetic quartz or fused quartz) or sapphire, and a cladding 164b (FIG. 43).

The probe 164 is accommodated in a bellows 166 placed to freely expand and contract in the radial direction of the chamber outside the chamber 10. A base portion of the probe 164 is horizontally supported by a slider 76 of an actuator 56, and is optically connected to a bundle fiber 134 through a connector 158. The bellows 166 is in contact with the chamber 10 at one end thereof and the slider 76 at the other end thereof, which forms an airtight space around the probe 164. An inside space of the bellows 166 is adapted to be depressurized to a vacuum degree equal to that of the chamber 10 by a gas exhaust unit 170 through a gas exhaust pipe 168. A heater 172 (for example, a PTC element or resistant heating element) is provided inside or around the bellows 166 to heat the probe 164 to a certain temperature (for example, a temperature around 100° C.).

In this embodiment, while plasma light emission measurement is not being performed, the shutter 160 is closed and the probe 164 is pulled out of the chamber 10, as shown in FIG. 41. However, before plasma light emission measurement is performed, the inner space of the bellows 166 is depressurized to a vacuum degree almost equal to that of the chamber 10, and the probe 164 is heated to a certain temperature. When plasma light emission measurement is performed, the shutter 160 is opened, the linear actuator 56 is operated, to move rectilinearly the probe 164 in the axial direction and inserted into the chamber 10 through the hole 162, as shown in FIG. 42. At this time, the bellows 166 contracts as the slider 76 and the probe 164 moves forward.

Light is incident on the light receiving surface 164c of the probe 164 from the plasma PZ in the chamber 10. The viewing angle of the probe 164 is restricted by a numerical aperture NA that is determined by the refractive indices of the core 164a and the cladding 164b. A light distribution on a scan line can be measured by obtaining a variation ΔI of the luminous intensity of the plasma with respect to a minute moving distance Δx using the measurement unit 132 while moving (scanning) the probe 164 in the axial direction, i.e., the radial direction x of the chamber. Such a measurement scanning may be performed during any of forward (advance) and backward (return) movement of the probe 164.

Even through the cladding 164b of the probe 164 is struck by the plasma PZ in the chamber 10, the core 164a propagating collected plasma light is not influenced. Further, since the probe 164 has been heated to high temperature outside the chamber 10, an amount of deposits are attached thereto is small even though the probe 164 is exposed to the plasma PZ in the chamber 10.

Since the probe 164 is made of non-metal, the probe 164 does not disturb the plasma PZ and can perform scanning within a very short time (for example, several seconds) compared to processing time (for example, several minutes), thus scarcely influencing processing results. For this reason, it is possible to perform such a measurement scanning a plurality of times during processing time at regular intervals. Further, measurement results having high correlation with processing results can be obtained. This embodiment may be applied to actual processing as well as the development of processing. For example, this embodiment may be applied to light emission monitoring used to control a process such as the detection of a termination point in plasma etching.

In the above-described third and fourth embodiments, plasma light emission is measured in the form of a spatial distribution while moving the probes 130 and 164 in the axial direction of the chamber 10. However, in the present invention, it is possible to move the probe in the chamber 10 in an arbitrary direction. For example, as shown in FIG. 44, a plasma light distribution in the vertical direction z can be measured by obtaining a variation ΔI of the luminous intensity of the plasma with respect to a minute moving distance Δz using the measurement unit 132 while moving (scanning) the probe 130 in the vertical direction z in a plasma space in the chamber 10.

In the plasma light emission measuring apparatus of the present invention, some other plasma attribute can be obtained from the measured values of the light emission of plasma obtained by the spectroscopic analysis method described above. In general, emission species, such as an atom, a molecule, a radical and an ion, emit light at a unique wavelength or spectrum corresponding to the internal energy state thereof. The luminous intensity $I_x$ of a certain emission species is given by Equation 5.

$$I_x = C_{x,\lambda} \cdot N_x n_e \cdot \int \sigma_x(E) \cdot v_e f_e(E) \cdot dE \qquad \text{Eq. (5)}$$

where $C_{x,\lambda}$ is a physical property value of the emission species (such as wavelength, spontaneous emission probability, etc.) or a coefficient representing a geometrical element related to a measurement system. Further, $N_x$ is density of the emission species at a base energy state, $n_e$ is electron density, $\sigma_x(E)$ is the electron collision-excited section of the emission species X, $v_e$ is the speed of an electron, and $f_e(E)$ is an electron energy distribution function (EEDF). Furthermore, the integration $\int$ of Equation 5 ranges from 0 to infinity ($\infty$).

As described above, the light emission of plasma is determined by several plasma quantities. In other words, various quantities, such as the density of an emission species, electron density and an electron density distribution, are obtained from the measured values of plasma light emission.

For example, when $N_x$ is obtained by using an actinometry method and electron density $N_e$ is obtained by using an electron density measuring method, such as a PAP method or Langmuir probe method, an electron energy distribution $f_e(E)$ can be obtained from Equation 5.

In the plasma light emission measuring apparatus of the present embodiment, it is possible to displace each element with a substitute having same function. For example, although, in the above embodiment, the quartz pipe 50 is installed to traverse the chamber 10 in the radial direction like a bridge, it is possible to secure the quartz pipe 50 at a single location in a cantilever manner. Further, in this embodiment, the probes 130 and 164 are made to be moved in the axial direction, that is, the radial direction of the chamber 10, by the rectilinear operation of the linear actuator 56. However, the probes 130 and 164 may be moved forward and backward in the axial direction of the quartz pipe 50 or chamber 10, or may be rectilinearly moved as in the above-described embodiment in a manual manner.

FIGS. 45 to 47 show variants of this embodiment. A variant of FIG. 45 is formed by constructing the probe 130 of the first embodiment with a bundle type optical guide including a plurality of optical fibers 166 instead of a single body quartz rod. To integrate the plurality of optical fibers 166 into a single part, a heat-resistance non-metallic member 168 is provided around the bundle. The material of the heat-resistant non-metallic member 168 is preferably a heat-resistant polymer, e.g., polyimide, which may be wound around the bundle in the form of a tape or gathered in the form of a resin. Since such a bundle type probe 130 has an advantage in that it has such flexibility as not to be easily damaged.

A variant of FIG. 46 is formed by integrating such a bundle type probe 130 to be inserted to the chamber 10 and a standard bundle fiber 134 to be extended from the chamber 10. That is, each optical fiber 166 of the probe 130 and each optical fiber 166 of the bundle fiber 134 form a single continuous optical fiber, and the probe 130 and the bundle fiber 134 are different in that a covering of the former 130 is an insulating material and a covering of the latter 134 is a metal. In accordance with the integrated optical fiber, there is no couple loss between the probe 130 and the bundle fiber 134, and the amount of light received by the measurement unit 132 side [in particular, spectroscope 150] is increased, thereby measurement precision being improved.

A variant of FIG. 47 is formed by constructing the mirror 140 of the probe 130 with aluminum. Aluminum is a material having a certain high reflection factor for rays ranging from an ultraviolet ray to an infrared ray, and can be used to be suitable for the mirror 140. However, aluminum is easily oxidized and then deteriorated. Accordingly, in this embodiment, aluminum is deposited on a side of the transparent quartz substrate 170, and an aluminum-deposited film 172 and the transparent quartz substrate 170 are attached to a cylindrical body 138 made of SUS, with the aluminum-deposited film 172 functioning as a mirror protecting material being placed on the front side thereof and the transparent quartz substrate 170 functioning as a reflective film being placed on the back side thereof. The light of plasma PL to be measured is transmitted through the transparent quartz substrate 170 and reflected by the aluminum-deposited film 172. In another variant, although not shown, a cylindrical body 138 may be made of aluminum and a reflective surface or mirror surface 140 may be coated with a protective film made of magnesium fluoride.

An application of the plasma light emission measuring apparatus of the present invention is to monitor abnormal discharge in a chamber. For example, in the embodiment of FIG. 32, when the gas discharge hole (exhaust hole) 26 of the upper electrode 24 having a shower head structure is widened due to abrasion to cause abnormal discharge, the situation of abnormal discharge can be observed if the probe 130 is made to scan in the horizontal direction with the light collecting unit 144 of the probe 130 being directed upward. FIG. 48 shows an example of the application. As shown in the drawing, there is formed a spatial distribution having a pattern in which, when the gas discharge hole 26 of the upper electrode 24 has an abnormality (widened), light emission from the central portion of the electrode is decreased while the light emission from the outer portion thereof is increased, compared to a light emission distribution formed in the case where the gas discharge hole 26 of the upper electrode 24 is in a normal state. From this, it is possible to detect the occurrence of abnormal discharge and locations thereof. The experimental data of FIG. 48 is obtained by monitoring Ar radical light emission in silicon dioxide film etching. Basic plasma creating conditions (recipe) were as follows:

wafer diameter: 300 mm
gas pressure: 25 mTorr
distance between upper and lower electrodes: 35 mm
etching gas: $C_5F_8/O_2/Ar=29/750/47$ sccm
RF power: upper/lower=3300/3800 W
wafer backside pressure(center portion/edge portion): 10/40 Torr The above-described abnormal discharge monitoring function can be realized by the plasma electron density measuring methods and apparatuses in accordance with the first embodiment (FIG. 1) or the second embodiment (FIG. 19). FIG. 49 shows experimental data obtained by the plasma resonance probe method of the first embodiment (FIG. 1). The structure of a chamber and plasma creation conditions are same as those shown in FIG. 48. As shown in FIG. 49, there is formed a spatial distribution having a pattern in which, when the gas discharge hole 26 of the upper electrode 24 has an abnormality (widened), light emission from the central and outer portions of the electrode is increased, compared to a light emission distribution formed in the case where the gas discharge hole 26 of the upper electrode 24 is normal. From this, it is possible to detect the occurrence of abnormal discharge and locations thereof.

Various modifications can be made in the plasma processing apparatus of the present invention. In particular, the capacitively coupled parallel flat plate plasma creation method is an example, and the present invention can be applied to other methods, such as a magnetron method and an Electron Cyclotron Resonance (ECR) method. Further, the type of plasma processing is not limited to etching, but the present invention can be applied to some other plasma processing, such as chemical vapor deposition (CVD), oxidation or sputtering. Further, an object to be processed by the plasma processing is not limited to a semiconductor wafer, but the present invention can be applied to, for example, a glass substrate or liquid crystal display (LCD) substrate. The plasma light emission measuring method and apparatus of the present invention can be applied to plasma apparatuses other than the plasma processing apparatus.

BRIEF DESCRIPTION OF THE DRAWINGS

[FIG. 2] is a partially enlarged view showing principal parts of a probe of an embodiment;

[FIG. 27] is a graph showing frequency characteristics that represent the noise absorption effect of an electromagnetic wave absorber in an embodiment;

DESCRIPTION OF REFERENCE NUMERALS

Figure 1:
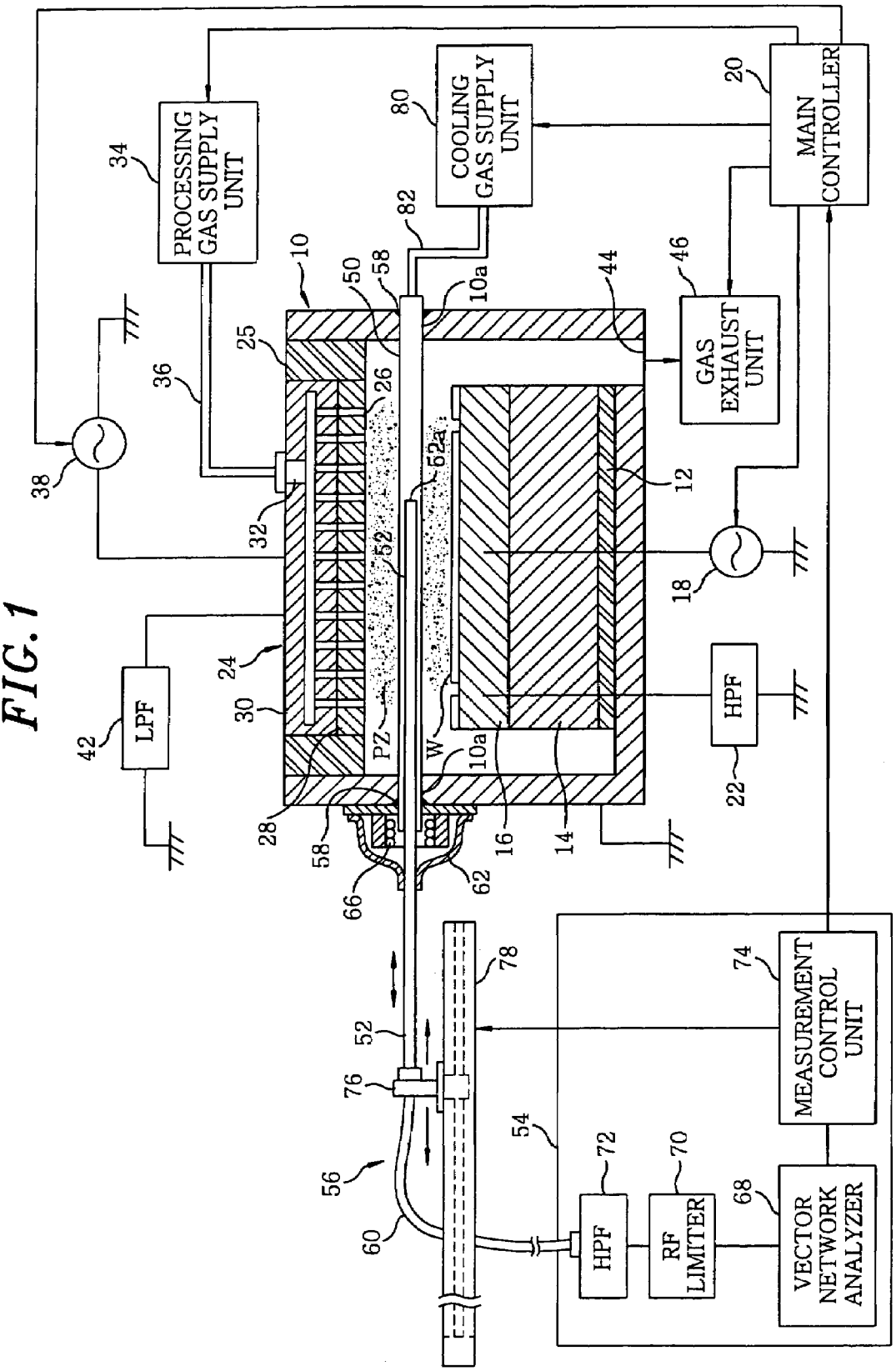
[FIG. 1] shows a configuration of a plasma processing apparatus to which plasma electron density measuring method and apparatus are applied in accordance with a first embodiment of the present invention.
Figure 3:
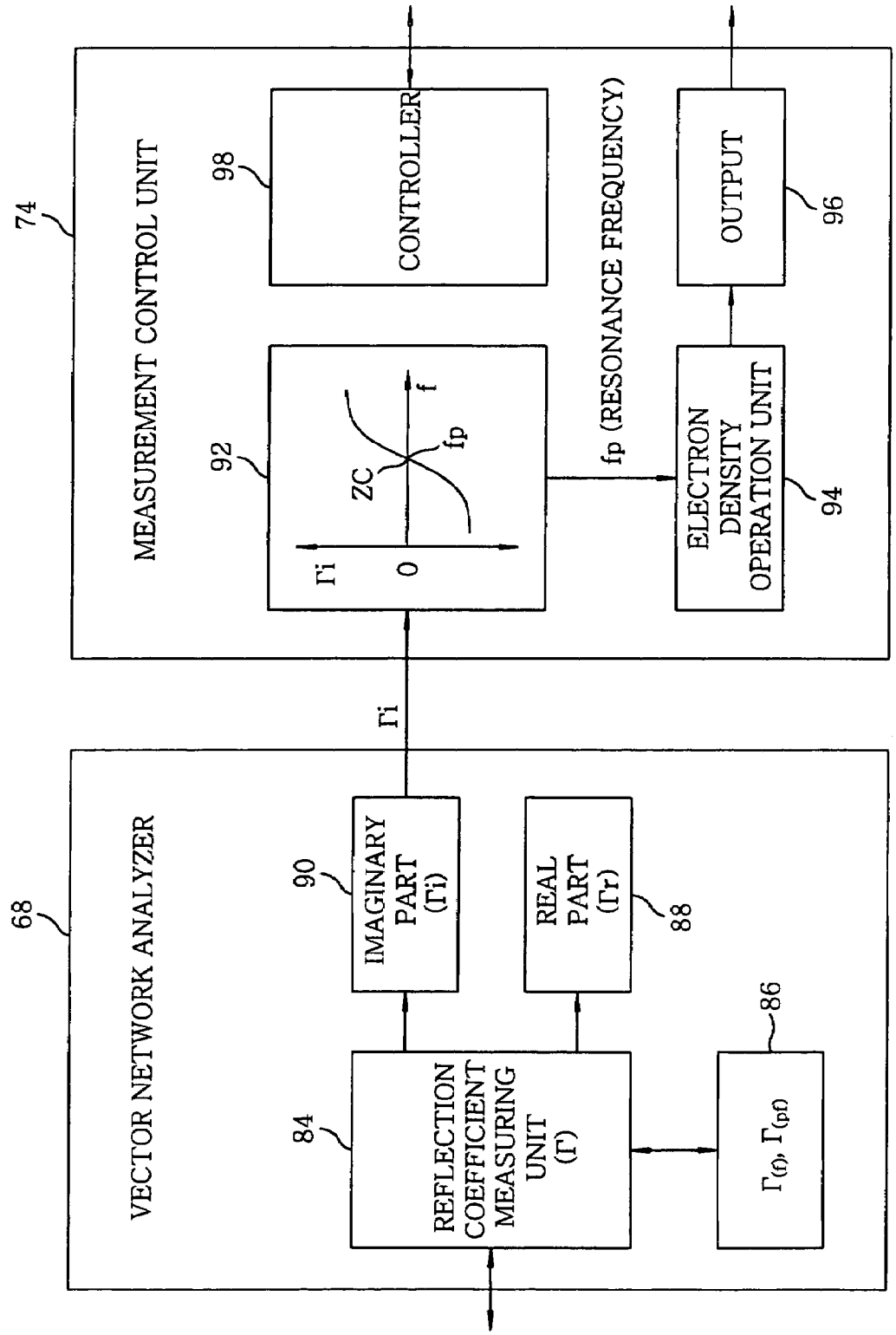
[FIG. 3] illustrates a block diagram showing a configuration of principal parts of a vector network analyzer and a measurement control unit in the measuring unit of the embodiment.
Figure 4:
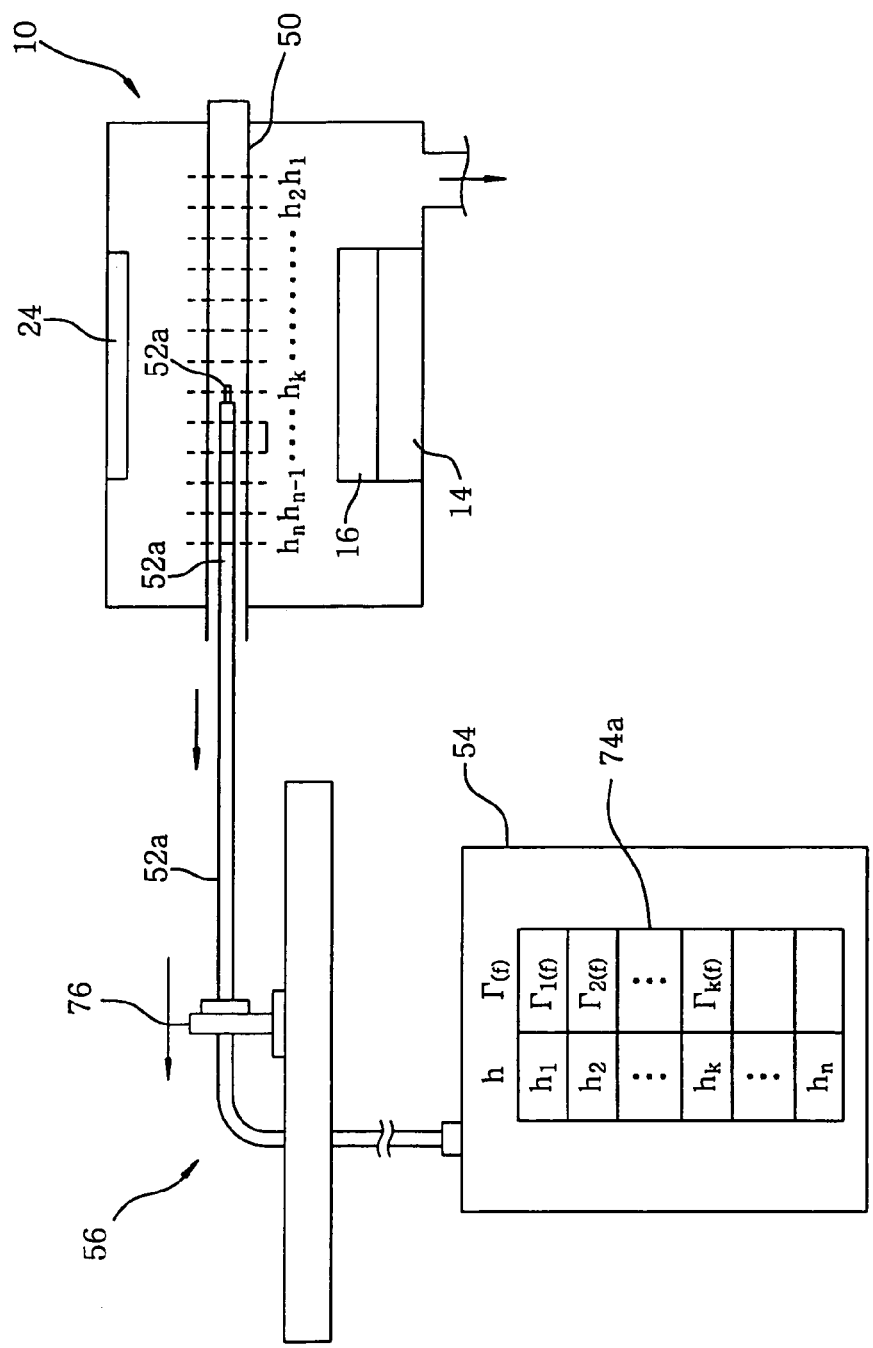
[FIG. 4] schematically describes a state of a first batch measurement process in an embodiment.
Figure 5:
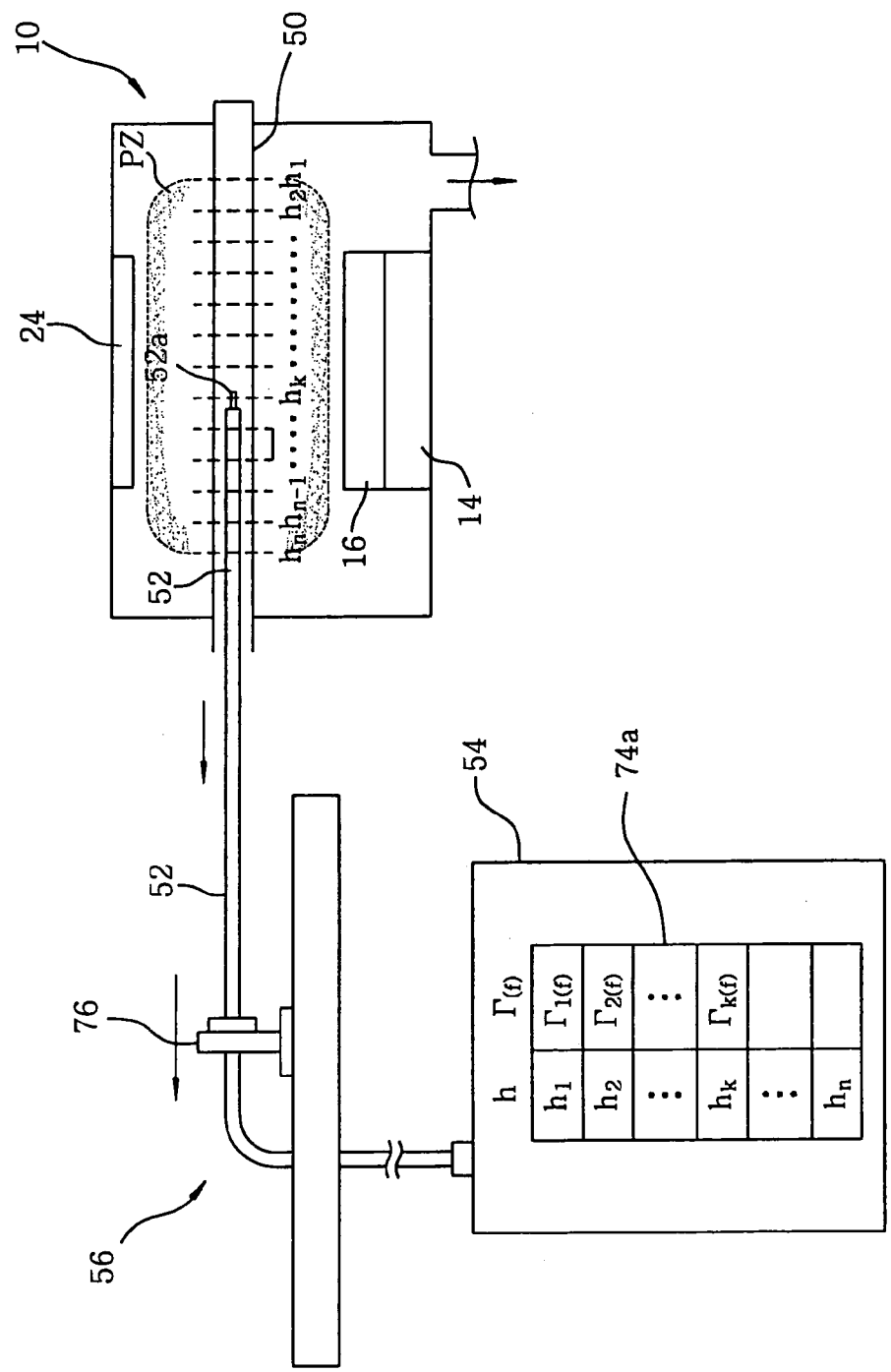
[FIG. 5] schematically depicts a state of a second batch measurement process in an embodiment.
Figure 6:
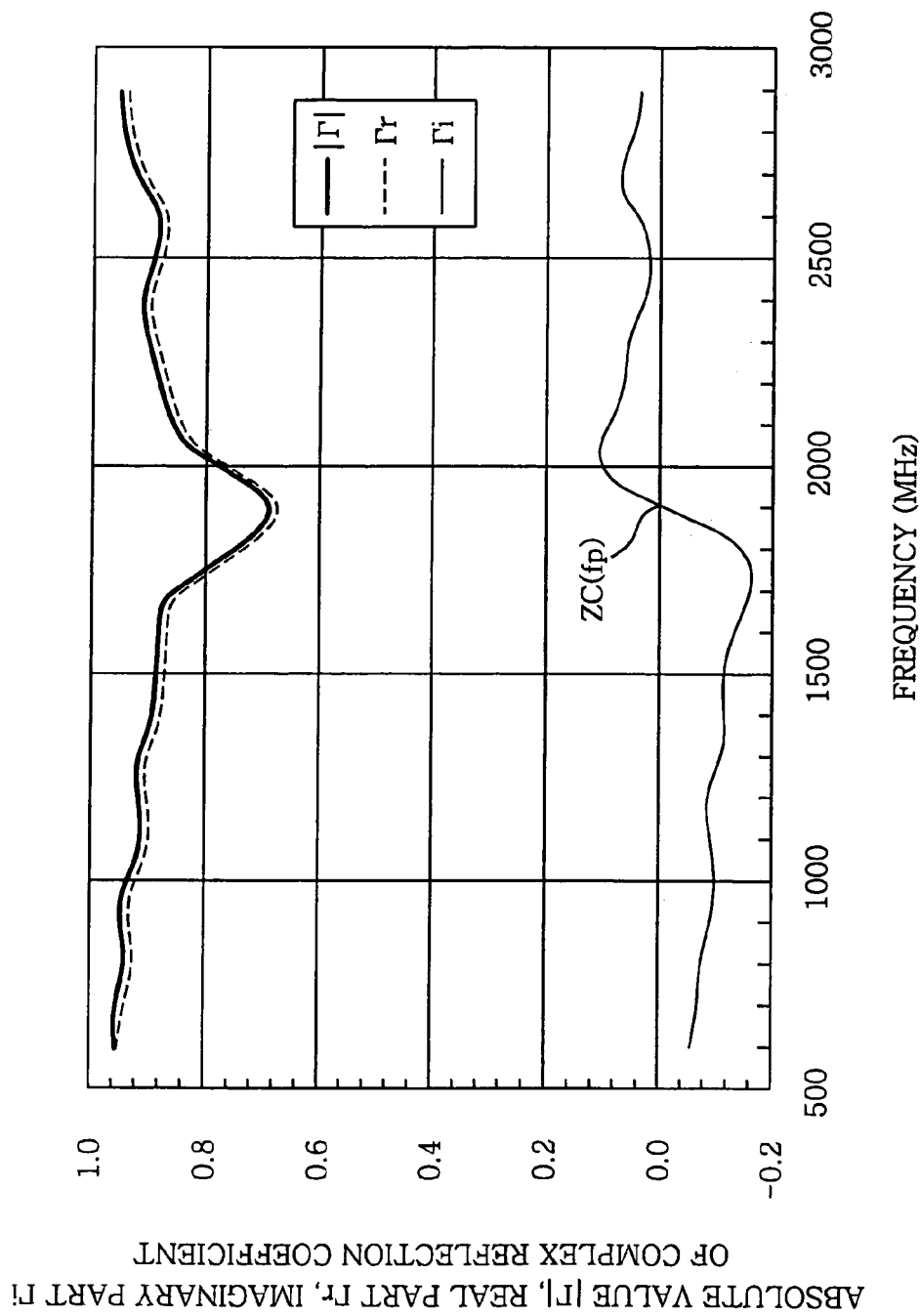
[FIG. 6] is a graph showing the frequency characteristics (experimental data) of the absolute values, real parts and imaginary parts of complex reflection coefficients obtained by using the plasma resonance probe method of the present invention.
Figure 7A:
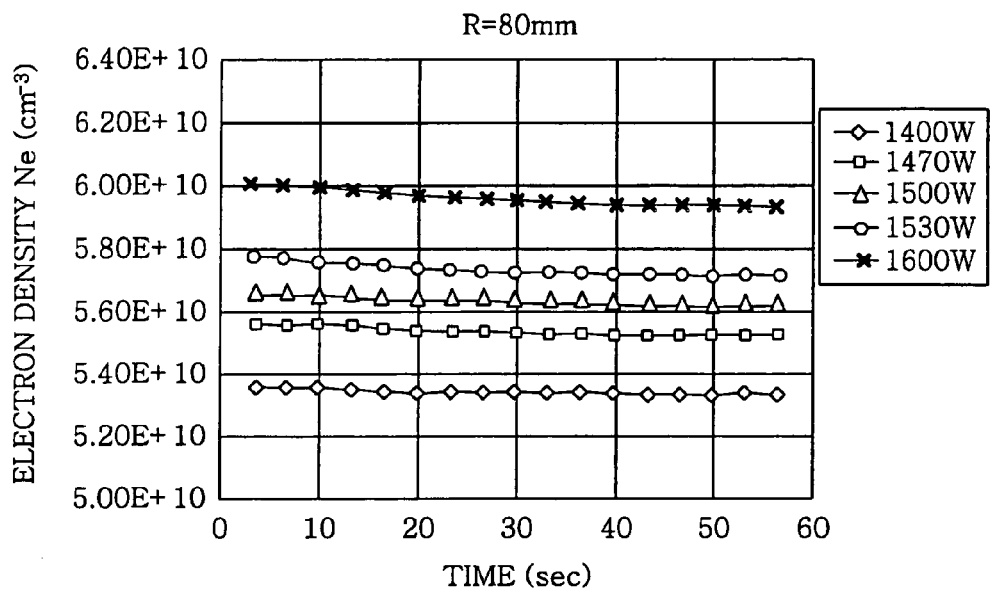
[FIG. 7A] exhibits an example (experimental data) of the measurement sensitivity of electron density obtained by using the plasma resonance probe method of the present invention.
Figure 7B:
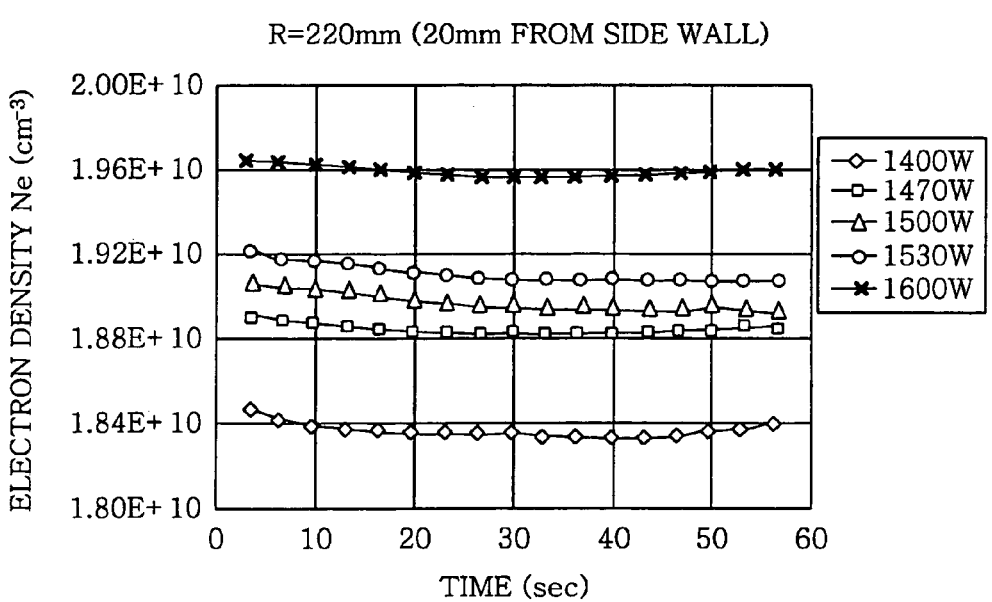
[FIG. 7B] exhibits an example (experimental data) of the measurement sensitivity of electron density obtained by using the plasma resonance probe method of the present invention.
Figure 8:
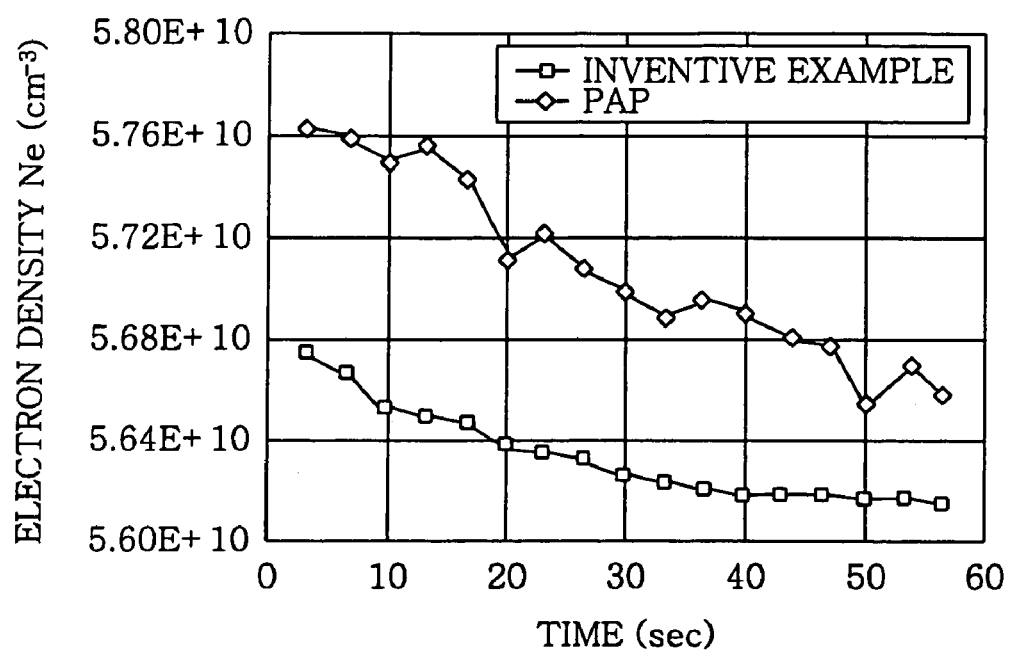
[FIG. 8] charts a measured value of electron density obtained in accordance with the present invention together with that of electron density obtained by using a PAP method.
Figure 9:
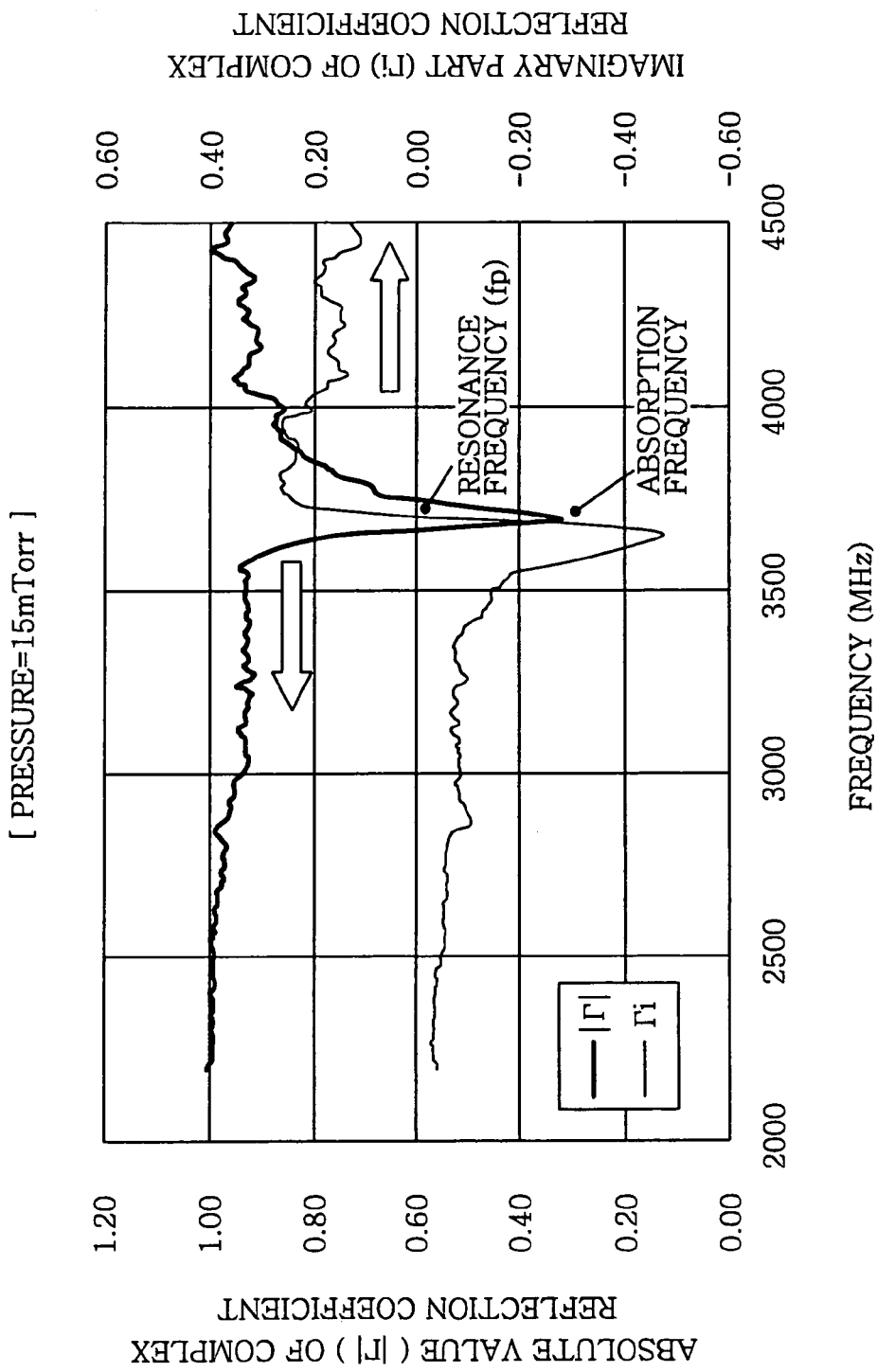
[FIG. 9] is a graph showing the frequency characteristics (experimental data) of complex reflection coefficients obtained under a relatively low-pressure condition (15 mTorr)
Figure 10:
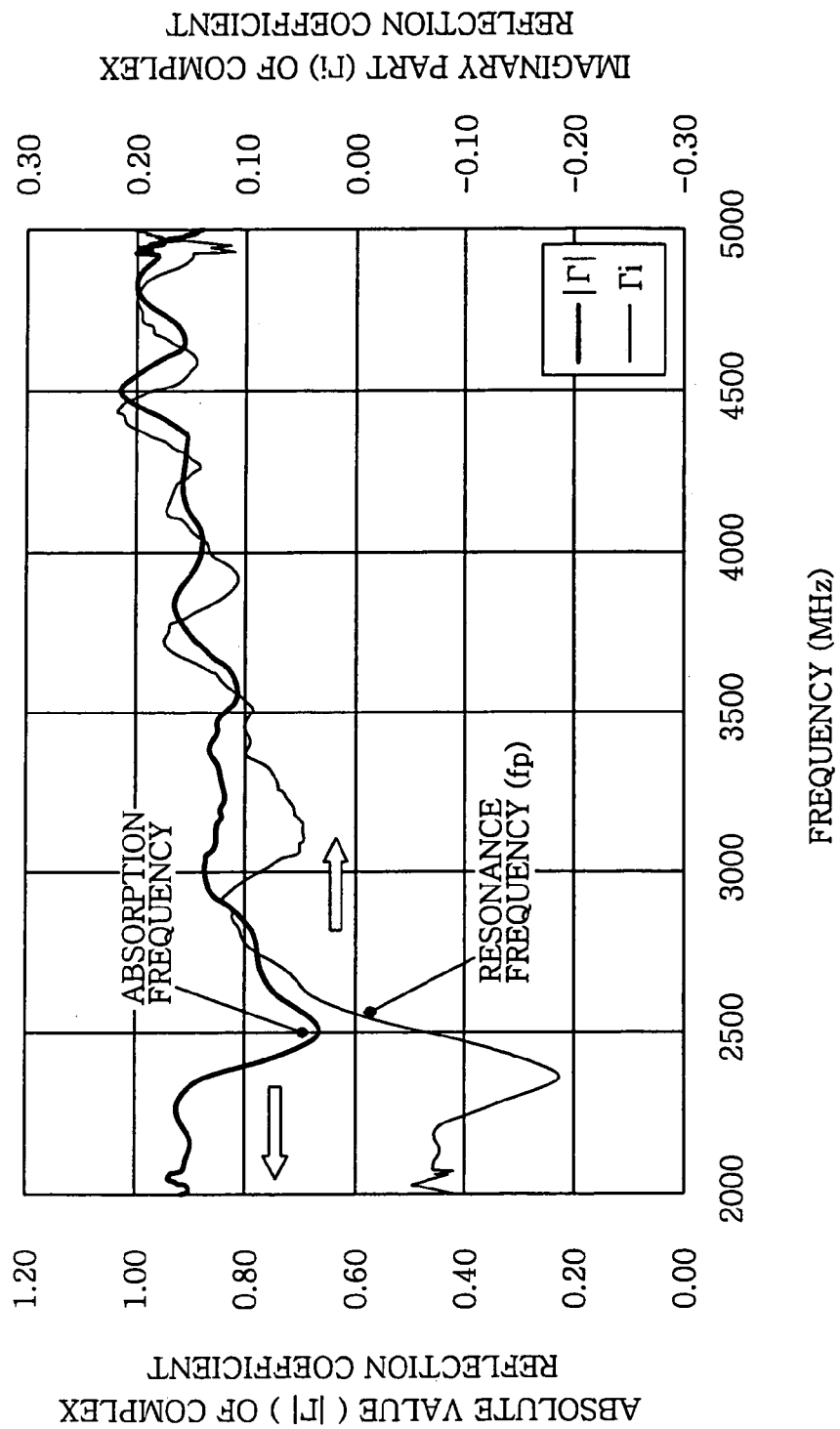
[FIG. 10] is a graph showing the frequency characteristics (experimental data) of complex reflection coefficients obtained under a high pressure condition (800 mTorr)
Figure 11:
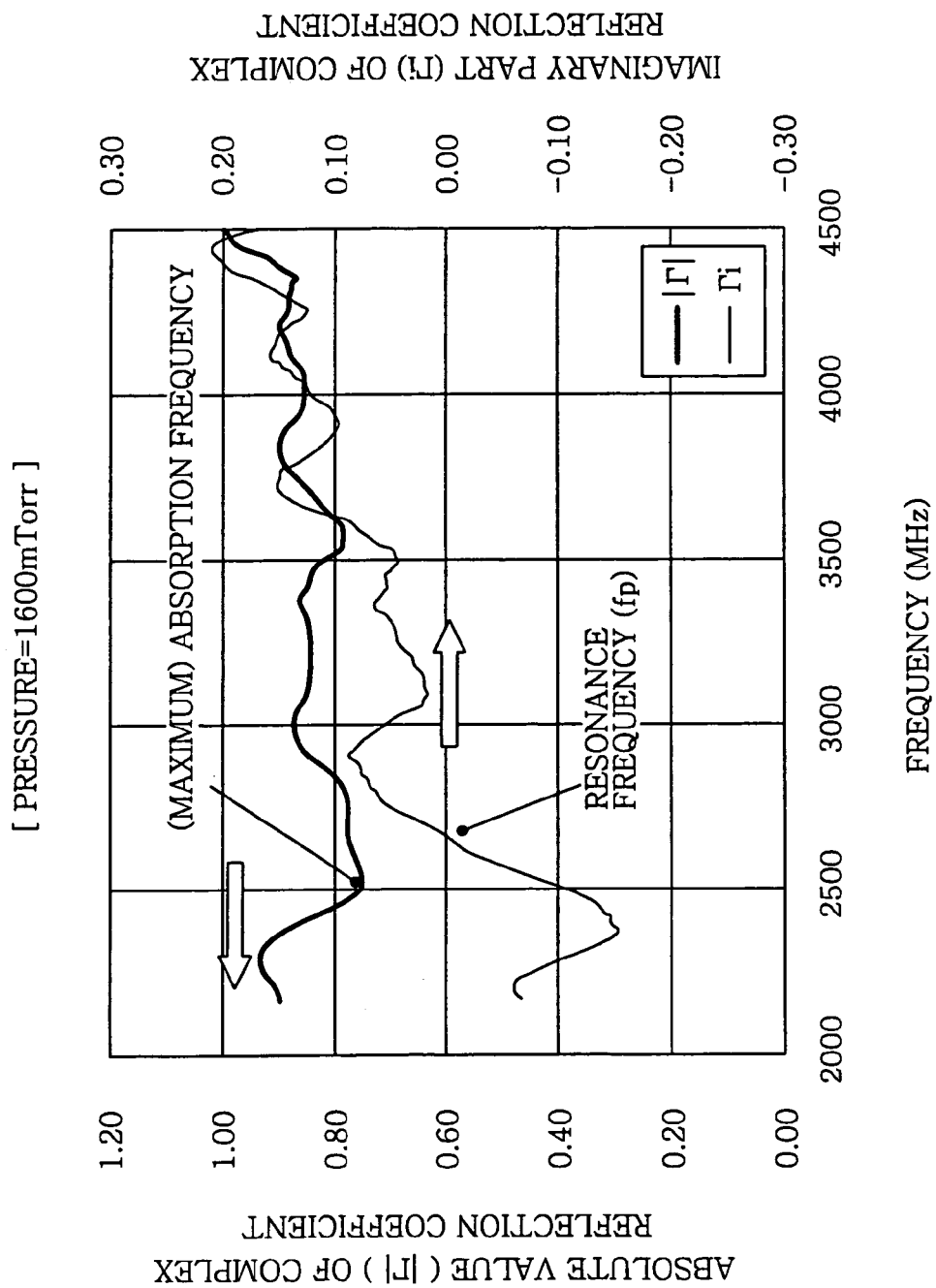
[FIG. 11] is a graph showing the frequency characteristics (experimental data) of complex reflection coefficients obtained under a high pressure condition (1600 mTorr)
Figure 12:
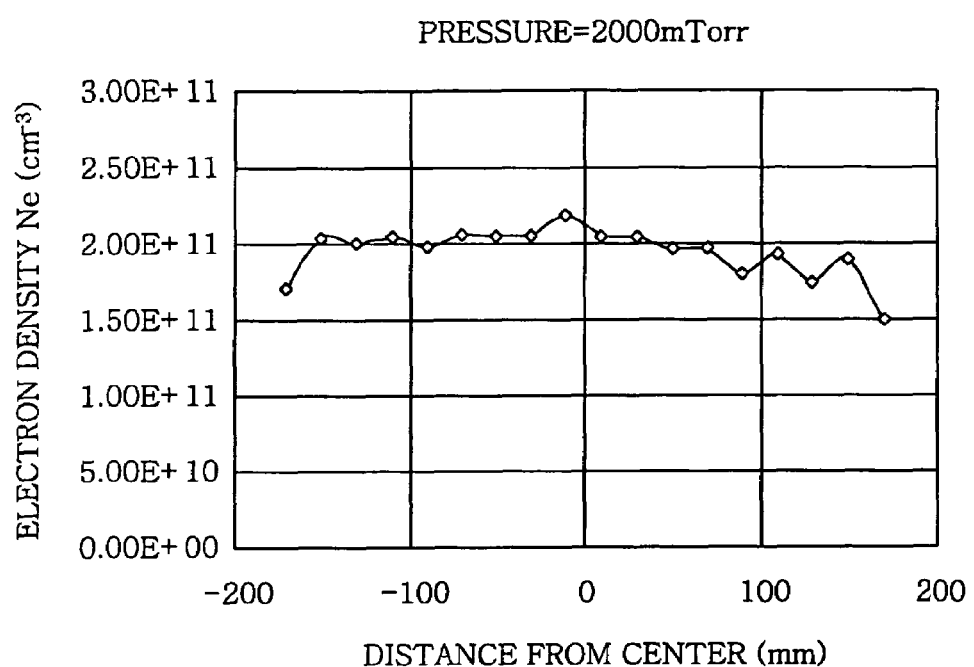
[FIG. 12] is a graph showing the frequency characteristics (experimental data) of complex reflection coefficients obtained under a high pressure condition (2000 mTorr)
Figure 13:
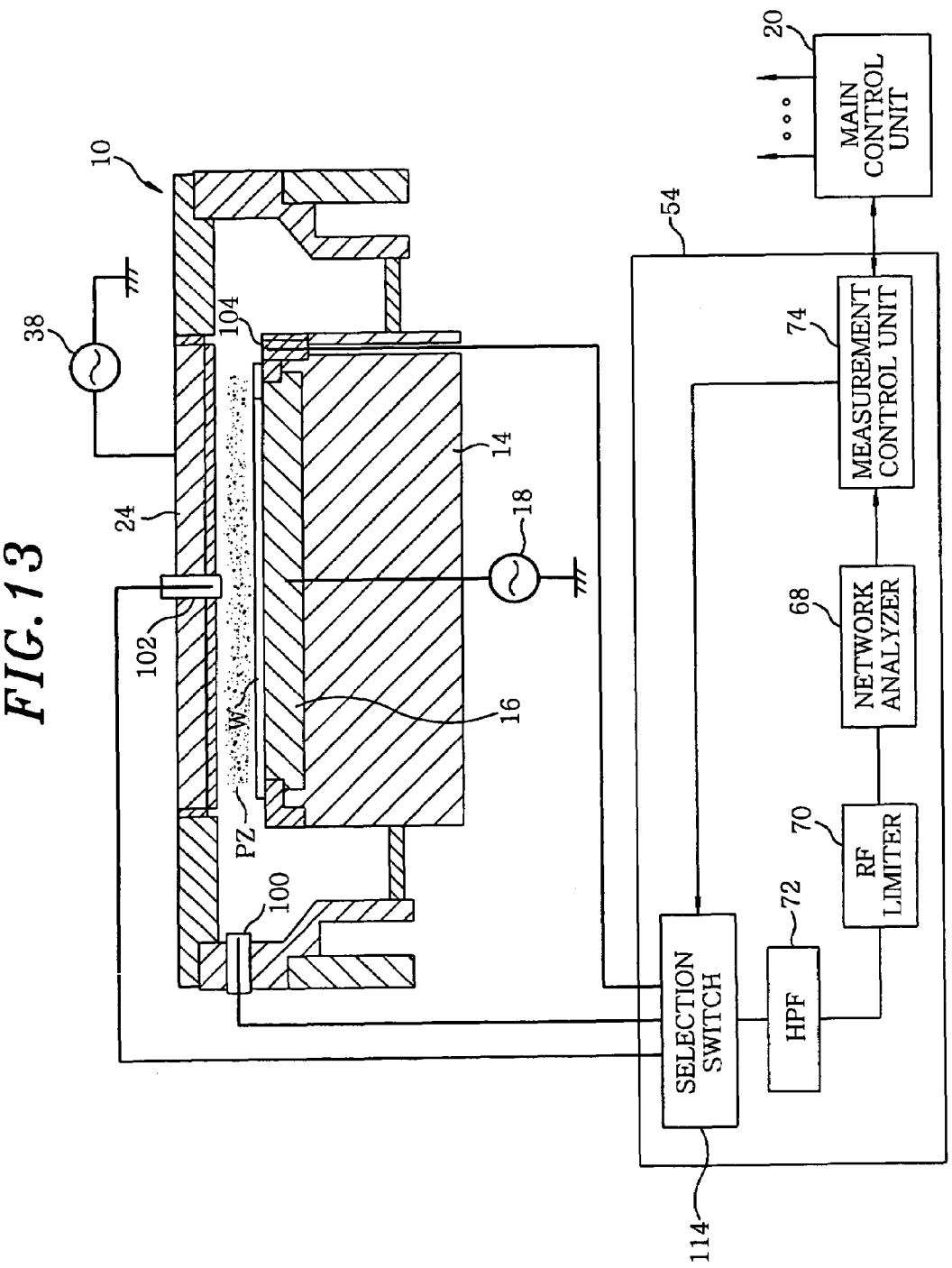
[FIG. 13] illustrates a configuration of a plasma processing apparatus to which a plasma electron density measuring apparatus is applied in accordance with another embodiment of the present invention.
Figure 14A:
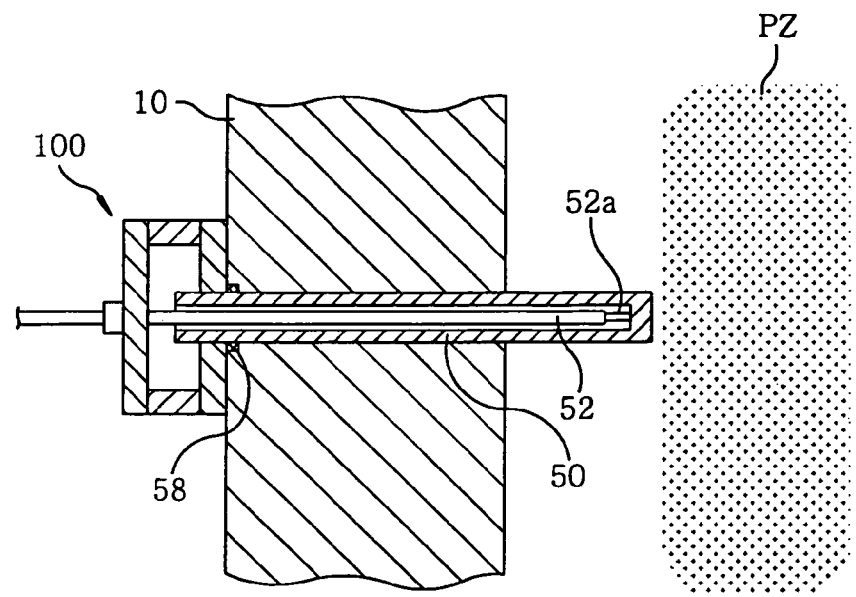
[FIG. 14A] describes a sectional view showing an example of probe unit that can be used in the embodiment of FIG. 13.
Figure 14B:
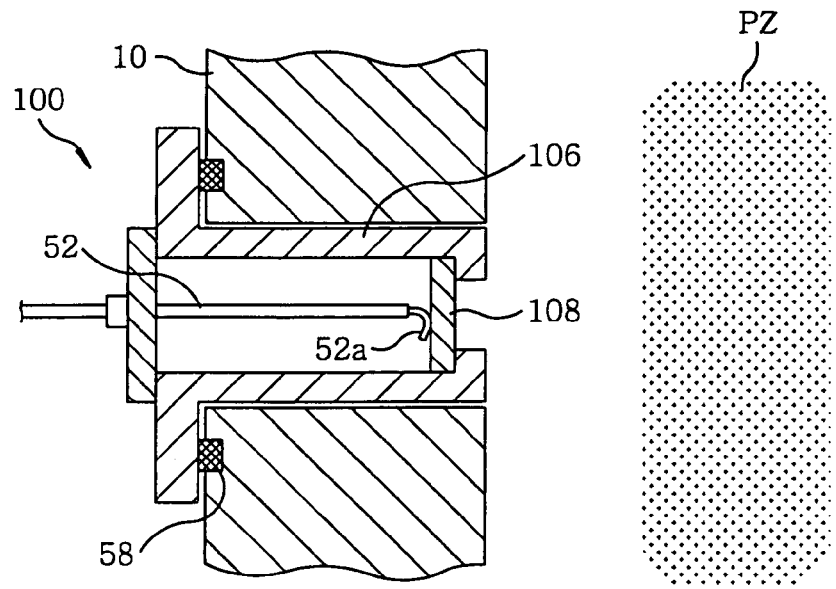
[FIG. 14B] describes a sectional view showing an example of probe unit that can be used in the embodiment of FIG. 13.
Figure 15A:
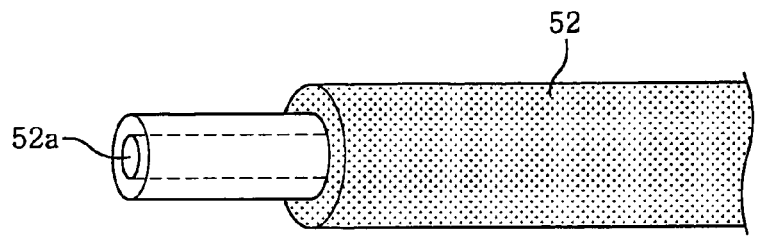
[FIG. 15] is a perspective view showing examples of probe portions that can be used in the embodiment of FIG. 13.
Figure 15B:
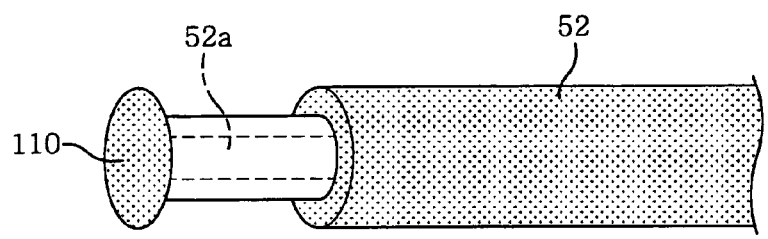
Figure 15C:
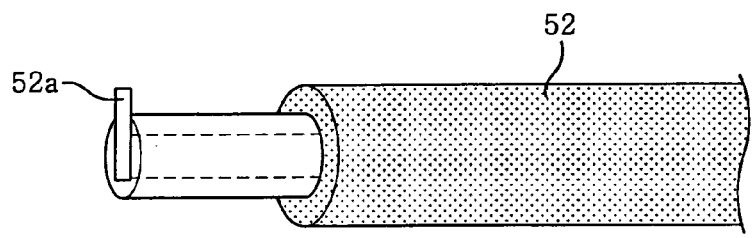
Figure 15D:
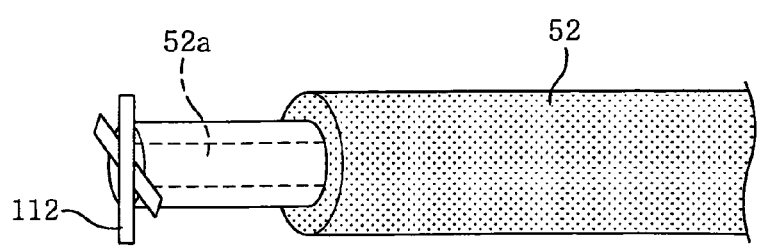
Figure 16:
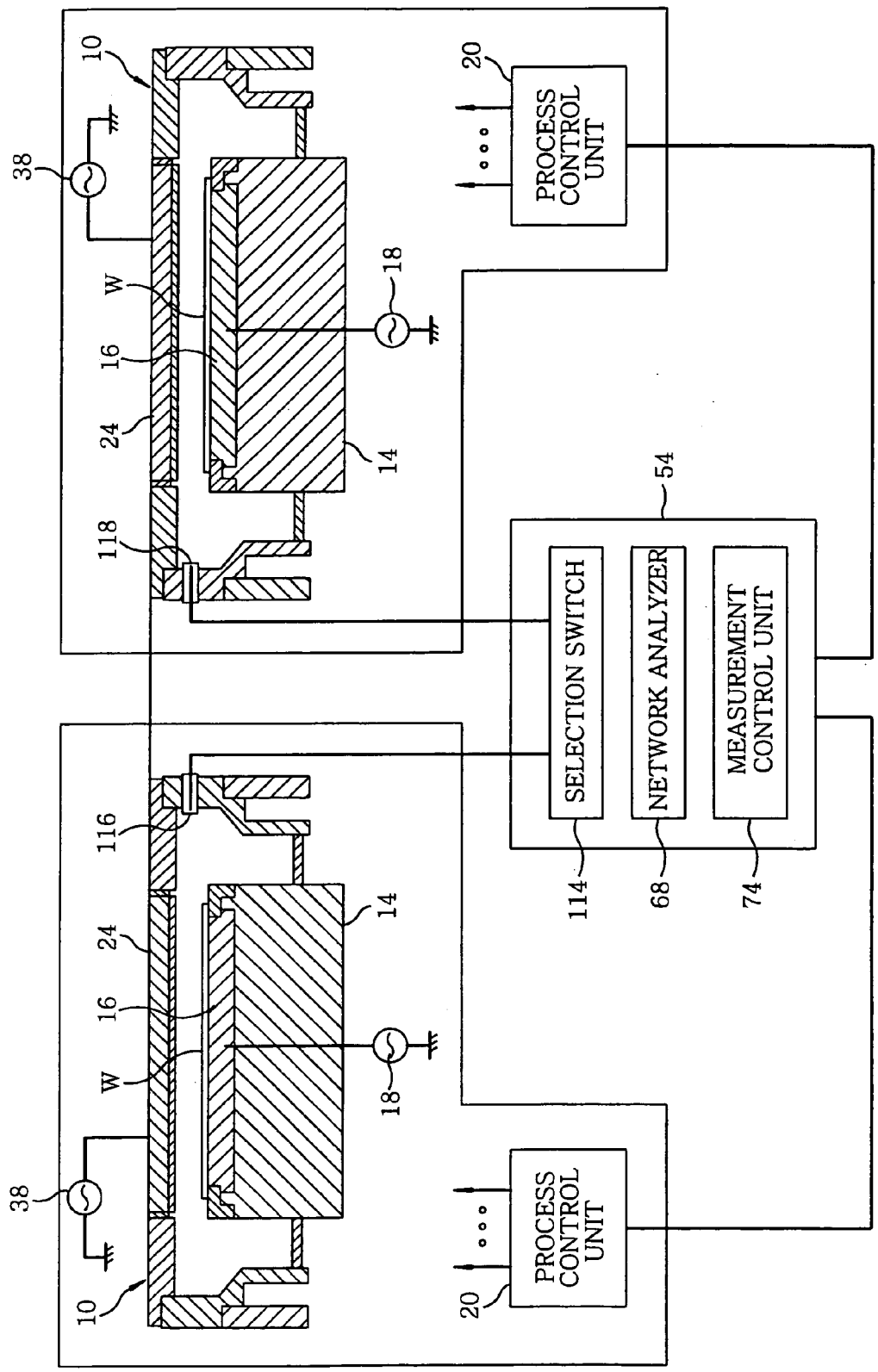
[FIG. 16] provides a configuration of a plasma processing apparatus to which a plasma electron density measuring apparatus is applied in accordance with still another embodiment of the present invention.
Figure 17:
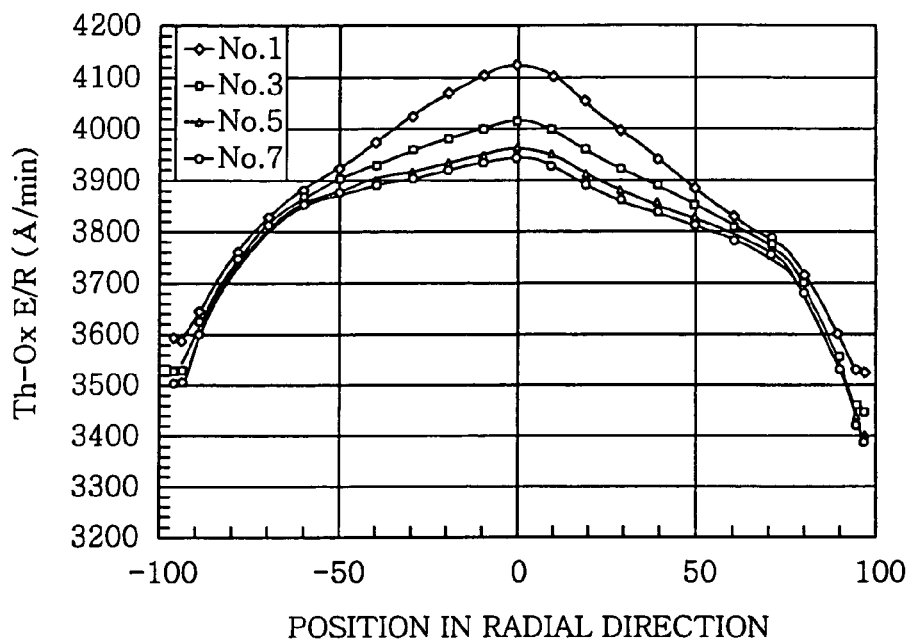
[FIG. 17] is a graph showing an example of a situation in which an etching rate is gradually decreased and stabilized at respective locations on a wafer in the etching cycle of seasoning.
Figure 18:
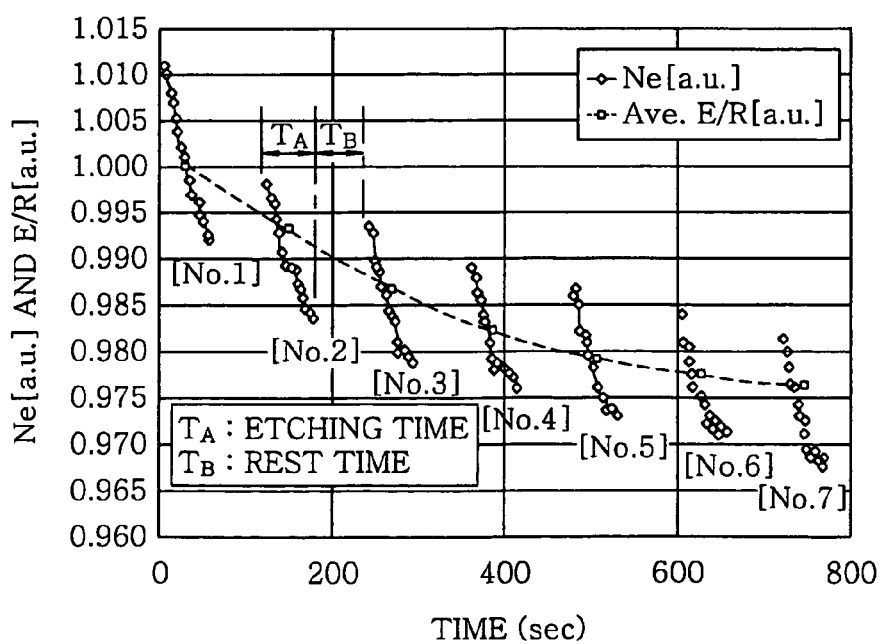
[FIG. 18] depicts time variations of the average value of etching rates and electron density.
Figure 19:
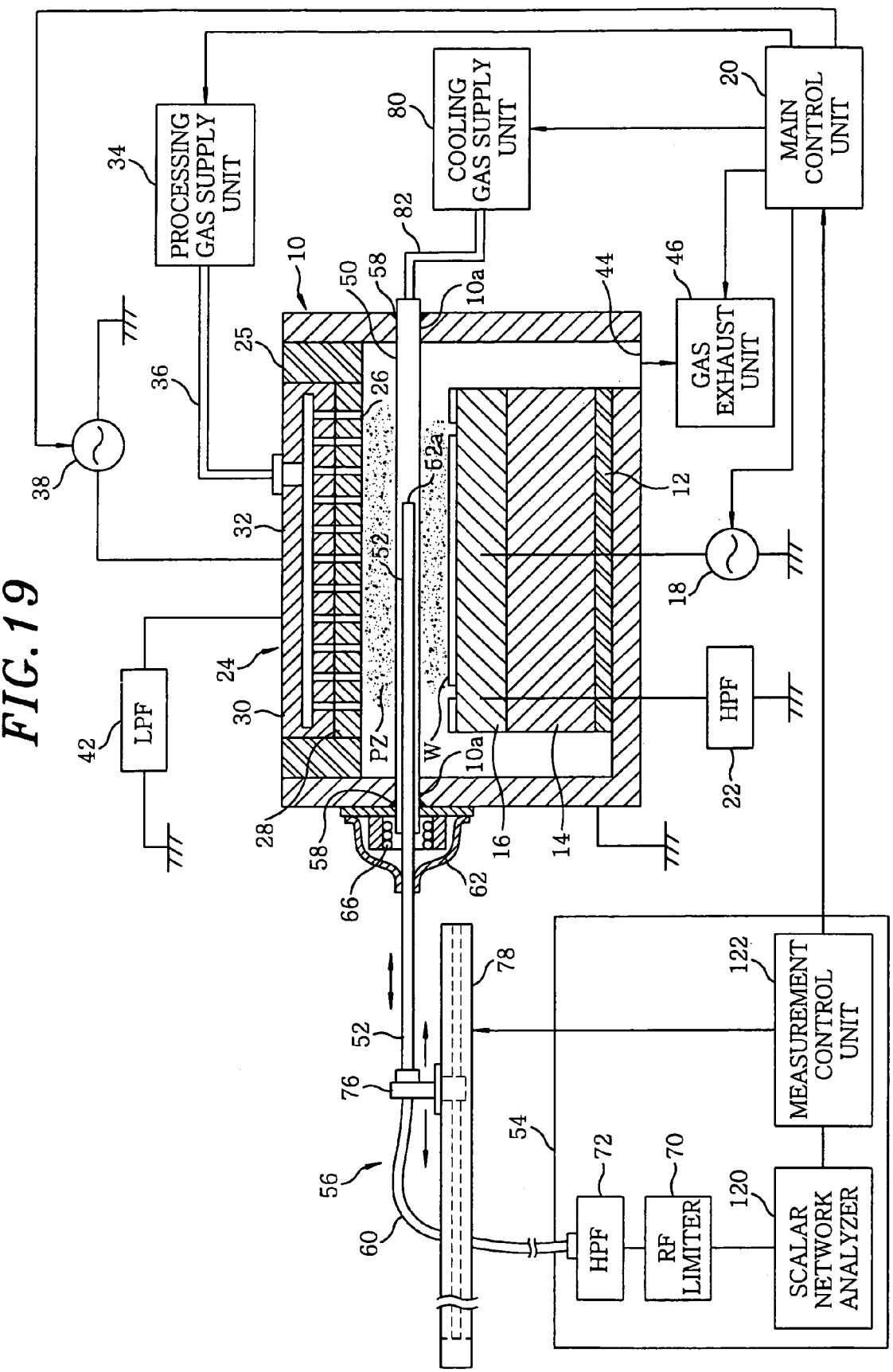
[FIG. 19] charts a configuration of a plasma processing apparatus to which plasma monitoring method and apparatus are applied in accordance with a second embodiment of the present invention.
Figure 20:
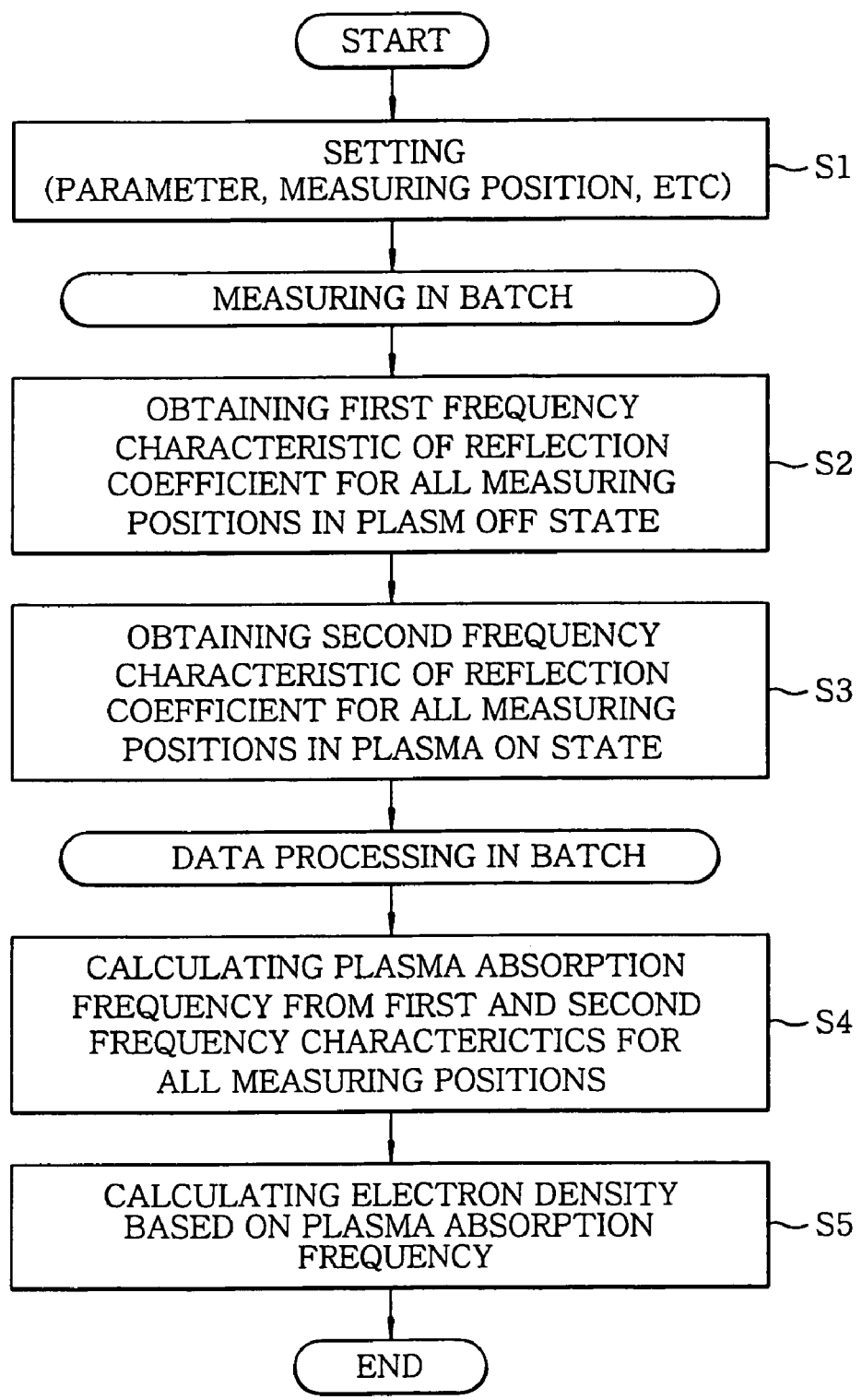
[FIG. 20] is a flowchart showing a schematic sequence of plasma monitoring process in an embodiment.
Figure 21:
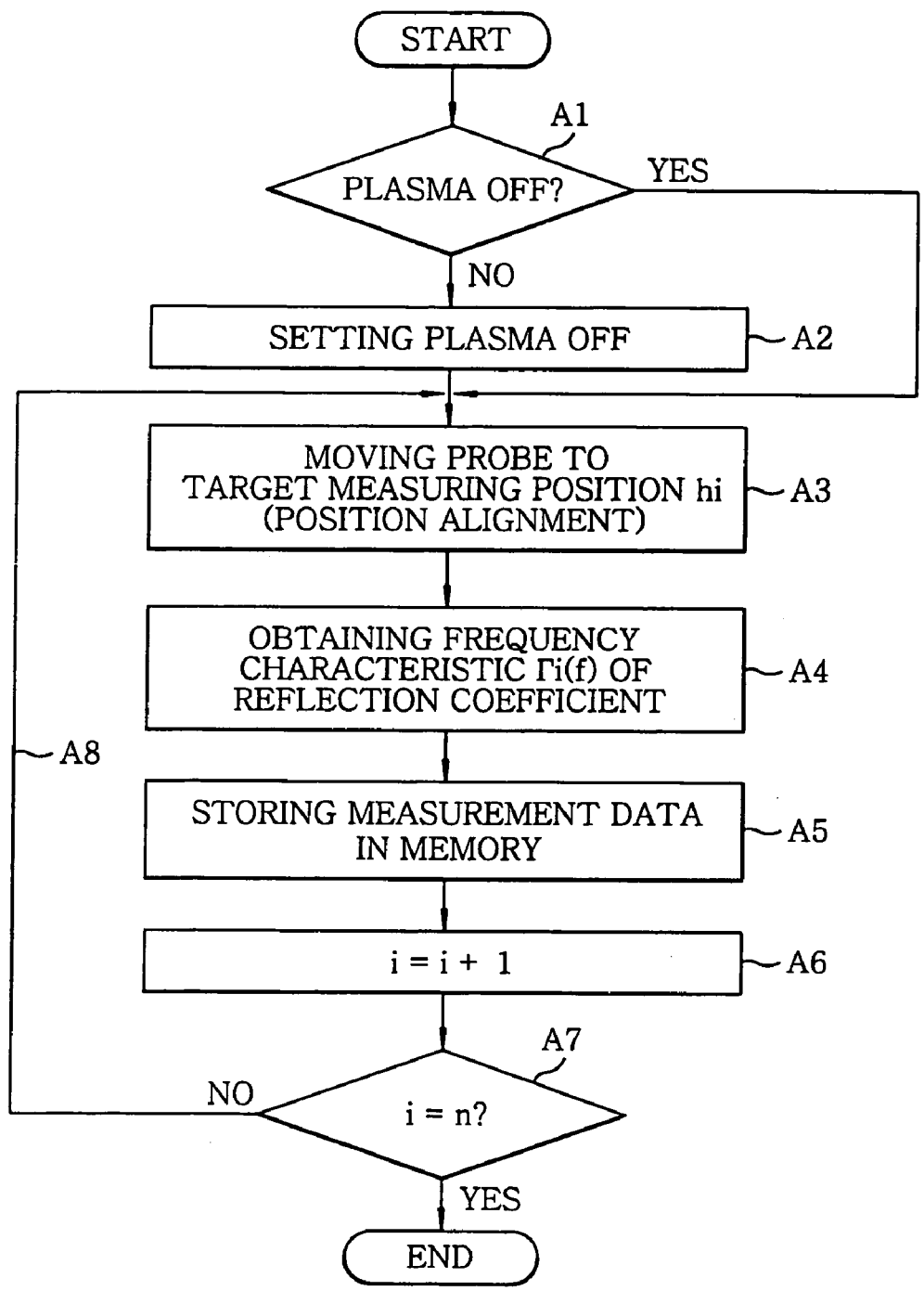
[FIG. 21] is a flowchart showing a detailed sequence of a first batch measurement process in the plasma monitoring process of the second embodiment.
Figure 22:
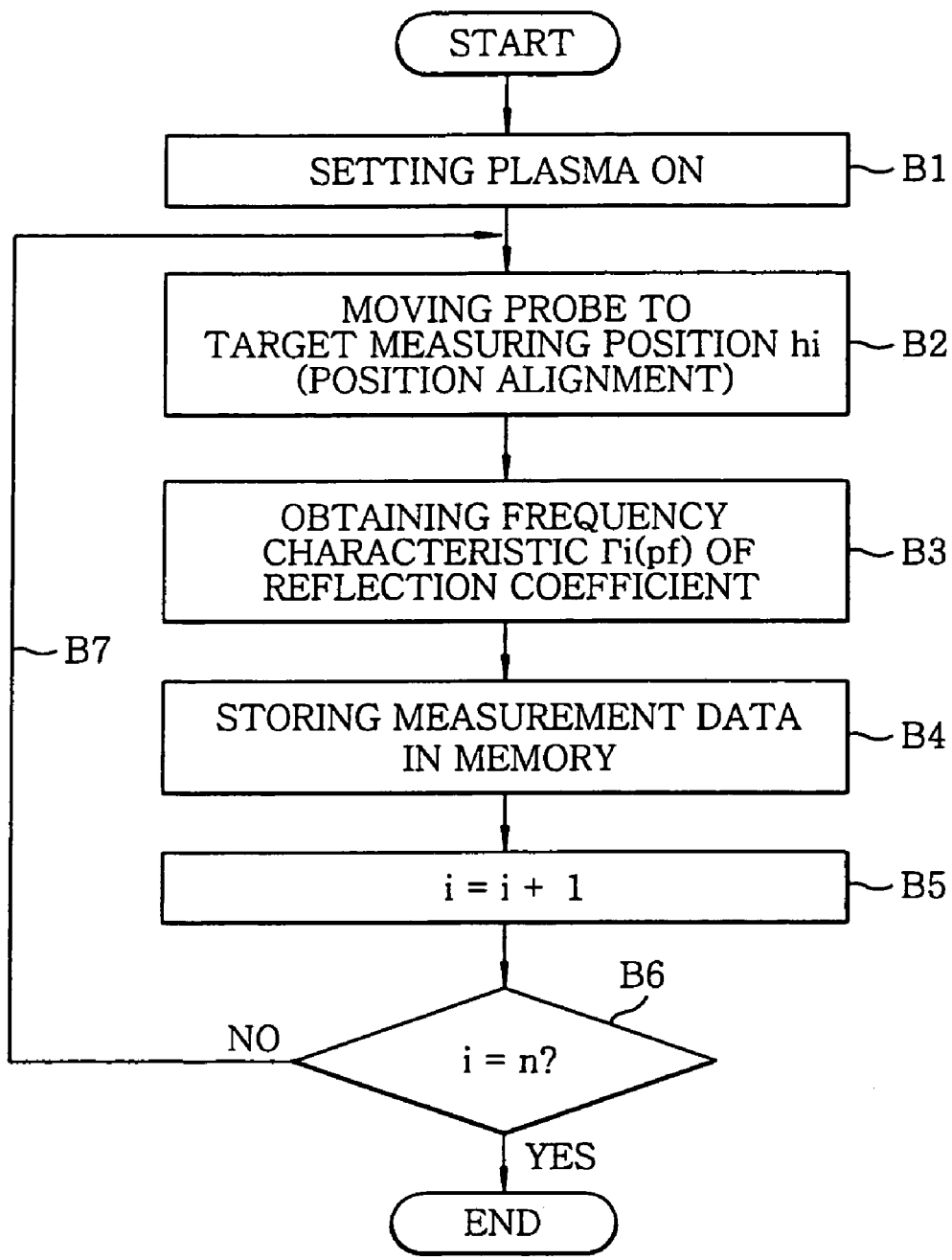
[FIG. 22] is a flowchart showing a detailed sequence of a second batch measurement process in the plasma monitoring process of the second embodiment.
Figure 23:
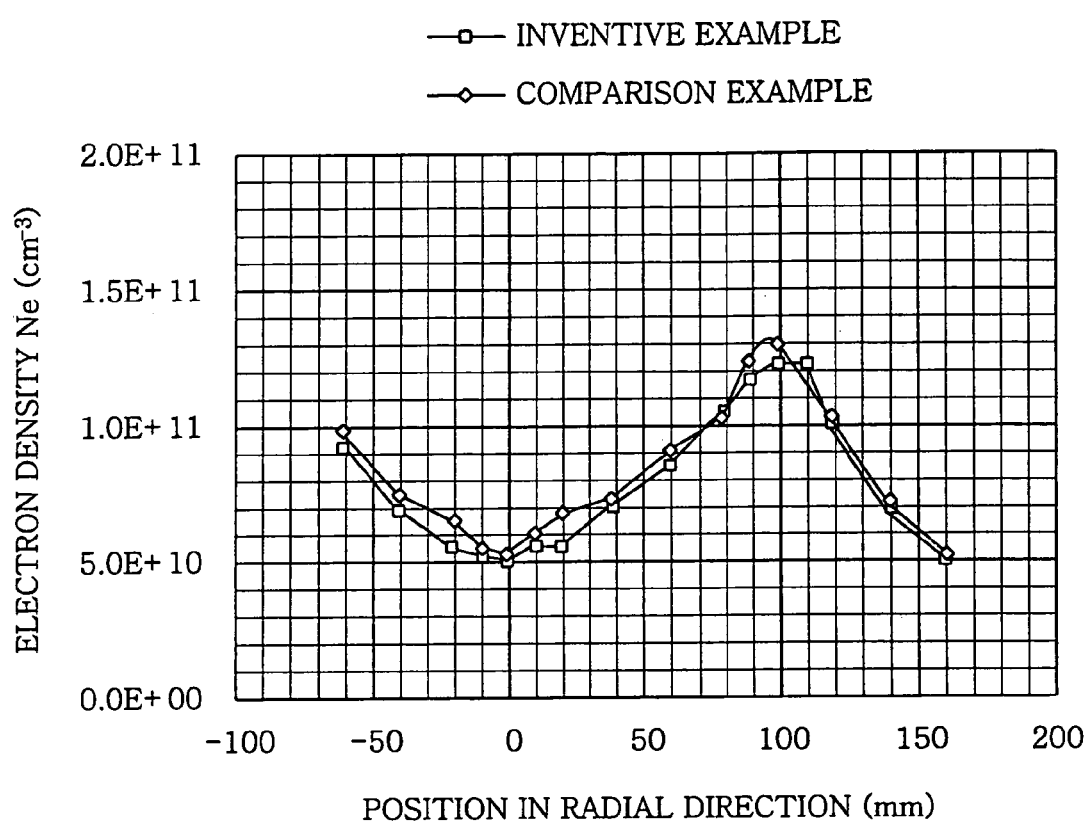
[FIG. 23] is a graph showing an example of the spatial distribution characteristics of electron density obtained in the second embodiment while comparing the example with a comparative example.
Figure 24:
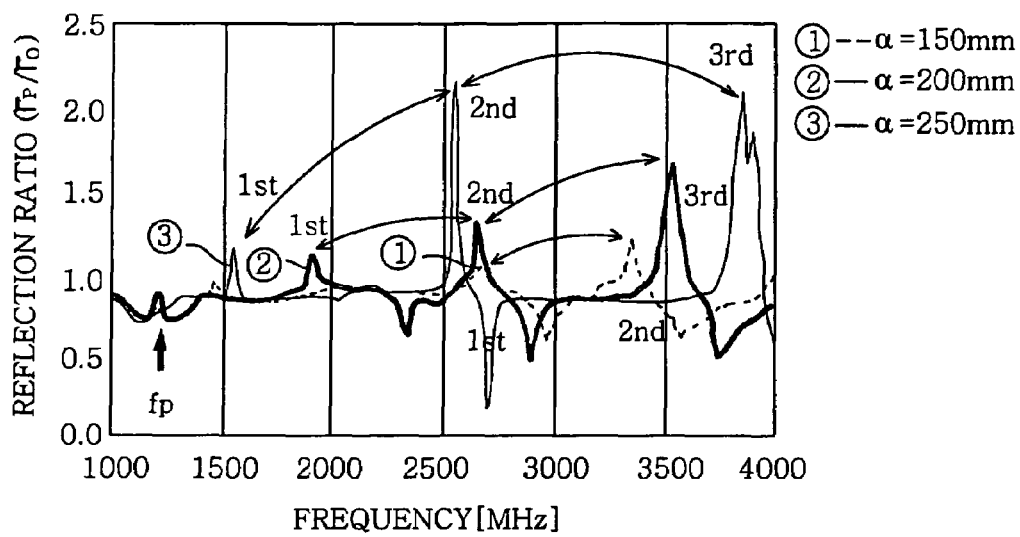
[FIG. 24] charts a graph showing the frequency characteristics of noise peaks in an embodiment.
Figure 25:
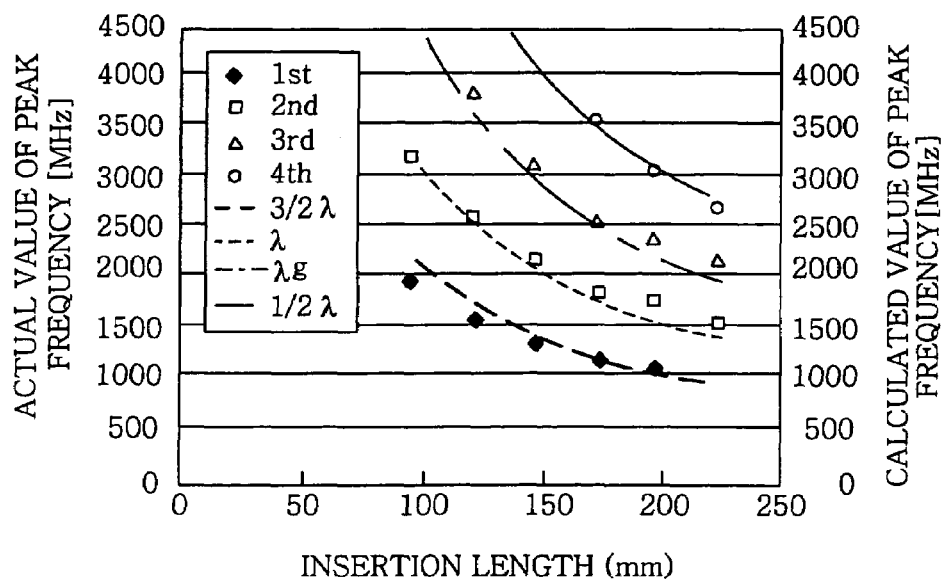
[FIG. 25] exhibits a graph showing the actually measured values and calculated values of standing wave noise depending the insertion length of a probe.
Figure 26A:
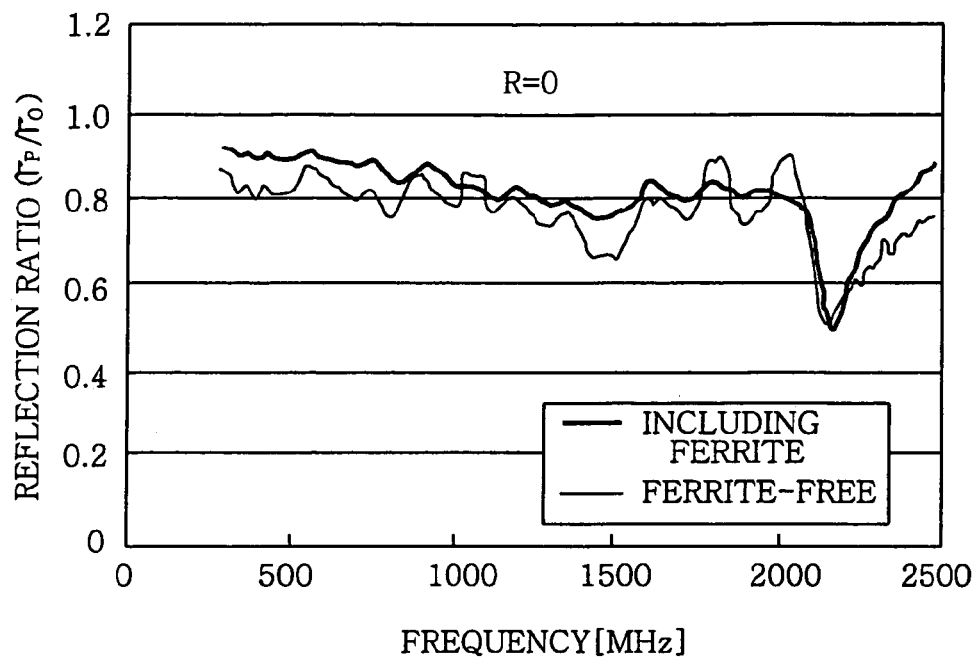
[FIG. 26A] shows a graph of frequency characteristics that represent the noise absorption effect of an electromagnetic wave absorber in an embodiment.
Figure 26B:
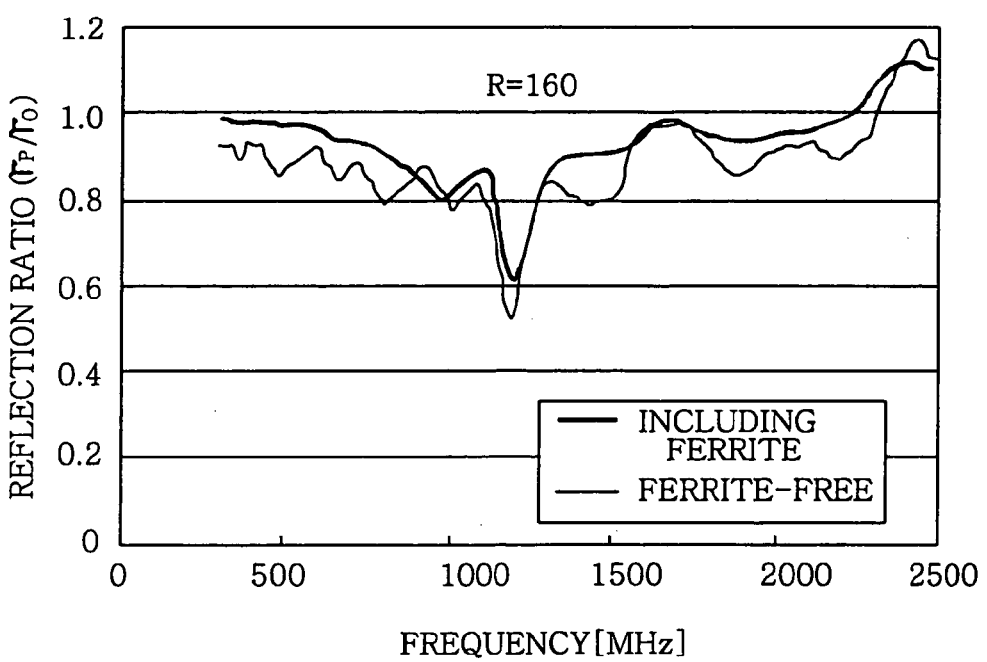
[FIG. 26B] shows a graph of frequency characteristics that represent the noise absorption effect of an electromagnetic wave absorber in an embodiment.
Figure 28:
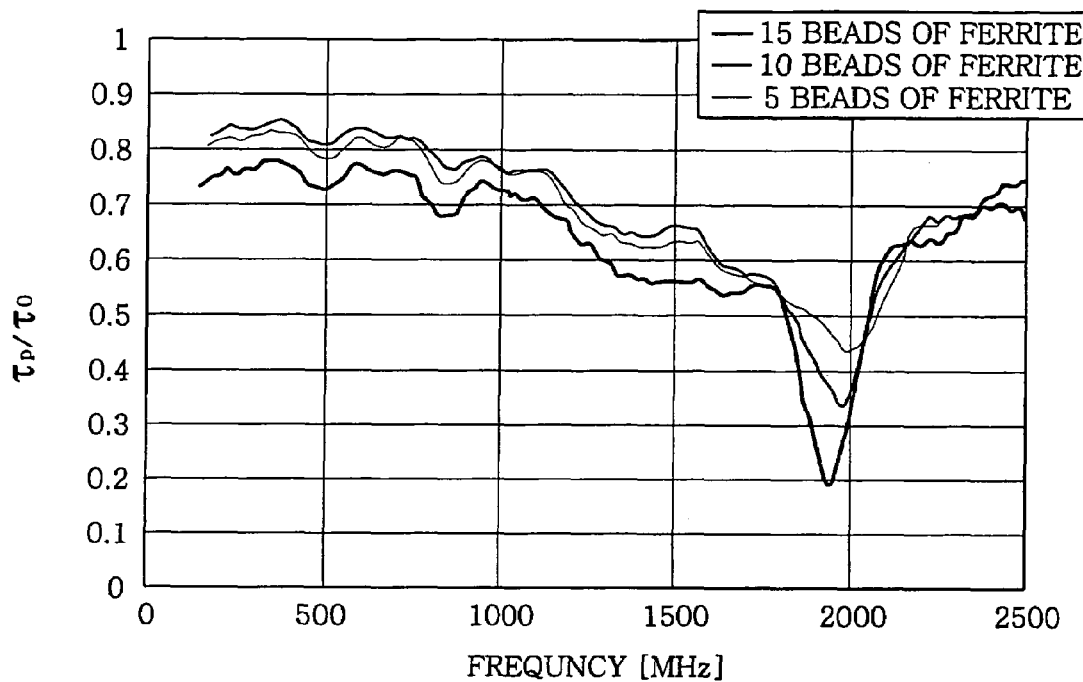
[FIG. 28] illustrates a graph of frequency characteristics that represent a signal increase effect according to the enhancement of an electromagnetic wave absorber in an embodiment.
Figure 29:
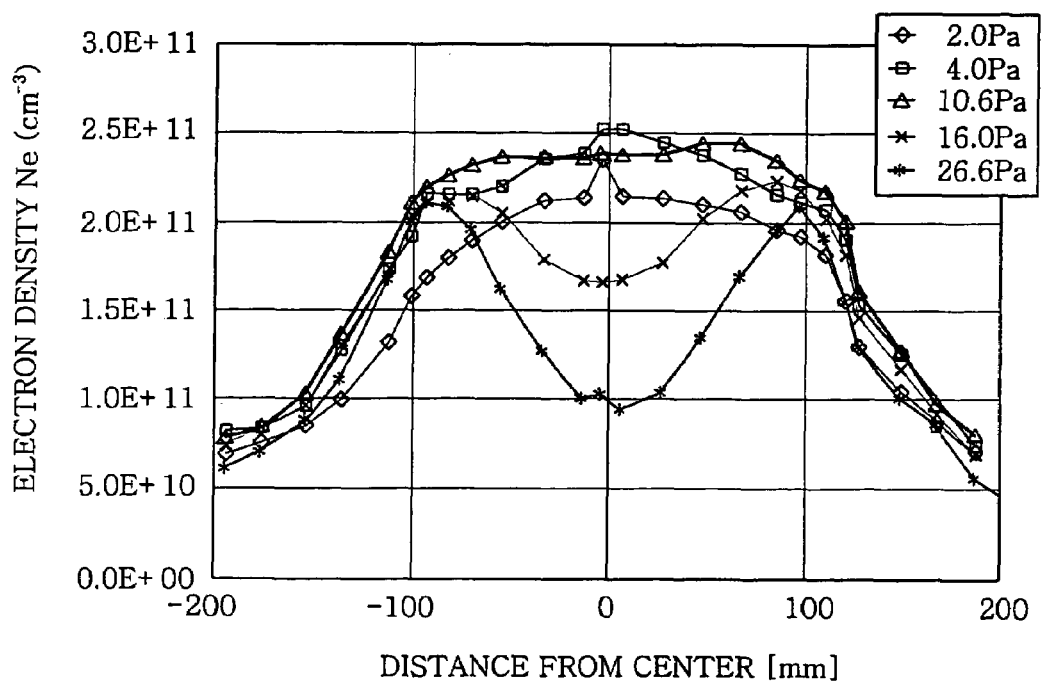
[FIG. 29] charts a graph showing the spatial distribution characteristics of electron density in an embodiment.
Figure 30:
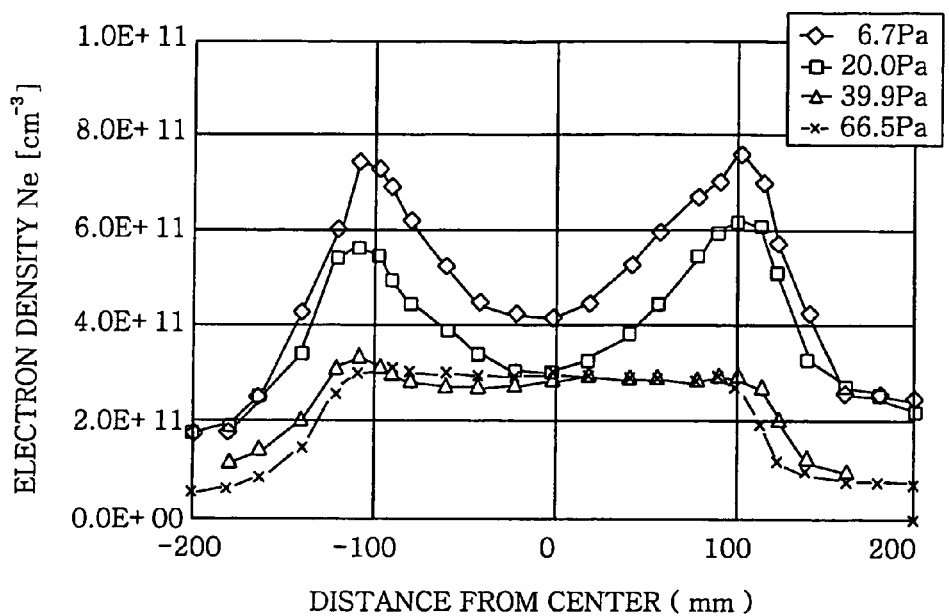
[FIG. 30] charts a graph showing the spatial distribution characteristics of electron density in an embodiment.
Figure 31:
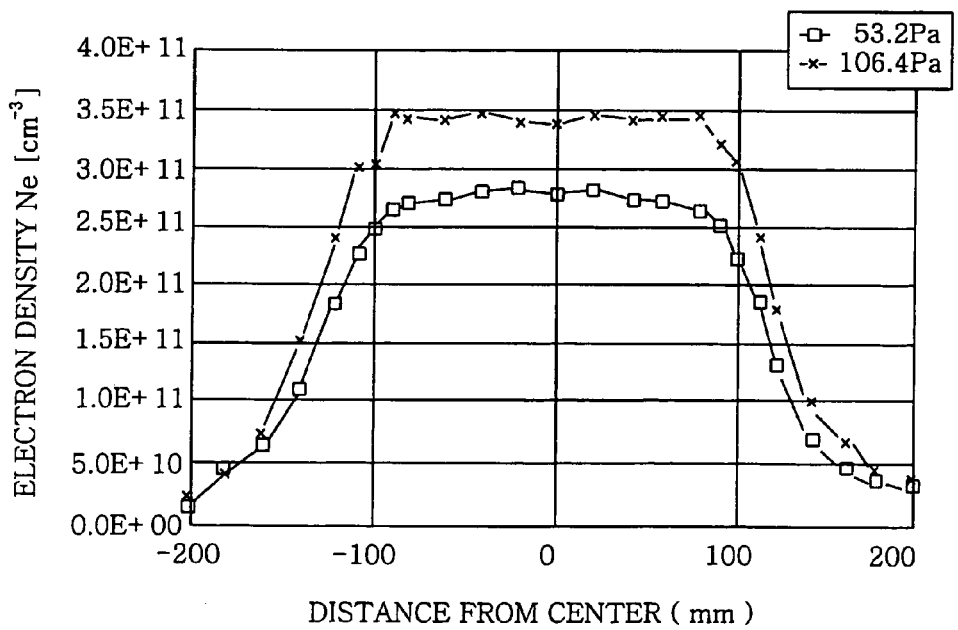
[FIG. 31] charts a graph showing the spatial distribution characteristics of electron density in an embodiment.
Figure 32:
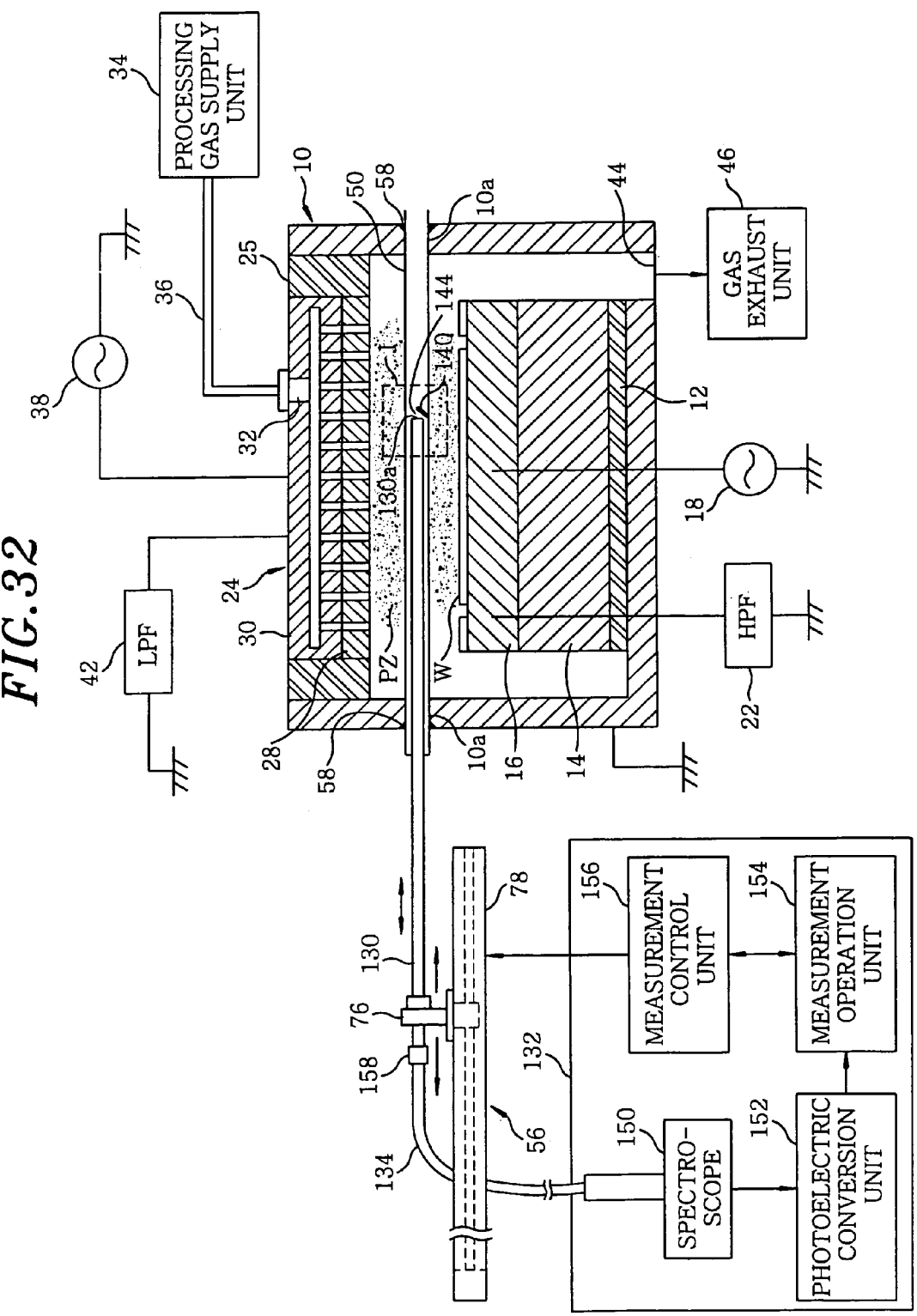
[FIG. 32] provides a configuration of a plasma processing apparatus to which plasma light emission measuring method and apparatus are applied in accordance with a third embodiment of the present invention.
Figure 33:
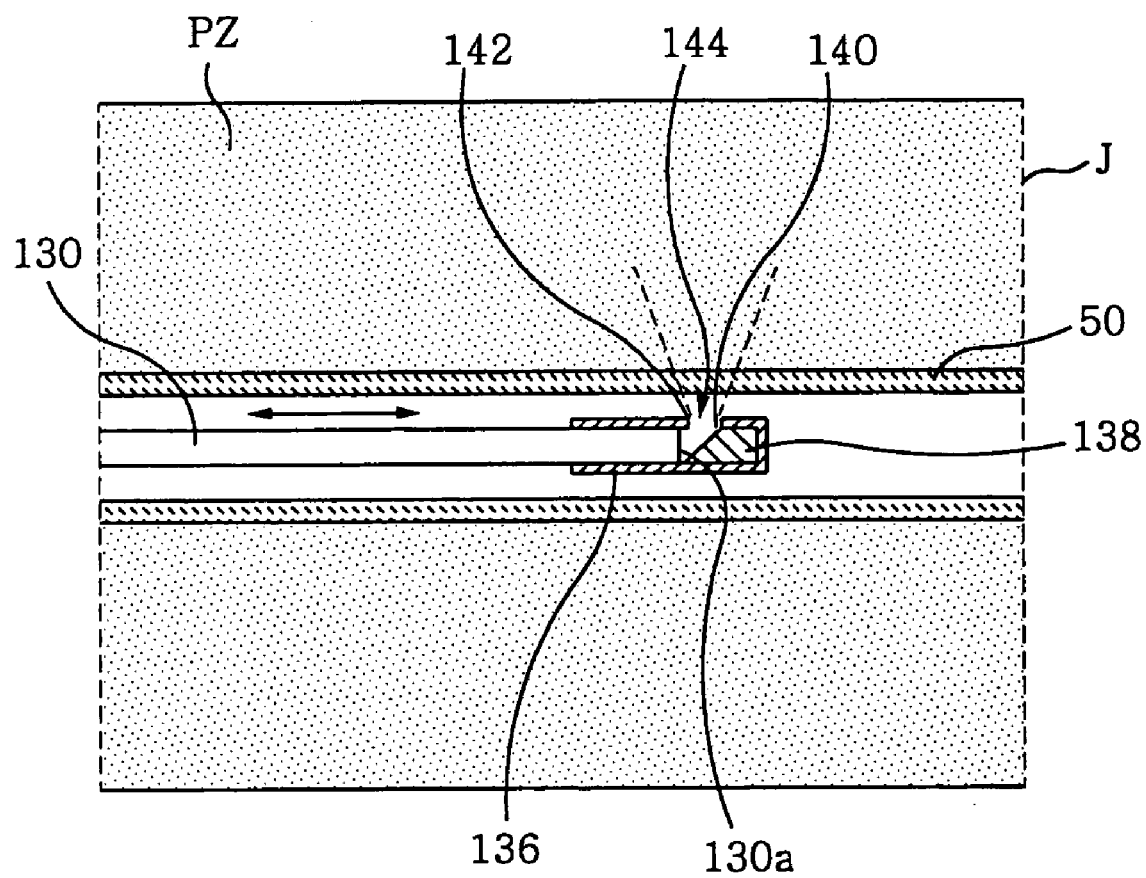
[FIG. 33] exhibits a partially enlarged section showing constructions and operations of principal parts of a probe in the third embodiment.
Figure 34A:
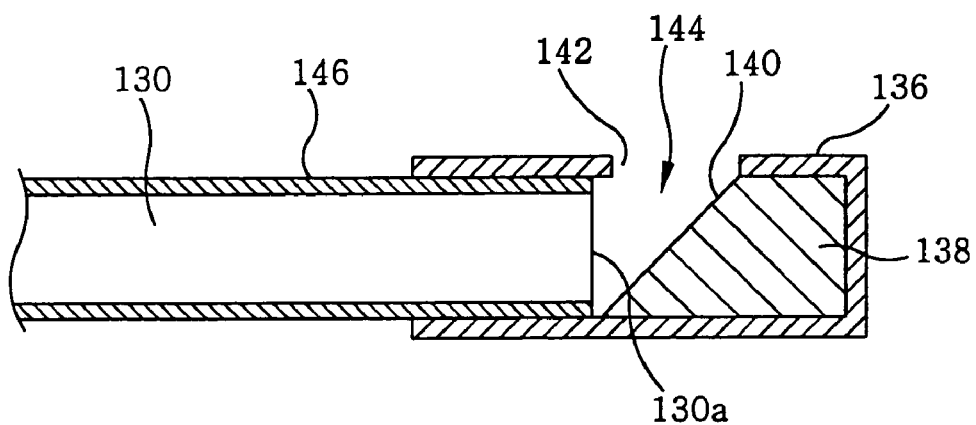
[FIG. 34A] shows a partially enlarged section showing a structure of a probe in another embodiment.
Figure 34B:
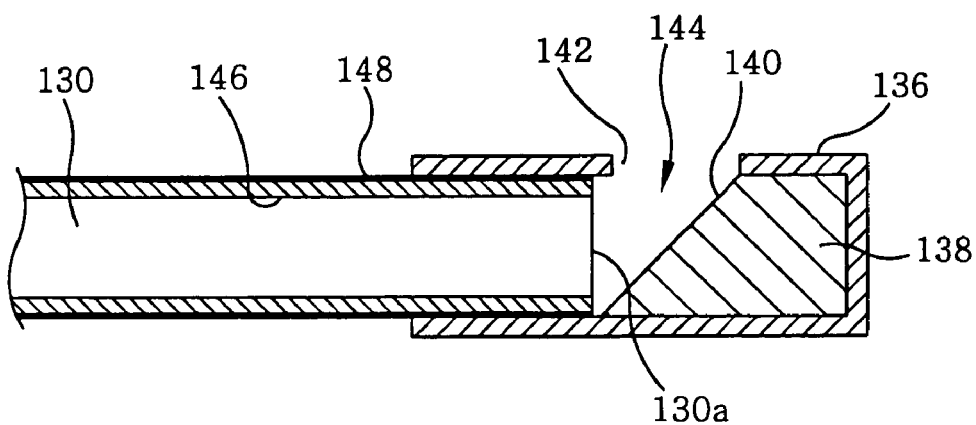
[FIG. 34B] shows a partially enlarged section showing a structure of a probe in another embodiment.
Figure 35:
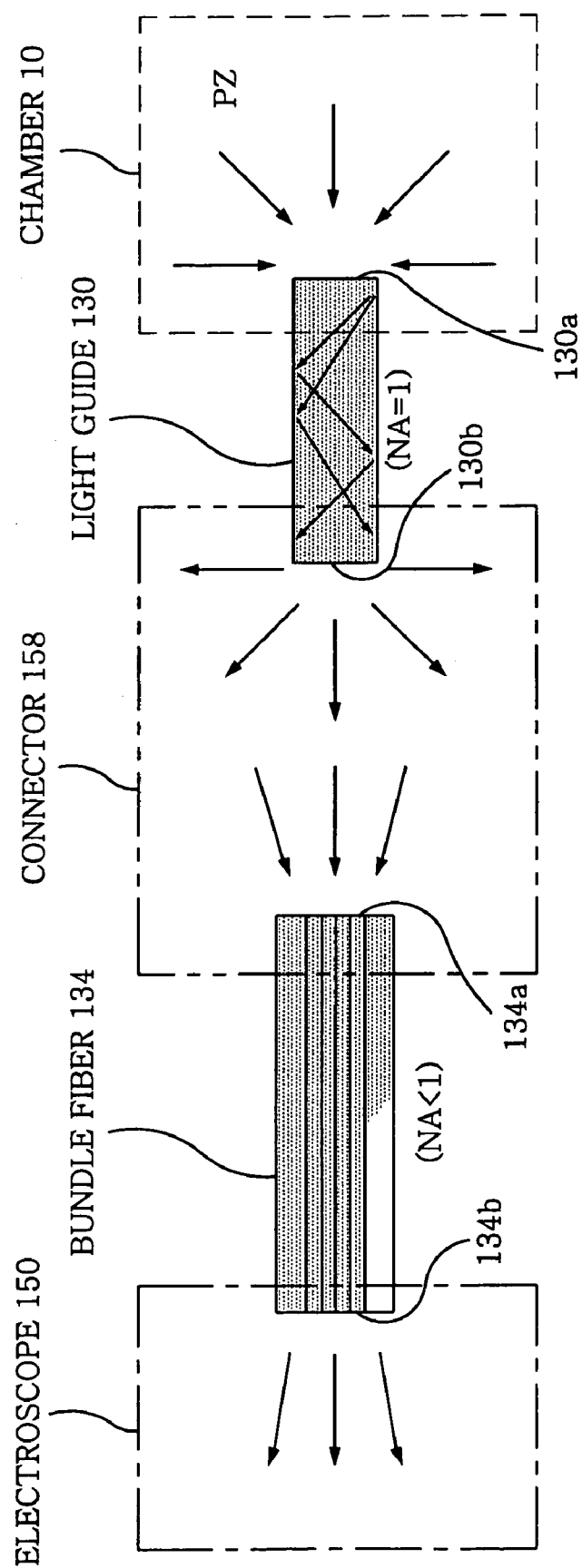
[FIG. 35] is a diagram schematically showing an operation of a probe and a bundle fiber in the third embodiment.
Figure 36:
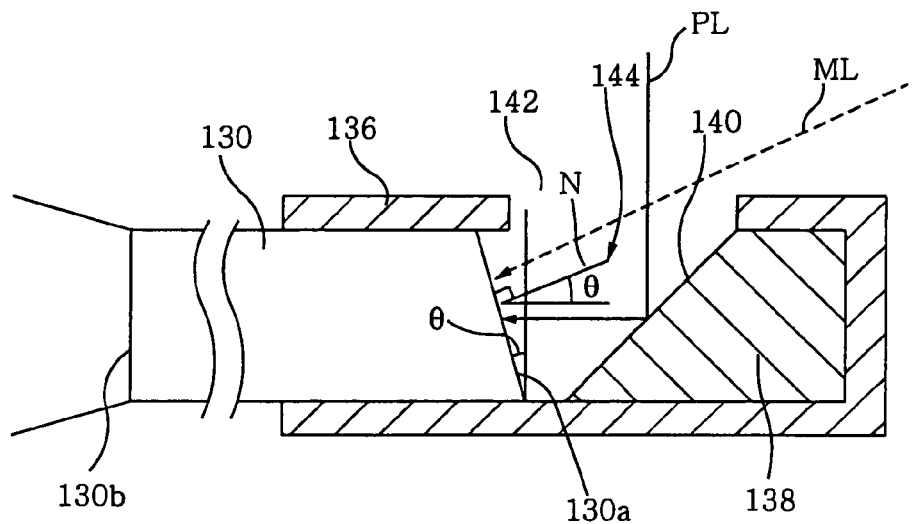
[FIG. 36] is a partially enlarged section showing a construction and operation of a probe in an embodiment.
Figure 37:
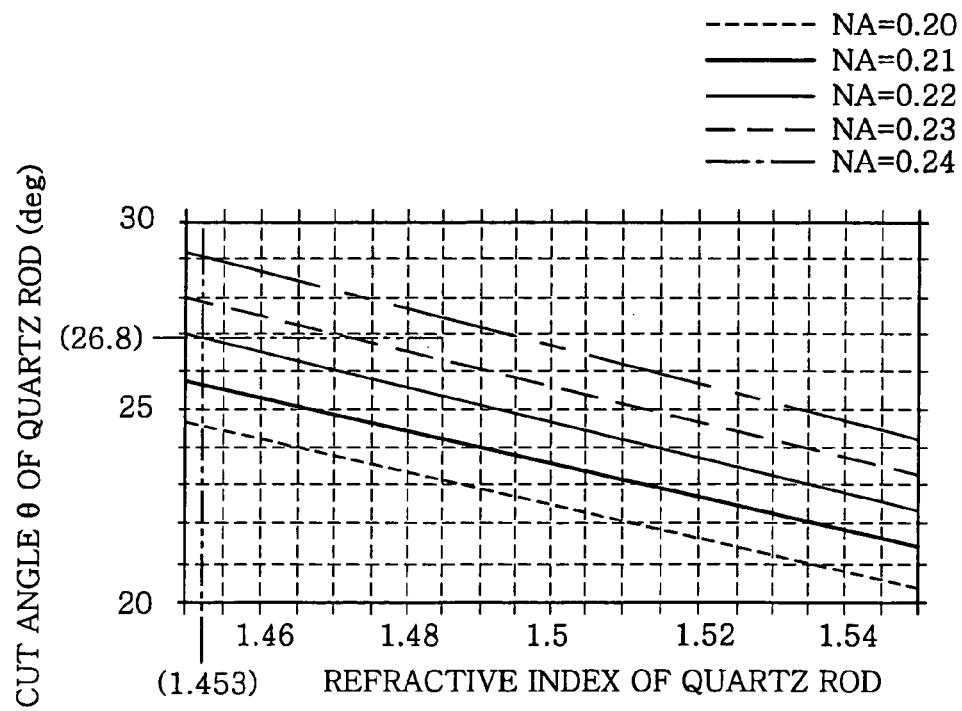
[FIG. 37] charts a graph of a relationship between refractive indexes and cut angles of a quartz rod used in the probe in the third embodiment.
Figure 38A:
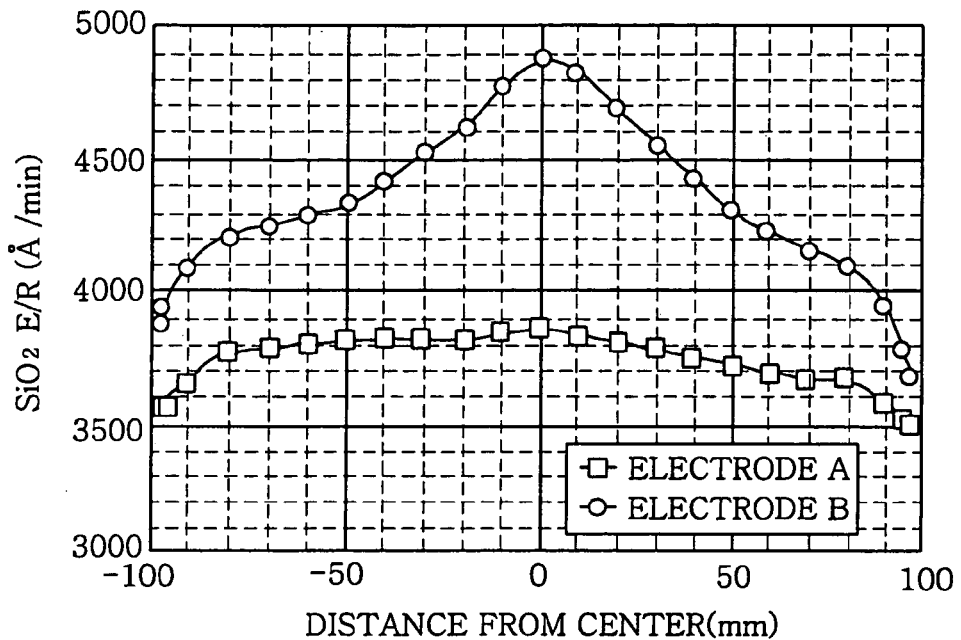
[FIG. 38A] charts a graph showing an example of a correlation between the intra-surface distribution of etching rates and the spatial distribution of plasma light emission in the third embodiment.
Figure 38B:
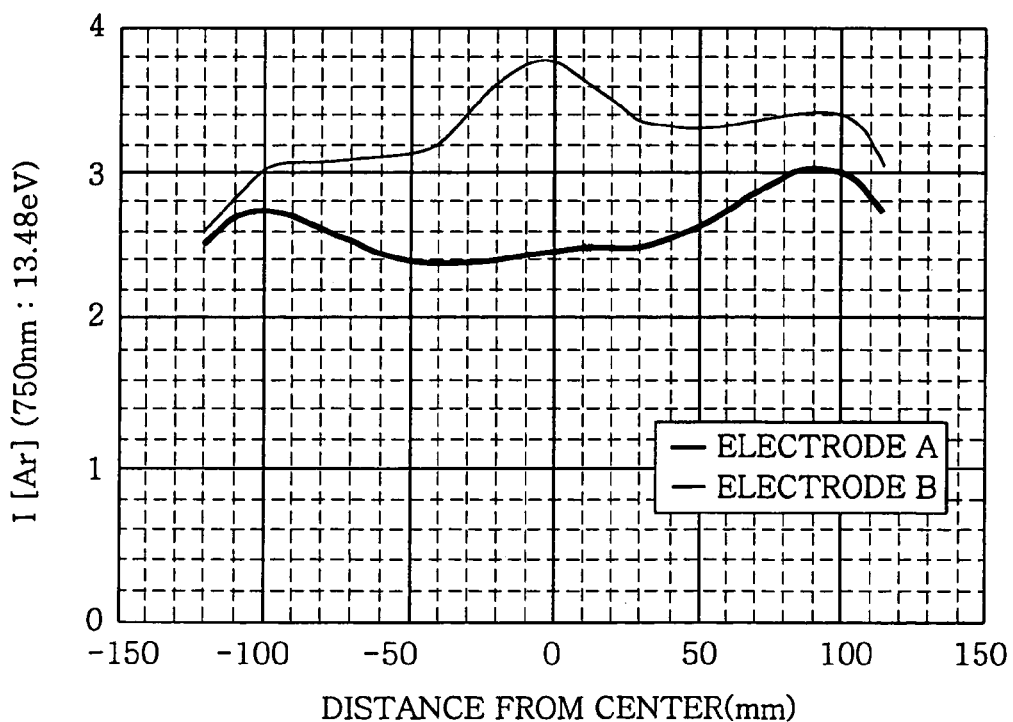
[FIG. 38B] charts a graph showing an example of a correlation between the intra-surface distribution of etching rates and the spatial distribution of plasma light emission in the third embodiment.
Figure 39A:
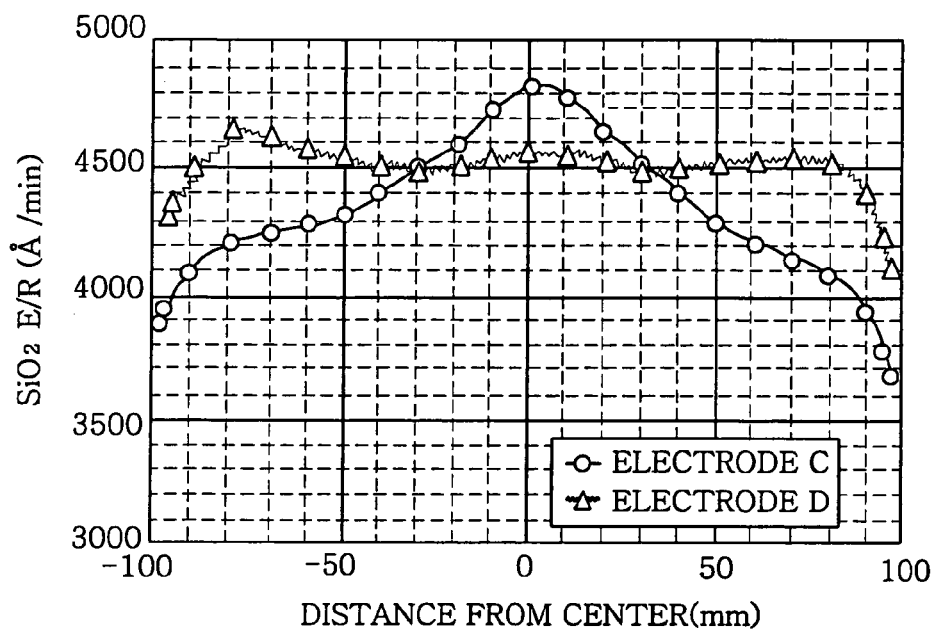
[FIG. 39A] charts a graph showing an example of a correlation between the intra-surface distribution of etching rates and the spatial distribution of plasma light emission in the third embodiment.
Figure 39B:
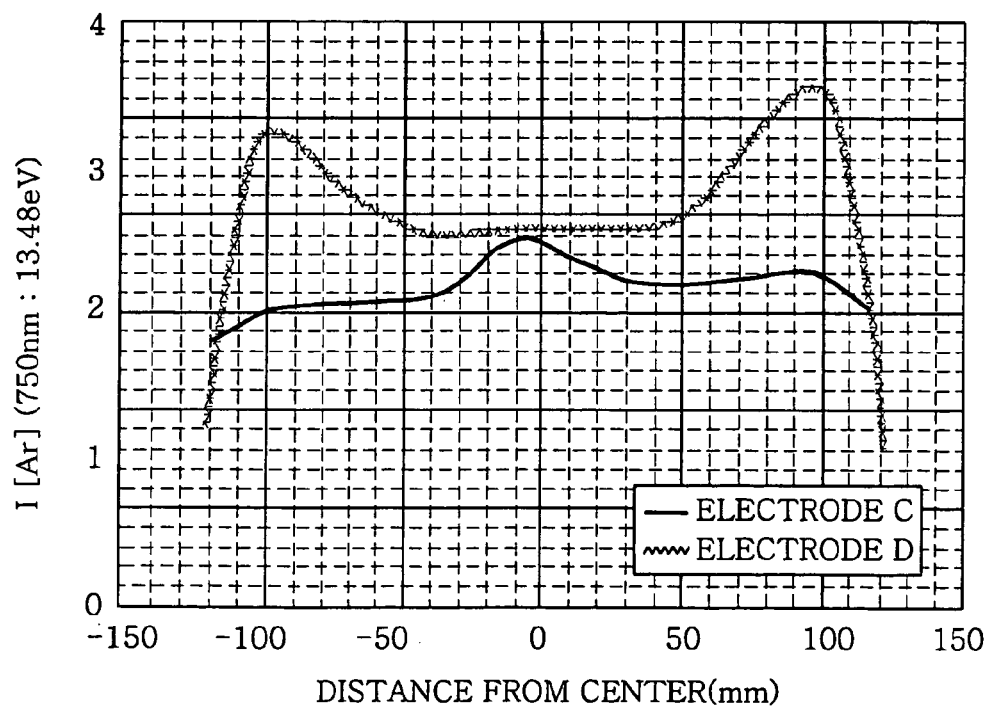
[FIG. 39B] charts a graph showing an example of a correlation between the intra-surface distribution of etching rates and the spatial distribution of plasma light emission in the third embodiment.
Figure 40A:
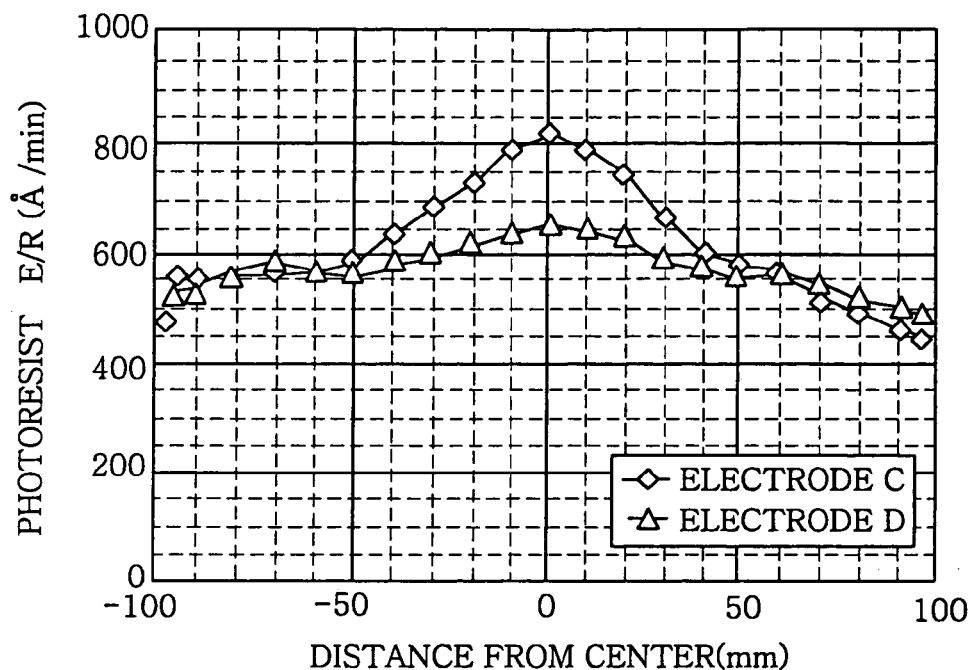
[FIG. 40A] charts a graph showing an example of a correlation between the intra-surface distribution of etching rates and the spatial distribution of plasma light emission in the third embodiment.
Figure 40B:
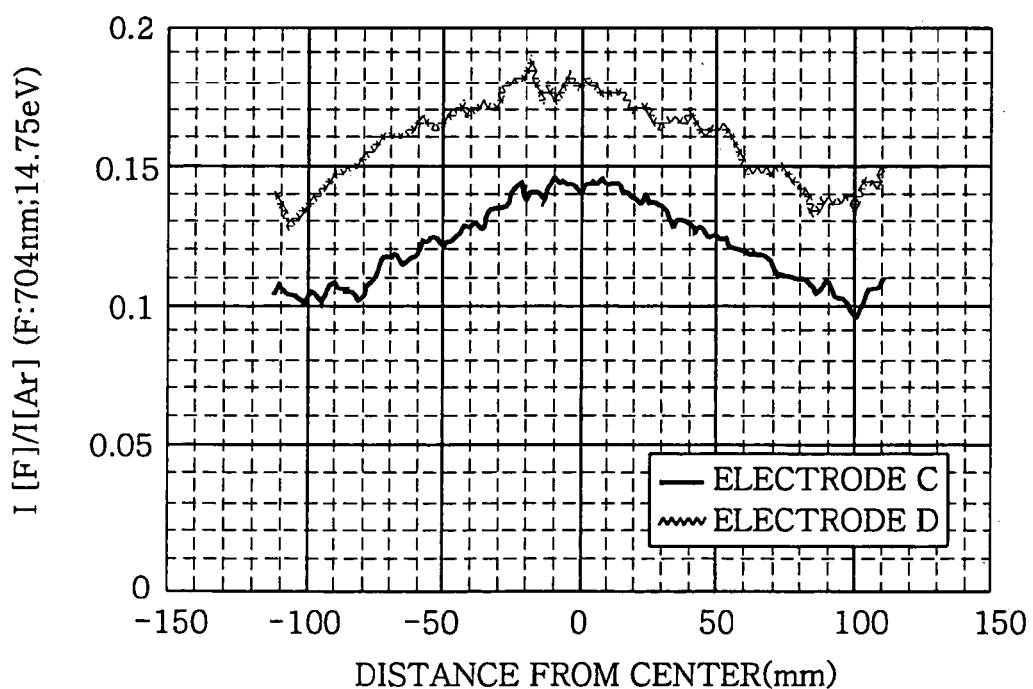
[FIG. 40B] charts a graph showing an example of a correlation between the intra-surface distribution of etching rates and the spatial distribution of plasma light emission in the third embodiment.
Figure 41:
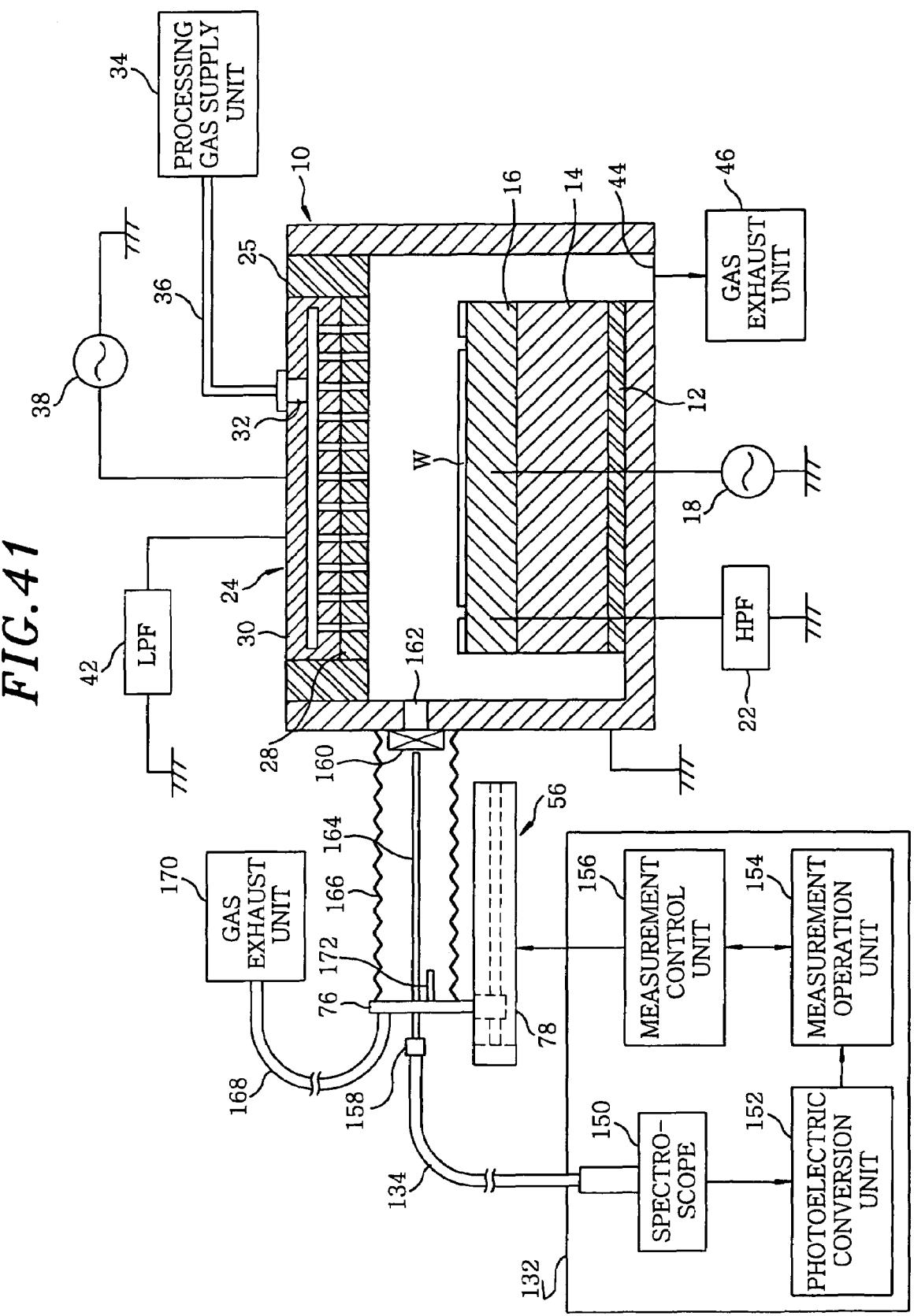
[FIG. 41] describes a configuration of a plasma processing apparatus to which plasma light emission measuring method and apparatus are applied in accordance with another embodiment of the present invention.
Figure 42:
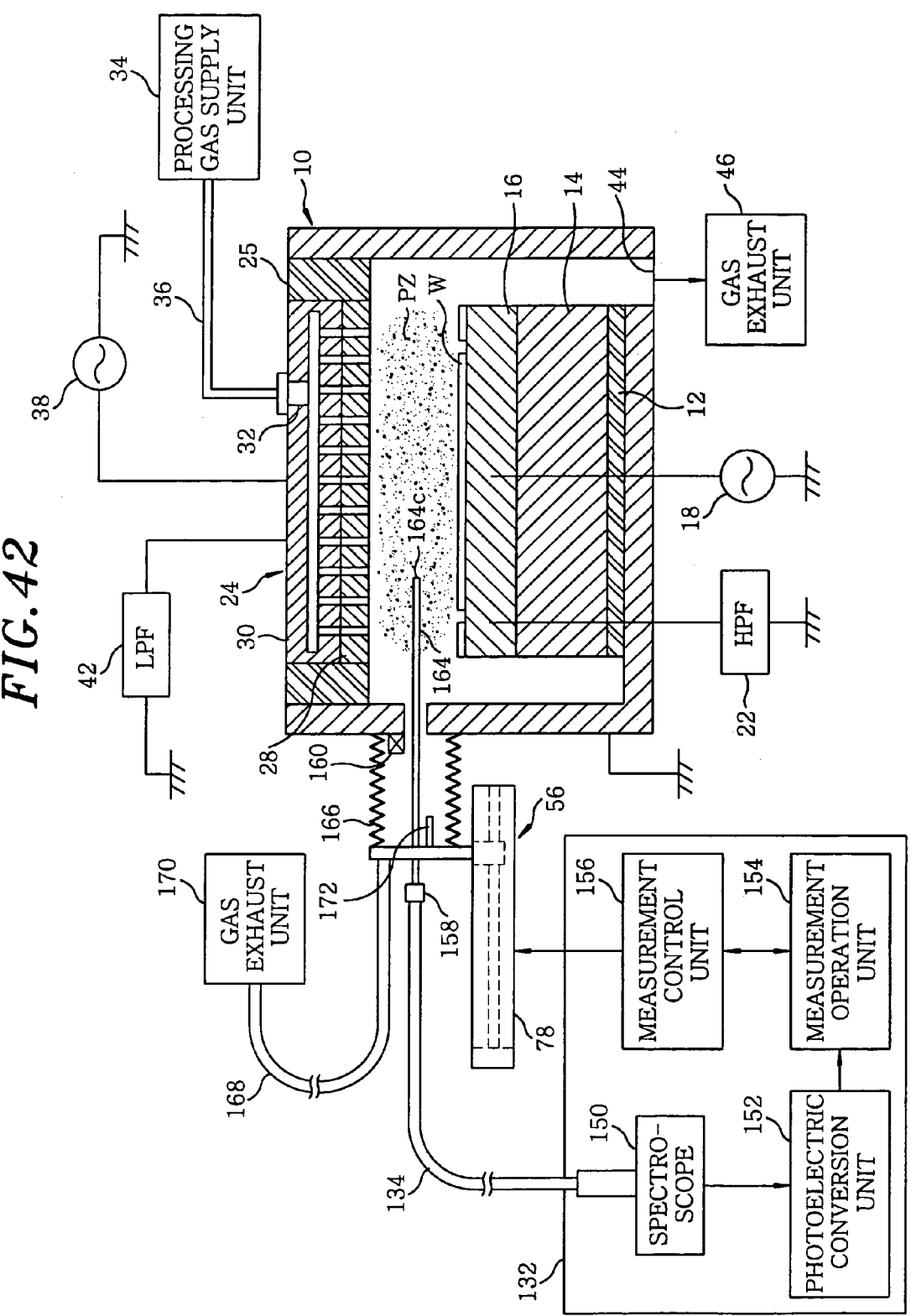
[FIG. 42] shows a state of plasma spectroscopic measurement in the plasma processing apparatus of FIG. 41.
Figure 43:
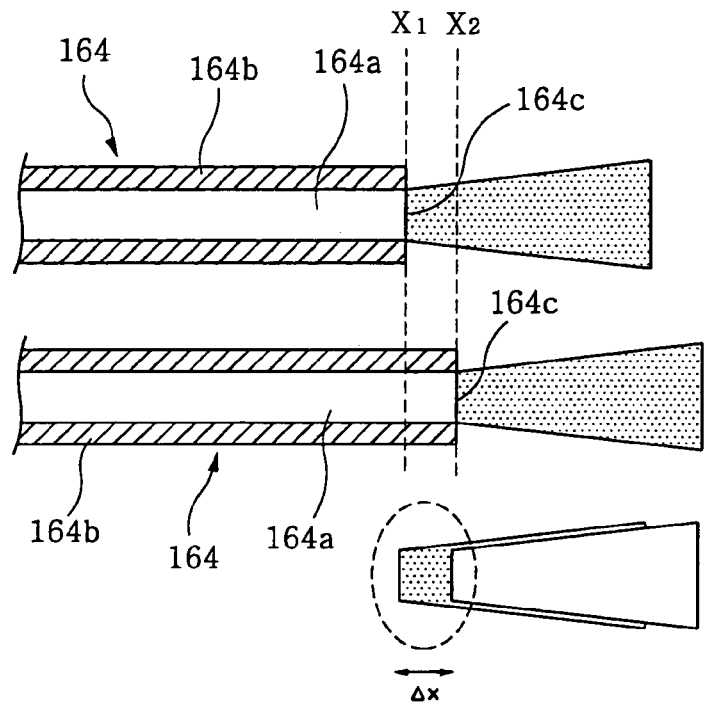
[FIG. 43] is a diagram showing an operation of the plasma light emission measuring apparatus of FIG. 41.
Figure 44:
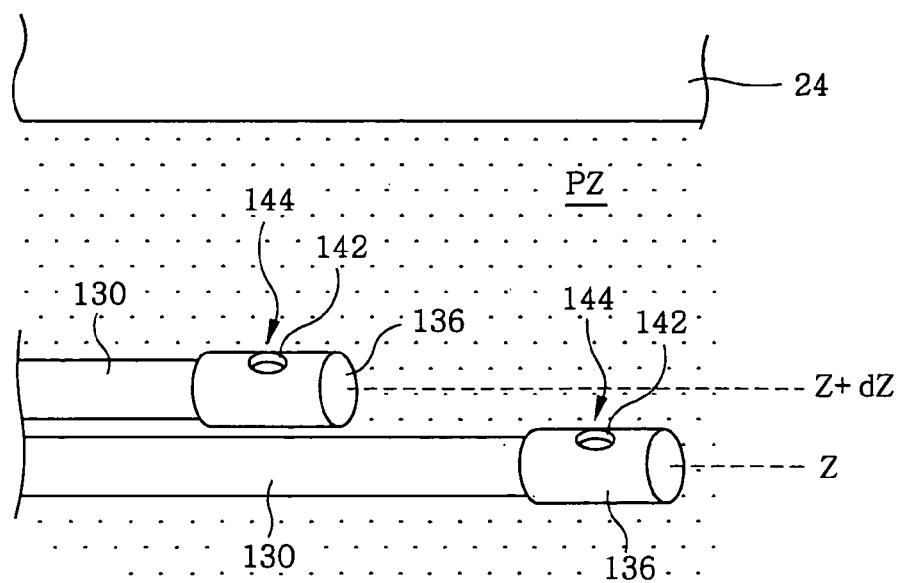
[FIG. 44] is a diagram showing a plasma light emission measuring method in accordance with another embodiment.
Figure 45:
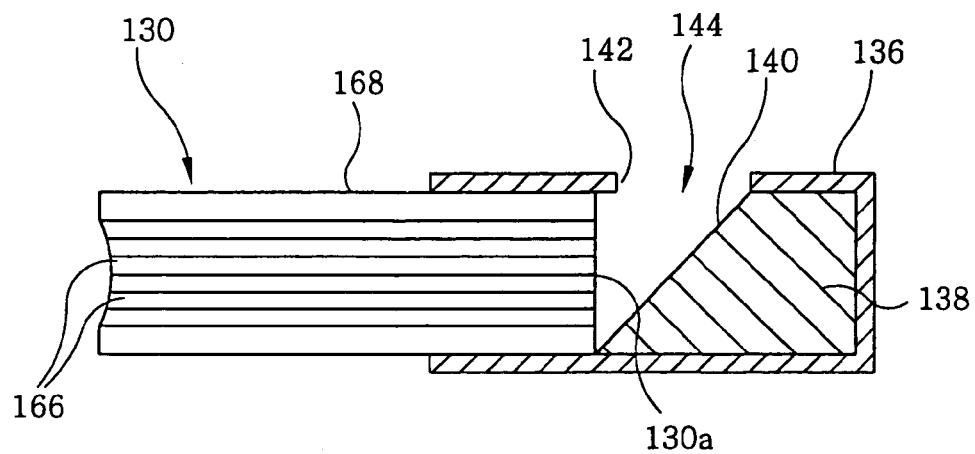
[FIG. 45] is a diagram showing a configuration of principal parts of an optical transmission probe in accordance with a variant.
Figure 46:
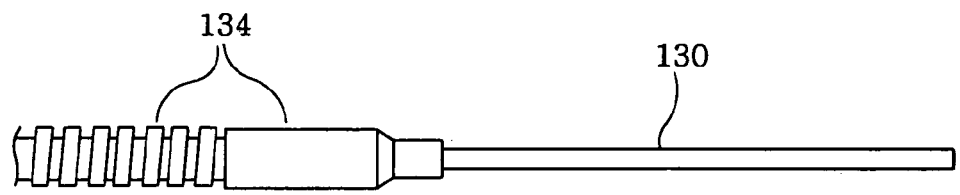
[FIG. 46] is a diagram showing a configuration of principal parts of an optical transmission probe in accordance with a variant.
Figure 47:
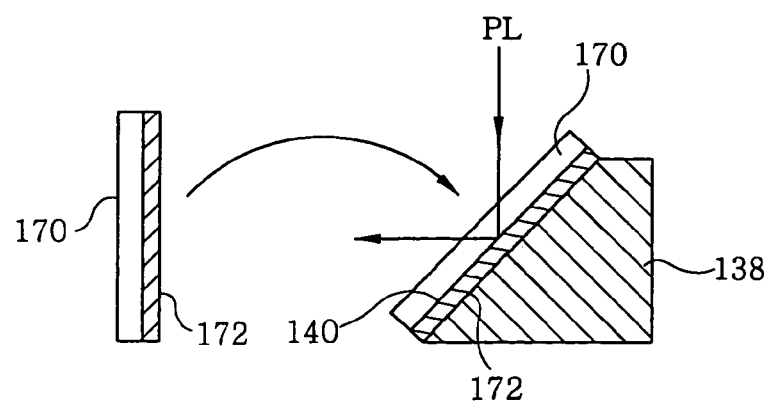
[FIG. 47] is a diagram showing a configuration of principal parts of an optical transmission probe in accordance with a variant.
Figure 48:
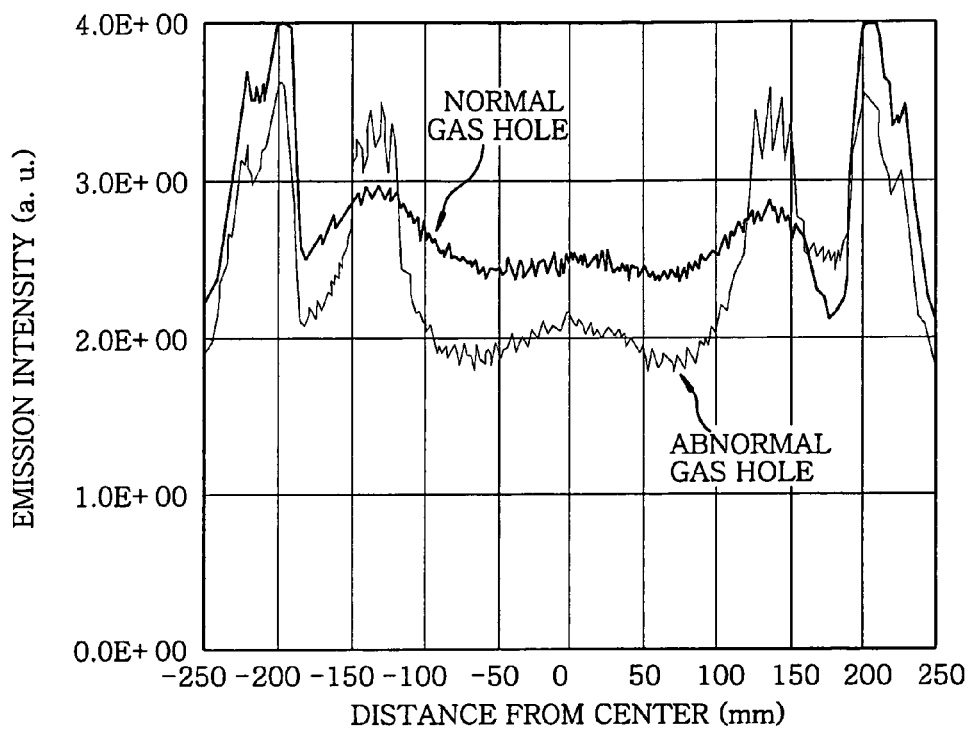
[FIG. 48] is a graph showing the experimental results of a function of monitoring an abnormal discharge in a chamber in accordance with the plasma light emission measuring method of the present invention.
Figure 49:
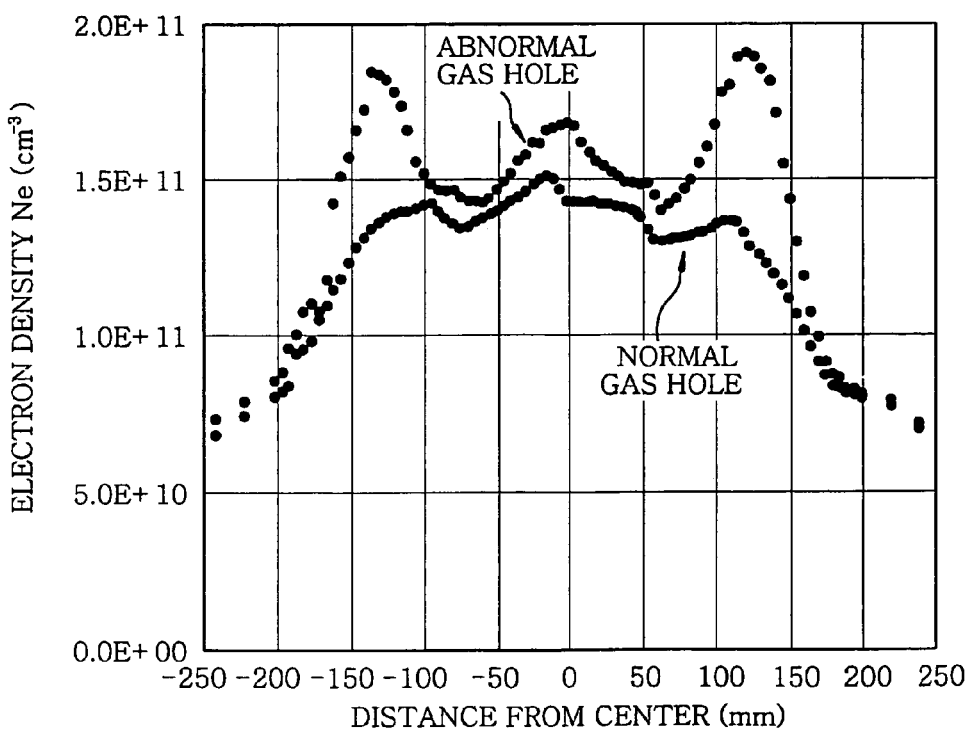
[FIG. 49] is a graph showing the experimental results of a function of monitoring an abnormal discharge in a chamber in accordance with the plasma resonance probe method of the present invention.
Figure 50:
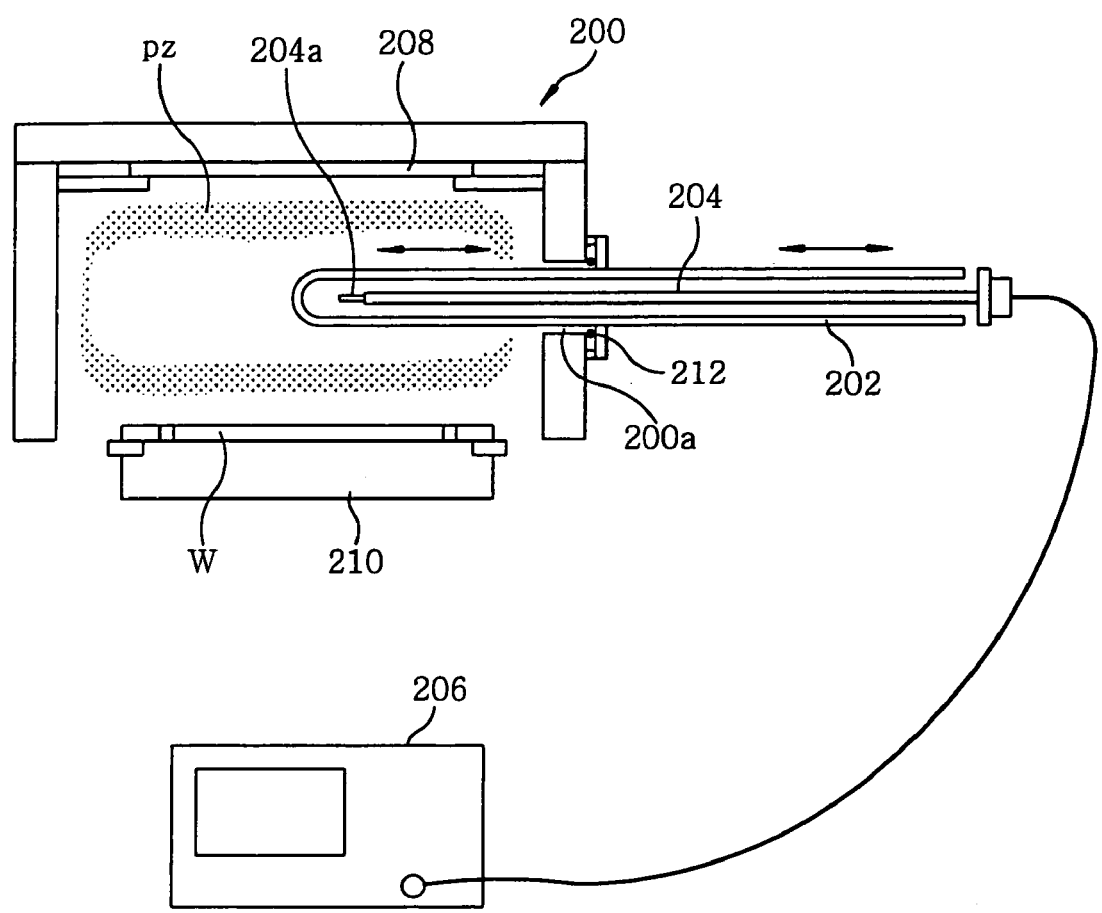
[FIG. 50] illustrates a diagram for explaining a conventional PAP method.

10: chamber
10a: through hole (support)
16: susceptor (lower electrode)
18, 38: high-frequency power supply
20: main control unit
24: upper electrode
34: processing gas supply unit
50: insulating pipe
52: coaxial cable
52a: probe portion (antenna probe)
54: measuring unit
56: linear actuator
58: O-ring
62: grounding conductor
66: electromagnetic wave absorber
68: vector network analyzer
74: measurement control unit
80: cooling gas supply unit
82: gas pipe
84: reflection coefficient measuring unit
90: imaginary part memory
92: resonance frequency determining unit
94: electron density operation unit
100, 102, 104: probe unit
108: window member
114: selection switch
120: scalar network analyzer
122: measurement control unit
130: optical transmission probe
132: measurement unit
134: bundle fiber
136: cap
140: mirror
142: window
144: light collecting unit
146: cladding
148: black paint
150: spectroscope
152: photoelectric conversion unit
154: measurement operation unit
160: shutter
162: hole
164: optical transmission probe
166: bellows
170: exhaust unit
172: heater

The invention claimed is:

1. A method of monitoring plasma, comprising the steps of:
placing an antenna probe at a monitoring location set inside or near plasma existing within a certain space;
causing the antenna probe to irradiate a frequency-variable electromagnetic wave into the plasma;
receiving an electromagnetic wave reflected from the plasma to the antenna probe;
measuring a complex reflection coefficient based on the incident and reflected electromagnetic waves, and obtaining an imaginary part of the complex reflection coefficient;
measuring a resonance frequency at which the imaginary part of the complex reflection coefficient is zero by sweeping the frequencies of the electromagnetic wave; and
calculating electron density in the plasma based on the measured resonance frequency.

2. The method of claim 1, where a frequency at a point where a sign of the imaginary part of the complex reflection coefficient changes is determined as the resonance frequency by sweeping the frequencies of the electromagnetic waves.

3. The method of claim 2, further comprising the steps of:
in a state where the plasma does not exist in the space, obtaining a first frequency characteristic with respect to the imaginary part of the complex reflection coefficient by sweeping the frequencies of the electromagnetic waves;
in a state where the plasma exists in the space, obtaining a second frequency characteristic with respect to the imaginary part of the complex reflection coefficient by sweeping the frequencies of the electromagnetic waves; and
obtaining a normalized frequency characteristic based on the first and second frequency characteristics.

4. The method of claim 1, wherein
an insulating pipe is placed in or in the vicinity of the plasma between first and second supports provided in sidewalls of the chamber in which the plasma is created; and
a probe portion is positioned at the monitoring location in such a way as to insert a coaxial cable, which is the antenna probe and has the probe portion with a front core wire thereof being exposed, from one end of the insulating pipe.

5. The method of claim 4, wherein the coaxial cable is moved in the axial direction of the insulating pipe to change the monitoring location.

6. The method of claim 5, wherein the spatial distribution of electron density in the plasma is obtained after the location of the probe portion within the insulating pipe is changed.

7. An apparatus for monitoring plasma, comprising:
an antenna probe located in a wall of or inside a chamber in or into which plasma is created or introduced;
a vector reflection coefficient measuring unit for, while sweeping frequencies, transmitting electromagnetic waves of respective frequencies to the antenna probe to be irradiated to the plasma, receiving reflected waves from the plasma through the antenna probe, and measuring complex reflection coefficients;
a resonance frequency measuring unit for measuring a resonance frequency at which an imaginary part of the complex reflection coefficients is zero; and
an electron density operation unit for calculating electron density in the plasma based on the measured resonance frequency.

8. The apparatus of claim 7, wherein
the reflection coefficient measuring unit obtains frequency characteristic with respect to the imaginary part of the complex reflection coefficient by sweeping the frequencies of the electromagnetic waves; and
the resonance frequency measuring unit determines as the resonance frequency a frequency at a point where a sign of the imaginary part of the complex reflection coefficient changes in the frequency characteristics.

9. The apparatus of claim 8, wherein the reflection coefficient measuring unit obtains a first frequency characteristic in a state where the plasma does not exist in the chamber, a second frequency characteristic in a state where the plasma exists in the chamber, and a normalized frequency characteristic based on the first and second frequency characteristics, with respect to the imaginary part of the complex reflection coefficient.

10. The apparatus of claim 9, further comprising:
an insulating pipe inserted into and installed in the chamber; and
a coaxial cable used as the antenna probe, provided with a probe portion formed by exposing a front core wire of the coaxial cable, and inserted into the insulating pipe from one end of the insulating pipe.

11. The apparatus of claim 9, further comprising an actuator for moving the coaxial cable in the axial direction of the insulating pipe.

12. The apparatus of claim 10, wherein the insulating pipe is hung between first and second supports provided in the sidewalls of the chamber.

13. The apparatus of claim 12, wherein at least one of the first and second supports is formed of a through hole.

14. The apparatus of claim 13, further comprising an O-ring for air-tightly and fixedly attaching the insulating pipe in the through hole.

15. The apparatus of claim 10, further comprising a grounding conductor one end of which is connected to a grounding potential portion of the chamber and the other end of which is connected to the outer conductor of the coaxial cable.

16. The apparatus of claim 15, wherein an electromagnetic wave absorber for absorbing a noise signal propagating along the outer conductor through electromagnetic induction is provided at a location of the probe portion side of the coaxial cable when viewed from a location where the grounding conductor and the outer conductor of the coaxial cable are in contact with each other.

17. The apparatus of claim 16, wherein the electromagnetic wave absorber includes one or more bead-shaped ferrite members placed around the coaxial cable along the axial direction thereof.

18. The apparatus of claim 10, further comprising a cooling mechanism connected to the other end of the insulating pipe to allow cooling gas to flow inside the insulating pipe.

19. A plasma processing apparatus, comprising:
a chamber for accommodating therein an object to be processed;
a gas supply unit for supplying certain gas into the chamber;
a plasma creation unit for creating plasma, which is used to perform treatment on the object to be processed, by discharging electricity in the gas in the chamber;
a gas exhaust unit for maintaining the chamber at certain pressure by depressurizing the inside of the chamber;
an antenna probe located in the wall of or inside the chamber in or into which the plasma is created or introduced; and
a plasma monitoring device including:
a vector reflection coefficient measuring unit for, while sweeping frequencies, transmitting electromagnetic waves of respective frequencies to the antenna probe to be irradiated to the plasma, receiving reflected waves from the plasma through the antenna probe, and measuring complex reflection coefficients;
a resonance frequency measuring unit for measuring a resonance frequency at which an imaginary part of the complex reflection coefficients is zero; and
an electron density operation unit for calculating electron density in the plasma based on the measured resonance frequency.

20. The apparatus of claim 19, further comprising a monitor unit for monitoring a state of plasma processing in the chamber based on the electron density obtained by the plasma monitoring apparatus.

21. The apparatus of claim 19, further comprising a process control unit for controlling at least one of process parameters influencing plasma processing, thereby maintaining the electron density obtained by the plasma monitoring apparatus to be within a certain range.

22. The apparatus of claim 19, further comprising a seasoning control unit for performing seasoning based on the characteristic of the time variation of the electron density obtained by the plasma monitoring apparatus with respect to processing conditions after the cleaning of the chamber or the replacement of parts.

23. The apparatus of claim 22, wherein the seasoning control unit obtains a representative of the measured electron densities time-varying during the plasma processing with respect to respective dummy substrates being plasma-processed in the chamber, completing the seasoning when the representative is stabilized to an actual normal value between successive dummy substrates, and changes the dummy substrate being put into the chamber from to a normal substrate to be processed.

24. The apparatus of claim 19, wherein the antenna probe is attached to the wall of the chamber.

25. The apparatus of claim 19, wherein electrodes for creating the plasma are provided in the chamber, and the antenna probe is attached to the electrodes.

26. The apparatus of claim 19, wherein a mounting table for mounting the object to be processed is provided in the chamber, and the antenna probe is attached to the mounting table.

27. The apparatus of claim 19, further comprising a selection switch for selecting any one of a plurality of antenna probes arranged at different locations to be electrically connected to the reflection coefficient measuring unit.

28. The apparatus of claim 27, wherein the selection switch electrically connects the plurality of antenna probes to the reflection coefficient measuring unit sequentially in a time division manner.

29. A method of monitoring plasma, comprising the steps of:
  placing an antenna probe at a monitoring location set inside or in the vicinity of plasma existing within a certain space;
  irradiating a frequency-variable electromagnetic waves from the antenna probe to the plasma;
  receiving an electromagnetic waves reflected from the plasma to the antenna probe;
  measuring a phase difference between the incident and reflected waves;
  measuring a resonance frequency at which the phase difference is zero while sweeping the frequencies of the electromagnetic waves; and
  calculating electron density in the plasma based on the measured resonance frequency.

30. An apparatus for monitoring plasma, comprising:
  an antenna probe located in the wall of or inside a chamber in or into which plasma is created or introduced;
  a phase difference measuring unit for, while sweeping frequencies, transmitting electromagnetic waves of respective frequencies to the antenna probe to be irradiated to the plasma, receiving reflected waves from the plasma through the antenna probe, and measuring a phase difference between the incident and reflected waves;
  a resonance frequency measuring unit for measuring a resonance frequency at which the phase difference obtained by the phase difference measuring unit is zero; and
  an electron density operation unit for calculating electron density in the plasma based on the measured resonance frequency.

31. A plasma processing apparatus, comprising:
  a chamber for accommodating therein an object to be processed;
  a gas supply unit for supplying certain gas into the chamber;
  a plasma creation unit for creating plasma, which is used to perform treatment on the object to be processed, by discharging electricity in the gas in the chamber;
  a gas exhaust unit for maintaining the chamber at a certain pressure by depressurizing the inside of the chamber;
  an antenna probe located in the wall of or inside the chamber in or into which the plasma is created or introduced; and
  a plasma monitoring device including:
  a phase difference measuring unit for, while sweeping frequencies, transmitting an electromagnetic wave of respective frequencies to the antenna probe to be irradiated to the plasma, receiving reflected waves from the plasma through the antenna probe, and measuring a phase difference between the incident and reflected waves;
  a resonance frequency measuring unit for measuring a resonance frequency at which the phase difference obtained by the phase difference measuring unit is zero; and
  an electron density operation unit for calculating electron density in the plasma based on the measured resonance frequency.

* * * * *